US011738004B2

(12) United States Patent
Marnett et al.

(10) Patent No.: US 11,738,004 B2
(45) Date of Patent: *Aug. 29, 2023

(54) INDOMETHACIN ANALOGS FOR THE TREATMENT OF CASTRATE-RESISTANT PROSTATE CANCER

(71) Applicants: Vanderbilt University, Nashville, TN (US); The Trustees of the University of Pennsylvania, Philadelphia, PA (US)

(72) Inventors: Lawrence J. Marnett, Nashville, TN (US); Andy J. Liedtke, Nashville, TN (US); Trevor M. Penning, Springfield, PA (US); Adegoke O. Adeniji, Drexel Hill, PA (US); Michael C. Byrns, Philadelphia, PA (US)

(73) Assignees: Vanderbilt University, Nashville, TN (US); The Trustees of the University of Pennsylvania, Philadelphia, PA (US)

( * ) Notice: Subject to any disclaimer, the term of this patent is extended or adjusted under 35 U.S.C. 154(b) by 173 days.

This patent is subject to a terminal disclaimer.

(21) Appl. No.: 17/236,694

(22) Filed: Apr. 21, 2021

(65) Prior Publication Data
US 2021/0251960 A1 Aug. 19, 2021

Related U.S. Application Data

(60) Division of application No. 16/530,907, filed on Aug. 2, 2019, now abandoned, which is a division of application No. 15/899,171, filed on Feb. 19, 2018, now Pat. No. 10,398,678, which is a division of application No. 15/132,937, filed on Apr. 19, 2016, now Pat. No. 9,895,351, which is a continuation of application No. 14/352,421, filed as application No. PCT/US2012/060508 on Oct. 17, 2012, now Pat. No. 9,346,803.

(60) Provisional application No. 61/548,004, filed on Oct. 17, 2011.

(51) Int. Cl.
| | |
|---|---|
| *C07D 471/04* | (2006.01) |
| *A61K 31/405* | (2006.01) |
| *A61K 31/404* | (2006.01) |
| *C07D 209/26* | (2006.01) |
| *C07D 209/08* | (2006.01) |
| *C07D 209/70* | (2006.01) |
| *C07D 231/56* | (2006.01) |

(52) U.S. Cl.
CPC .......... *A61K 31/404* (2013.01); *A61K 31/405* (2013.01); *C07D 209/08* (2013.01); *C07D 209/26* (2013.01); *C07D 209/70* (2013.01); *C07D 231/56* (2013.01); *C07D 471/04* (2013.01)

(58) Field of Classification Search
CPC .................................................. C07D 209/04

USPC .......................................... 514/299; 548/469
See application file for complete search history.

(56) References Cited

U.S. PATENT DOCUMENTS

| | | |
|---|---|---|
| 3,161,654 A | 12/1964 | Shen |
| 3,196,162 A | 7/1965 | Sarett et al. |
| 3,285,908 A | 11/1966 | Shen |
| 3,336,194 A | 8/1967 | Shen |
| 3,470,203 A | 9/1969 | Gal et al. |
| 3,535,326 A | 10/1970 | Yamamoto et al. |
| 3,654,349 A | 4/1972 | Shen et al. |
| 3,687,969 A | 8/1972 | Alexander et al. |
| 3,725,548 A | 4/1973 | Shen et al. |
| 3,941,805 A | 3/1976 | Alexander |
| 4,009,181 A | 2/1977 | Berger |
| 4,028,382 A | 6/1977 | Alexander |
| 4,174,402 A | 11/1979 | Mielens |
| 4,229,447 A | 10/1980 | Porter |
| 4,412,994 A | 11/1983 | Sloan et al. |
| 4,851,426 A | 7/1989 | Ladkani et al. |
| 5,032,588 A | 7/1991 | Brooks et al. |
| 5,093,356 A | 3/1992 | Yves et al. |
| 5,360,925 A | 11/1994 | Chabrier De et al. |
| 5,436,265 A | 7/1995 | Black et al. |
| 5,475,021 A | 12/1995 | Marnett et al. |
| 5,504,086 A | 4/1996 | Ellinwood, Jr. et al. |
| 5,510,368 A | 4/1996 | Lau et al. |
| 5,607,966 A | 3/1997 | Hellberg et al. |
| 5,681,964 A | 10/1997 | Ashton et al. |

(Continued)

FOREIGN PATENT DOCUMENTS

| | | |
|---|---|---|
| DE | 1917128 | 4/1969 |
| DE | 1695703 | 4/1971 |

(Continued)

OTHER PUBLICATIONS

Adeniji et al. (2011) Discovery of substituted 3-(phenylamino)benzoic acids as potent and selective inhibitors of type 5 17p-hydroxysteroid dehydrogenase (AKR1C3). Bioorg Med Chem Lett 21:1464-1468.
Adeniji et al. (2012) Development of potent and selective inhibitors of aldo-keto reductase 1C3 (type 5 17β-hydroxysteroid dehydrogenase) based on N-phenyl-aminobenzoates and their structure activity relationships. J. Med. Chem. 55: 2311-2323.

(Continued)

*Primary Examiner* — Niloofar Rahman

(57) ABSTRACT

Provided are compositions for inhibiting a biological activity of an aldo-keto reductase family 1, member C3 (AKR1C3) polypeptide. In some embodiments, the compositions are indomethacin derivatives that are AKR1C3-specific inhibitors. Also provided are methods for producing disclosed indomethacin derivatives that substantially lack cyclooxygenase inhibitory activity but that have AKR1C3 inhibitory activity, methods for inhibiting AKR1C3 polypeptide biological activities, and methods for treating prostate tumors in subjects.

14 Claims, 18 Drawing Sheets

(56) References Cited

U.S. PATENT DOCUMENTS

| | | | |
|---|---|---|---|
| 5,811,425 A | 9/1998 | Woods et al. | |
| 5,811,438 A | 9/1998 | Hellberg et al. | |
| 5,861,419 A | 1/1999 | Dube et al. | |
| 5,877,199 A | 3/1999 | Birdsall et al. | |
| 5,922,742 A | 7/1999 | Black et al. | |
| 5,973,191 A | 10/1999 | Marnett et al. | |
| 6,004,991 A | 12/1999 | Fourtillan | |
| 6,045,773 A | 4/2000 | Isakson et al. | |
| 6,048,850 A | 4/2000 | Young et al. | |
| 6,207,700 B1 | 3/2001 | Kalgutkar et al. | |
| 6,277,878 B1 | 8/2001 | Nakao et al. | |
| 6,284,918 B1 | 9/2001 | Marnett et al. | |
| 6,306,890 B1 | 10/2001 | Kalgutkar et al. | |
| 6,472,433 B2 | 10/2002 | Wechter | |
| 6,593,334 B1 | 7/2003 | Lee et al. | |
| 6,620,851 B2 | 9/2003 | Jerussi et al. | |
| 6,762,182 B1 | 7/2004 | Kalgutkar et al. | |
| 6,933,316 B2 | 8/2005 | Hsieh et al. | |
| 7,074,826 B2 | 7/2006 | Wechter et al. | |
| 7,348,338 B2 | 3/2008 | Arnold | |
| 7,405,227 B2 | 7/2008 | Kun et al. | |
| 7,491,744 B2 | 2/2009 | Marnett et al. | |
| 7,736,624 B2 | 6/2010 | Marnett et al. | |
| 8,092,829 B2 | 1/2012 | Geisslinger et al. | |
| 8,143,302 B2 | 3/2012 | Marnett et al. | |
| 8,168,656 B2 | 5/2012 | Marnett et al. | |
| 9,346,803 B2 * | 5/2016 | Marnett | C07D 209/08 |
| 9,895,351 B2 * | 2/2018 | Marnett | A61K 31/404 |
| 10,398,678 B2 * | 9/2019 | Marnett | C07D 209/70 |
| 2005/0002859 A1 | 1/2005 | Marnett et al. | |
| 2006/0024365 A1 | 2/2006 | Vaya et al. | |
| 2007/0207949 A1 | 9/2007 | Ghosal et al. | |
| 2008/0176870 A1 | 7/2008 | Nolte et al. | |
| 2009/0076019 A1 | 3/2009 | Tyers et al. | |
| 2009/0118290 A1 | 5/2009 | Marnett et al. | |
| 2009/0181960 A1 | 7/2009 | Niimi et al. | |
| 2009/0220611 A1 | 9/2009 | Dargelas et al. | |
| 2019/0350903 A1 | 11/2019 | Marnett et al. | |

FOREIGN PATENT DOCUMENTS

| | | |
|---|---|---|
| DE | 2125926 | 5/1971 |
| DE | 2735537 | 2/1979 |
| DE | 3145465 | 5/1983 |
| DE | 3235850 | 8/1983 |
| DE | 3206885 | 9/1983 |
| DE | 10163426 | 7/2003 |
| EP | 0051278 | 5/1982 |
| EP | 0080271 | 6/1983 |
| EP | 0144845 | 6/1985 |
| EP | 0327766 | 8/1989 |
| EP | 335164 | 10/1989 |
| EP | 335545 | 10/1989 |
| EP | 342682 | 11/1989 |
| ES | 432545 | 11/1976 |
| FR | 2392008 | 12/1978 |
| HU | 155986 | 4/1986 |
| JP | S4935269 | 9/1974 |
| JP | 54-090174 | 7/1979 |
| JP | 58-201763 | 11/1983 |
| JP | 59-161358 | 9/1984 |
| JP | 60-152462 | 8/1985 |
| JP | 60-214768 | 10/1985 |
| JP | 61-060649 | 3/1986 |
| JP | 61-134371 | 6/1986 |
| JP | 63-196598 | 8/1988 |
| JP | 63-275593 | 11/1988 |
| NL | 7100213 | 7/1972 |
| NL | 8105139 | 6/1982 |
| WO | WO91/13060 | 9/1991 |
| WO | WO1995/004030 | 2/1995 |
| WO | WO1995/020567 | 8/1995 |
| WO | WO1995/022524 | 8/1995 |
| WO | WO1998/032718 | 7/1998 |
| WO | WO2001/093680 | 12/2001 |
| WO | WO2002/008188 | 1/2002 |
| WO | WO2002/020478 | 3/2002 |
| WO | WO2002/028831 | 4/2002 |
| WO | WO2002/060438 | 8/2002 |
| WO | WO2005009958 | 7/2003 |
| WO | WO2004/020409 | 3/2004 |
| WO | WO 2005/092062 | 10/2005 |
| WO | WO 2007/100066 | 9/2007 |
| WO | WO 2009/014150 | 1/2009 |

OTHER PUBLICATIONS

Ahn et al. (2009) Discovery and Characterization of a Highly Selective FAAH Inhibitor that Reduces Inflammatory Pain. Chem Biol 16:411-420.

Allen et al., Journal of Heterocyclic Chemistry (1970), 7(1 ), 239-41.

Andriole et al. (2010) Reduce Study Group. Effect of dutasteride on the risk of prostate cancer, N Engl J Med 362:1192-1202.

Attard et al. (2009a) Antitumor activity with CYP17 blockade indicates that castration-resistant prostate cancer frequently remains hormone driven, Cancer Res 69:4937-4940.

Bahner et al., "Anticancer Compounds. Further Analogs of 1-(4-dimethylaminobenzylidene) indene," Journal of Medicinal Chemistry, vol. 16, No. 4,, pp. 421-425 (1973).

Barasoain et al., "Indomethacin Esters Acting as Anti-Inflammatory and Immunosuppressive Drugs," International Journal of Clinical Pharmacology Biopharm., vol. 16, No. 5, pp. 235-239 (1978) (Abstract).

Barasoain et al.,"Immunosuppressive Effects of Some Organic Compounds with Anti-Inflammatory Activity," Proceedings of the International Congress of Chemotherapy, vol. 8, pp. 21-26 (1976) (Abstract).

Barbieri et al. (2006) "Microwave-assisted one-pot synthesis of substituted tetrahydrocarbazole and 8,9, 10, 11-tetrahydro-7H-pyrido[a]carbazoles", Tetrahedron Letters, 2006, vol. 47, pp. 8289-8292. 5-19.

Bhattacharyya et al. (1996) Involvement of arginine 120, glutamate 524, and tyrosine 355 in the binding of arachidonate and 2-phenylpropionic acid inhibitors to the cyclooxygenase active site of ovine prostaglandin endoperoxide H synthase-1. J Biol Chem 271:2179-2184.

Boltze et al., "Chemical Structure and Antiinflammatory Activity in the Group of Substituted Indole-3-Acetic Acids," Arzneim-Forsch., vol. 30, No. 8A, pp. 1314-1325 (1980) (with English Abstract).

Byrns et al. (2008) "An Indomethacin Analogue, N-(4-Chlorobenzoyl)-melatonin, is a Selective Inhibitor of Aldo-keto Reductase 1 C3 {Type 2 3a-HSD, Type 5 17Beta-HSD, and Prostaglandin y F Synthase), a Potential Target for the Treatment of Hormone Dependent and Hormone Independent Malignancies" Biochem Pharmacol. Jan. 15, 2008, vol. 75(2), pp. 484-493.

Byrns et al., Chemica-Biological interactions (2009), 178(1-3), 221-227.

Cai et al. (2011) Intratumoral De Novo Steroid Synthesis Activates Androgen Receptor in Castration-Resistant Prostate Cancer and Is Upregulated by Treatment with CYP17A1 Inhibitors, Cancer Res 71:6503-6513.

Correspondence (translation) regarding Notice of Acceptance corresponding to Israeli Patent Application No. 144,127 dated Jul. 5, 2006.

Correspondence (translation) regarding Office Action corresponding to Chinese Patent Application No. 99816425.9 dated Jun. 21, 2004.

Correspondence regarding Examiner's Report corresponding to Israeli Patent Application No. 144,126 dated Sep. 14, 2005.

Davies et al. (2009) AKR1C isoforms represent a novel cellular target for jsamonate alongside their mitochondrial-mediated effects, Cancer Res 69:4769-4775.

De Caprariis et al., "Synthesis and Pharmacological Evaluation of Oligoethylene Ester Derivatives as Indomethacin Oral Prodrugs," Journal of Pharmaceutical Science, vol. 83, No. 11, pp. 1578-1581 (1994) (Abstract).

Decision of Granting Patent Right for Invention corresponding to Chinese Patent Application No. 00814912.7 dated May 30, 2008.

(56) References Cited

OTHER PUBLICATIONS

Decision to grant a European patent pursuant to article 97(1) EPC corresponding to European Patent Application No. 16156925.6 dated May 23, 2019.
Decision to grant a European patent pursuant to article 97(2) EPC corresponding to European Patent Application No. 00957717.2-2117 dated Sep. 20, 2007.
Decision to grant a European patent pursuant to article 97(2) EPC corresponding to European Patent Application No. 99967416.1-2107 dated May 11, 2006.
Decision to grant a European patent pursuant to article 97(2) EPC corresponding to European Patent Application No. 99967417.9-1521 dated Apr. 26, 2007.
Desmond et al., Cancer research (2003), 63(2), 505-512.
Efstathiou et al. (2011) MDV3100 effects on androgen receptor (AR) signaling and bone marrow testosterone concentration modulation: A preliminary report. J. Clin. One., ASCO Meeting Abstracts: p. Abstract 4501.
Endo et ai.,Biological & pharmaceutical Bulletin (201 0), 33(5), 886-890.
European Search Report corresponding to European Patent Application 12842553.5-1462 /2768499 dated Jul. 27, 2015.
European Search Report corresponding to European Patent Application No. 00957717.2-2123 dated Nov. 16, 2004.
European Search Report corresponding to European Patent Application No. 04777110.0-1216 /163862 dated Aug. 31, 2010.
European Search Report corresponding to European Patent Application No. 07 809 688.0 dated Feb. 7, 2013.
European Search Report corresponding to European Patent Application No. 12842553.5-1462 /2768499 dated Feb. 23, 2015.
Ex Parte Quayle Action corresponding to U.S. Appl. No. 13/431,205 dated Feb. 10, 2014.
Extended European Search Report corresponding to European Patent Application No. 16156925.6 (dated Jul. 11, 2016).
Fisnerova et al., "Esters of 1-(p-chlorobenzoyl)-5-methoxy-2-methyl-3-indolylacetic Acid," Heterocycles, vol. 95 p. 667 (1981).
Fisnerova et al., "Pharmacologically Interesting Indomethacin Derivatives," Heterocycles, vol. 88 p. 373 (1978).
Fung et al. (2006) Increased expression of type 2 3a-hydroxysteroid dehydrogenase/type 5 17b-hydroxysteroid dehydrogenase (AKR1C3) and its relationship with the androgen receptor in prostate carcinoma, Endocr Related Cancer 13:169-180.
International Search Report corresponding to International Application No. PCT/US2012/060508 dated Feb. 19, 2013.
International Search Report corresponding to International Application No. PCT/US2013/051523 dated Jul. 16, 2015.
Jansson et al. (2006) 17β-Hydroxysteroid dehydrogenase 14 affects estradiol levels in breast cancer cells and is a prognostic marker in estrogen receptor-positive breast cancer, Cancer Res 66:11471-11477.
Kalgutkar et al. (1998a) Aspirin-Like Molecules that Covalently Inactivate Cyclooxygenase-2. Science 280:1268-1270.
Kalgutkar et al. (1998b) Covalent Modification of Cyclooxygenase-2 (COX-2) by 2-Acetoxyphenyl Alkyl Sulfides, a New Class of Selective COX-2 Inactivators. J. Med. Chem. 41:4800-4818.
Kalgutkar et al. (2000a) Biochemically based design of cyclooxygenase-2 (COX-2) inhibitors: Facile conversion of nonsteroidal anti-inflammatory drugs to potent and highly selective COX-2 inhibitors. PNAS, 97(2):925-930.
Kalgutkar et al. (2000b) Ester and Amide Derivatives of the Nonsteroidal Antiinflammatory Drug, Cyclooxygenase-2 Inhibitors. Journal of Medicinal Chemistry 43(15):2860-2870.
Kalgutkar et al. (2002) Amide Derivatives of Meclofenamic Acid as Selective Cyclooxygenase-2 Inhibitors. Bioorganic and Medicinal Chemistry Letters 12:521-524.
Kappe et al. (1990) Non-steroidal Antiinflammatory Agents. V. Basic Esters of Indomethacin. Journal für Praktische Chemie 332(4):475-478.

Khanna et al., "1,2-Diarylimidazoles as Potent Cyclooxygenase-2 Selective, and Orally Active Antiinflammatory Agents," Journal of Medicinal Chemistry, vol. 40, No. 11, pp. 1634-1647 (1997a).
Khanna et al., "1,2-Diarylpyrroles as Potent, and Selective Inhibitors of Cyclooxygenase-2," Journal of Medicinal Chemistry, vol. 40, No. 11, pp. 1619-1633 (1997c).
Kim et al. (2007) 15-Deoxy-$\Delta$12,14-prostaglandin J2 inhibits transcriptional activity of estrogen receptor-$\alpha$ via covalent modification of DNA-binding domain, Cancer Res 67:2595-2602.
Knudsen & Penning (2010) Partners in crime: deregulation of AR activity and androgen synthesis in prostate cancer, Trends Endocrinol Metab 21:315-324.
Knudsen & Scher (2009) Starving the addiction: New opportunities for durable suppression of AR signaling in prostate cancer, Clin Cancer Res 15:4792-4798.
Kozak et al., "Enantiospecific, Selective Cyclooxygenase-2 Inhibitors," Bioorganic & Medicinal Chemistry Letters, vol. 12, pp. 1315-1318 (2002).
Kurumbail et al., "Structural basis for selective inhibition of cyclooxygenase-2 by anti-inflammatory agents," Nature, vol. 384, pp. 644-648 (1996).
Li et al., "Cyclooxygenase-2 Inhibitors. Synthesis and Pharmacological Activities of 5-Methanesulfonamido-1-indanone Derivatives," Journal of Medicinal Chemistry, vol. 38, No. 25, pp. 4897-4905 (1995).
Li et al., "Novel Terphenyls as Selective Cyclooxygenase-2 Inhibitors and Orally Active Antiinflammatory Agents," Journal of Medicinal Chemistry, vol. 39, No. 9, pp. 1846-1856 (1996).
Liedtke et al., Development of Potent and Selective Indomethacin Analogues for the Inhibition of AKR1C3 (Type 5 17β-Hydroxysteroid Dehydrogenase/Prostaglandin F Synthase) in Castrate-Resistant.
Linari et al., "Substituted Anilides of 1-(p-Chlorobenzoyl)-5-methoxy-2-methyl-indole-3-acetic Acid," Arzneim-Foprsch. (Drug Research) vol. 23, No. 1, pp. 89-91 (1973).
Lodi et al., ACS chemical biology (2011 ), 6, 169-175.
Lovering et al., Cancer research (2004), 64(5), 1802-1810.
McCarthy et al., "Radiosynthesis, in vitro validation, and in vivo evaluation of 18F-labeled COX-1 and COX-2 inhibitors," Journal of Nuclear Medicine, vol. 43, No. 1, pp. 117-124 (2002).
Mielens et al., Pharmacology (1978), 17(6), 323-9.
Mitsiades et al. (2012) Distinct patterns of dysregulated expression of enzymes involved in androgen synthesis and metabolism in metastatic prostate cancer tumors. Cancer Res.
Montgomery et al. (2008) Maintenance of intratumoral androgens in metastatic prostate cancer: a mechanism for castration-resistant tumor growth, Cancer Res 68:4447-4454.
Mostaghel et al. (2011) Resistance to CYP17A1 inhibition with abiraterone in castrate-resista nee prostate cancer: induction of steroidogenesis and androgen receptor splice variants. Clin. Cancer Res., 17:5913-5925.
Notice of Acceptance and translation corresponding to Israeli Patent Application No. 144,126 dated Aug. 6, 2007.
Notice of Acceptance corresponding to Australian Patent Application No. 23697/00 dated Mar. 19, 2004.
Notice of Acceptance corresponding to Australian Patent Application No. 23698/00 dated Apr. 1, 2003.
Notice of Acceptance corresponding to Australian Patent Application No. 69297/00 dated Mar. 9, 2004.
Notice of Allowance and Interview Summary corresponding to U.S. Appl. No. 14/352,421 dated Jan. 20, 2016.
Notice of Allowance corresponding to Canadian Patent Application No. 2,358,289 dated Mar. 16, 2009.
Notice of Allowance corresponding to Canadian Patent Application No. 2,382,296 dated Feb. 3, 2009.
Notice of Allowance corresponding to Israeli Patent Application No. 144,126 dated Aug. 9, 2007 (translation).
Notice of Allowance corresponding to U.S. Appl. No. 09/226,693 dated Oct. 24, 2000.
Notice of Allowance corresponding to U.S. Appl. No. 09/385,748 dated Jun. 5, 2001.
Notice of Allowance corresponding to U.S. Appl. No. 09/818,201 dated Jan. 15, 2002.

(56) References Cited

OTHER PUBLICATIONS

Notice of Allowance corresponding to U.S. Appl. No. 09/869,384 dated Nov. 6, 2003.
Notice of Allowance corresponding to U.S. Appl. No. 11/114,921 dated Oct. 15, 2008.
Notice of Allowance corresponding to U.S. Appl. No. 11/820,481 dated Jan. 29, 2010.
Notice of Allowance corresponding to U.S. Appl. No. 12/319,262 dated Aug. 18, 2011.
Notice of Allowance corresponding to U.S. Appl. No. 12/814,143 dated Oct. 3, 2011.
Notice of Allowance corresponding to U.S. Appl. No. 13/431,205 dated May 28, 2014.
Notice of Decision Granting Patent Right for Invention corresponding to European Patent Application No. 05778497.7 dated Jan. 13, 2012.
Notice of Decision of Granting Patent Right for Invention corresponding to Chinese Patent Application No. 99816425.9 dated Dec. 3, 2004.
Notification Concerning Transmittal of International Preliminary Report on Patentability (Chapter I of the Patent Cooperation Treaty) corresponding to International Application No. PCT/US2004/020455 dated Jan. 12, 2006.
Notification Concerning Transmittal of International Preliminary Report on Patentability (Chapter I of the Patent Cooperation Treaty) corresponding to International Application No. PCT/US2005/014328 dated Mar. 15, 2007.
Notification Concerning Transmittal of International Preliminary Report on Patentability (Chapter 1 of the Patent Cooperation Treaty) corresponding to International Application No. PCT/US2007/014315 dated Jan. 8, 2009.
Notification Concerning Transmittal of International Preliminary Report on Patentability corresponding to International Application No. PCT/US2013/051523 dated Jun. 11, 2015.
Notification of Transmittal of International Search Report and the Written Opinion of the International Searching Authority, or the Declaration corresponding to International Application No. PCT/US2013/051523 dated Dec. 24, 2013.
Notification of Transmittal of the International Preliminary Examination Report corresponding to International Application No. PCT/US00/23153 dated Apr. 18, 2001.
Notification of Transmittal of the International Preliminary Examination Report corresponding to International Application No. PCT/US99/30219 dated Dec. 5, 2000.
Notification of Transmittal of the International Preliminary Examination Report corresponding to International Application No. PCT/US99/30220 dated Dec. 7, 2000.
Notification of Transmittal of the International Search Report and the Written Opinion of the International Searching Authority, or the Declaration corresponding to International Application No. PCT/US04/20455 dated Feb. 22, 2005.
Notification of Transmittal of the International Search Report and the Written Opinion of the International Searching Authority, or the Declaration corresponding to International Application No. PCT/US05/14328 dated Jan. 31, 2007.
Notification of Transmittal of the International Search Report and the Written Opinion of the International Searching Authority, or the Declaration corresponding to International Application No. PCT/US07/14315 dated Aug. 14, 2008.
Notification of Transmittal of the International Search Report or the Declaration corresponding to International Application No. PCT/USOO/23153 dated Oct. 26, 2000.
Notification of Transmittal of the International Search Report or the Declaration corresponding to International Application No. PCT/US99/30219 dated Apr. 5, 2000.
Notification of Transmittal of the International Search Report or the Declaration corresponding to International Application No. PCT/US99/30220 dated Apr. 4, 2000.
Odenwaller et al., "Preparation and Proteolytic Cleavage of Apoprostaglandin Endoperoxide Synthase," Methods in Enzymology, vol. 187, pp. 479-485 (1990).
Official Action (Restriction Requirement) corresponding to U.S. Appl. No. 16/530,907 dated Jun. 8, 2020.
Official Action (Restriction Requirement) corresponding to U.S. Appl. No. 16/530,907 dated Mar. 23, 2020.
Official Action corresponding to Australian Patent Application No. 23697/00 dated Dec. 16, 2003.
Official Action corresponding to Australian Patent Application No. 23697/00 dated Nov. 15, 2002.
Official Action corresponding to Australian Patent Application No. 23698/00 dated Nov. 15, 2002.
Official Action corresponding to Australian Patent Application No. 69297/00 dated Nov. 17, 2003.
Official Action corresponding to Canadian Patent Application No. 2,358,241 dated Aug. 28, 2008.
Official Action corresponding to Canadian Patent Application No. 2,358,289 dated Apr. 15, 2008.
Official Action corresponding to Canadian Patent Application No. 2,358,289 dated Sep. 2, 2009.
Official Action corresponding to Canadian Patent Application No. 2,382,296 dated Apr. 1, 2008.
Official Action corresponding to Canadian Patent Application No. 2,382,296 dated Apr. 16, 2012.
Official Action corresponding to Canadian Patent Application No. 2,382,296 dated Sep. 17, 2007.
Official Action corresponding to Canadian Patent Application No. 2,530,408 dated Mar. 2, 2011.
Official Action corresponding to Canadian Patent Application No. 2,657,691 dated Aug. 21, 2014.
Official Action corresponding to Canadian Patent Application No. 2,657,691 dated Nov. 25, 2013.
Official Action corresponding to Chinese Patent Application No. 200580021387.8 dated Oct. 9, 2009.
Official Action corresponding to Chinese Patent Application No. 200780030881.X dated Feb. 24, 2011.
Official Action corresponding to Chinese Patent Application No. 99816425.9 dated Aug. 20, 2003.
Official Action corresponding to European Patent Application No. 00957717.2-2117 dated Jul. 13, 2006.
Official Action corresponding to European Patent Application No. 04777 110.0-1216 dated Jan. 26, 2011.
Official Action corresponding to European Patent Application No. 04777 110.0-1453 dated May 19, 2014.
Official Action corresponding to European Patent Application No. 05 778 497.7-2123 dated Mar. 12, 2010.
Official Action corresponding to European Patent Application No. 05 778 497.7-2123 dated Nov. 29, 2010 (Summons to Attend Oral Proceedings).
Official Action corresponding to European Patent Application No. 99 967 416.1-2107 dated May 27, 2004.
Official Action corresponding to European Patent Application No. 99 967 416.1-2107 dated Aug. 31, 2005.
Official Action corresponding to European Patent Application No. 99 967 417.9-1521 dated Apr. 6, 2004.
Official Action corresponding to European Patent Application No. 99 967 417.9-1521 dated Feb. 11, 2005.
Official Action corresponding to European Patent Application No. 99 967 417.9-1521 dated Nov. 8, 2005.
Official Action corresponding to Japanese Patent Application No. 2000-591861 dated Aug. 3, 2010.
Official Action corresponding to Japanese Patent Application No. 2000-591862 dated May 6, 2010.
Official Action corresponding to Japanese Patent Application No. 2001-519900 dated Dec. 21, 2010.
Official Action corresponding to Japanese Patent Application No. 2006-517674 dated Aug. 27, 2010.
Official Action corresponding to Japanese Patent Application No. 2007-509739 dated Jul. 5, 2011.
Official Action corresponding to Japanese Patent Application No. P179096 dated May 10, 2010 (translation).

(56) References Cited

OTHER PUBLICATIONS

Official Action corresponding to Republic of China (Taiwan) U.S. Appl. No. 89/117,582 dated Dec. 20, 2003.
Official Action corresponding to Republic of China (Taiwan) U.S. Appl. No. 89/117,582 dated Jan. 26, 2007.
Official Action corresponding to Republic of China (Taiwan) U.S. Appl. No. 89/117,582 dated Jul. 1, 2005.
Official Action corresponding to Republic of China (Taiwan) U.S. Appl. No. 89/117,582 dated May 19, 2006.
Official Action corresponding to U.S. Appl. No. 09/226,693 dated Mar. 27, 2000.
Official Action corresponding to U.S. Appl. No. 09/385,748 dated Aug. 7, 2000.
Official Action corresponding to U.S. Appl. No. 09/385,748 dated Nov. 13, 2000.
Official Action corresponding to U.S. Appl. No. 09/869,384 dated Apr. 8, 2003.
Official Action corresponding to U.S. Appl. No. 09/869,384 dated Nov. 22, 2002.
Official Action corresponding to U.S. Appl. No. 10/877,303 dated Apr. 3, 2008.
Official Action corresponding to U.S. Appl. No. 10/877,303 dated Jul. 24, 2007.
Official Action corresponding to U.S. Appl. No. 10/877,303 dated Oct. 16, 2008.
Official Action corresponding to U.S. Appl. No. 11/114,921 dated Aug. 17, 2007.
Official Action corresponding to U.S. Appl. No. 11/114,921 dated Jun. 24, 2008.
Official Action corresponding to U.S. Appl. No. 11/114,921 dated Mar. 6, 2008.
Official Action corresponding to U.S. Appl. No. 11/820,481 dated Aug. 17, 2009.
Official Action corresponding to U.S. Appl. No. 11/820,481 dated Dec. 15, 2008.
Official Action corresponding to U.S. Appl. No. 11/820,481 dated Jun. 23, 2008.
Official Action corresponding to U.S. Appl. No. 12/319,262 dated Dec. 30, 2009.
Official Action corresponding to U.S. Appl. No. 12/319,262 dated Jun. 25, 2010.
Official Action corresponding to U.S. Appl. No. 12/319,262 dated Oct. 22, 2009.
Official Action corresponding to U.S. Appl. No. 12/423,358 dated Jan. 31, 2013.
Official Action corresponding to U.S. Appl. No. 12/423,358 dated Jun. 28, 2012.
Official Action corresponding to U.S. Appl. No. 12/423,358 dated May 27, 2011.
Official Action corresponding to U.S. Appl. No. 12/423,358 dated Nov. 12, 2013.
Official Action corresponding to U.S. Appl. No. 12/423,358 dated Sep. 9, 2011.
Official Action corresponding to U.S. Appl. No. 12/814,143 dated Jan. 14, 2011.
Official Action corresponding to U.S. Appl. No. 12/814,143 dated Oct. 8, 2010.
Official Action corresponding to U.S. Appl. No. 13/431,205 dated Feb. 28, 2013.
Official Action corresponding to U.S. Appl. No. 13/431,205 dated Oct. 28, 2013.
Official Action corresponding to U.S. Appl. No. 14/352,421 dated Jul. 9, 2015.
Official Action corresponding to U.S. Appl. No. 14/352,421 dated Sep. 10, 2015.
Official Action corresponding to U.S. Appl. No. 15/899,171 dated Nov. 23, 2018.
Official Action corresponding to U.S. Appl. No. 16/530,907 dated Oct. 22, 2020.

Otis et al., "Synthesis and Pharmacological Evaluation of Amide Derivatives of Non-steroidal Anti-Inflammatory Drugs," Inflammopharmacology, vol. 1, No. 3, pp. 201-212 (1992).
O'Sullivan et al., "Lipopolysaccharide-induced expression of prostaglandin H synthase-2 in alveolar macrophages is inhibited by dexamethasone but not by aspirin," Biochemical and Biophysical Research Communications, vol. 191, No. 3, pp. 1294-1300 (1993).
Pal et al., "7-Oxabicycloheptylprostanoic Acids: Potent, Time-Dependent Cyclooxygenase Inhibitors that Induce a Conformational Change in the Prostaglandin Endoperoxide Synthase Protein," Journal of Medicinal Chemistry, vol. 35, No. 12, pp. 2340-2342 (1992).
Penning et al. (2000) Human 3a-hydroxysteroid dehydrogenase isoforms (AKR1C1-AKR1C4) of the aldo keto reductase superfamily: functional plasticity and tissue distribution reveals roles in the inactivation and formation of male and female sex hormones, Biochem J 351:67-77.
Penning et al. (2006) Aldo-keto reductase (AKR) 1C3: Role in prostate disease and the development of specific inhibitors, Mol Cell Endcorinol 248:182-191.
Penning et al., "Synthesis and Biological Evaluation of the 1,5-Diarylpyrazole Class of Cyclooxygenase-2 Inhibitors: Indentification of 4-[5(4-Methylphenyl)-3- (trifluoromethyl)-1H-pyrazol-1yl]benzenesulfonamide (SC-58635, Celecoxib)," Journal of Medicinal Chemistry, vol. 40, pp. 1347-1365 (1997).
Qiu et al. (2007) Structure-based inhibitor design for an enzyme that binds different steroids: a potent inhibitor for human type 5 17b-hydroxysteroid dehydrogenase, J Biol Chem 282:8368-8379.
Reid et al. (2010) Significant and sustained antitumor activity in post-docetaxel, castration-resistant prostate cancer with the CYP17 inhibitor abiraterone acetate, J Clin Oncol 28:1489-1495.
Restriction Requirement corresponding to U.S. Appl. No. 15/132,937 dated Dec. 16, 2016.
Rizner et al., (2003) Human type 3 3alpha-hydroxysteroied dehydrogenase (aldo-keto reductase 1C2) and androgen metabolism in prostate cancer cells. Endocrinology 144: 2922-2932.
Rojo et al., "Variable Effects of Indomethacin and Four Related Compounds on Lymphocyte Blastogenesis and Cell-mediated Cytotoxicity," International Journal of Clinical Pharmacology, Therapy, and Toxicology, vol. 19, No. 9, pp. 420-424 (1981) (Abstract).
Rosenbaum et al., Angewandte Chemie, International Edition (2003), vol. Date 2004, 43(2), 224-228.
Rouzer et al., "Cyclooxygenase-1-dependent Prostaglandin Synthesis Modulates Tumor Necrosis Factor-( Secretion in Lipopolysaccharide-challenged Murine Resident Peritoneal Macrophages," The Journal of Biological Chemistry, vol. 279, No. 33, pp. 34256-34268 (2004).
Roy et al., "A New Series of Selective COX-2 Inhibitors; 5,6-Diarylthiazolo[3,2-b][1,2,4]Triazoles," Bioorganic & Medicinal Chemistry Letters, vol. 7, No. 1, pp. 57-62 (1997).
Sales et al. (2004) Expression, localization, and signaling of prostaglandin F2α receptor in human endometrial adenocarcinoma: regulation of proliferation by activation of the epidermal growth factor receptor and mitogen-activated protein kinase signaling pathways, J Clin Endocrinol Metab 89:986-993.
Sales et al. (2005) A novel angiogenic role for prostaglandin F2α-FP receptor interaction in human endometrial adenocarcinomas, Cancer Res 65:7707-7716.
Skarydova et al. (2009) AKR1C3 as a potential target for the inhibitory effect of dietary flavonoids, Chem Biol Inter 178:138-144.
Stefane et al. (2009) New cylcopentane derivatives as inhibitors of steroid metabolizing enzymes AKR1C1 and AKR1C3, Eur J Med Chem 44:2563-2571.
Straus et al. (2000) 15-Deoxy-Δ12,14-prostaglandin J2 inhibits multiple steps in the NF-κB signaling pathway, Proc Natl Acad Sci U S A 97:4844-4849.
Supplemental European Search Report corresponding to European Patent Application No. 99967416.1-2107 dated Apr. 8, 2003.
Supplementary European Search Report corresponding to European Patent Application No. 99967417.9 dated Jul. 25, 2003.
Supplementary European Search Report corresponding to International Patent Application No. 05778497.7-2123/1744747 dated Nov. 2, 2009.

(56) References Cited

OTHER PUBLICATIONS

Süreyya Ölgen et al., "Synthesis and biological evaluation of N-substituted indole esters as inhibitors of cyclo-oxygenase-2 (COX-2)," II Farmaco, vol. 57, No. 8, pp. 677-683 (Jul. 1, 2002).

Torisu et al., Bioorganic & Medicinal Chemistry letters (2004), 14(17), 4557-4562.

Torisu et al., European Journal of medicinal Chemistry (2005), 40(5), 505-519.

Touhey et al., "Structure-Activity Relationship of Indomethicin Analogues for MRP-1, COX-1 and COX-2 Inhibition: Identification of Novel Chemotherapeutic Drug Resistance Modulators," European Journal of Cancer, vol. 38, No. 12, pp. 1661-1670 (2002).

Tran et al. (2009) Development of a second-generation antiandrogen for treatment of advanced prostate cancer, Science 324:787-790.

Uddin et al. (2010) Selective visualization of cyclooxygenase-2 in inflammation and cancer by targeted fluorescent imaging agents. Cancer Res 70:3618-3627.

Uddin et al. (2011) Fluorinated COX-2 Inhibitors as Agents in PET Imaging of Inflammation and Cancer. Cancer Prev Res 4:1536-1545.

Usami et al. (2002) Substrate specifcity of human 3(20a)-hydroxysteroid dehydrogenase for neurosteroids and its inhibition by benzodiazepines, Biol Pharm Bull 25:441-445.

Vasaitis et al. (2008) Androgen receptor inactivation contributes to antitumor efficacy of 17a-hydroxylase/17,20-lyase inhibitor 3b-hydroxy-17-(1H-benzimidazole-1-yl)androsta-5,16-diene in prostate cancer, Mol Cancer Therap 7:2348-2357.

Veliça et al. (2009) Lack of functional and expression homology between human and mouse aldo-keto reductase 1C enzymes: implications for modelling human cancers, Mol Cancer 14:121.

Welstead et al., "Synthesis and antiinflammatory activity of a series of 2-aroyl-1,1a,2,6b-tetrahydrocycloprop[b] in dole-1-carboxylic acids," Journal of Medicinal Chemistry, vol. 17, No. 5, pp. 544-547 (May 1, 1974).

Written Opinion of the International Searching Authority corresponding to International Application No. PCT/US2012/060508 dated Feb. 19, 2013.

* cited by examiner

Indomethacin
 2'-Des-methyl Indomethacin analogs
 3'-Methyl-indomethacin analogs
 Compound 1
 Compound 2
 Compound 3

2'-Des-methyl analogs $R_2$ = H; -CH$_3$; (CH$_2$)$_n$CH$_3$ ; X = Halogen; NO$_2$; CF$_3$; CH$_3$; CH$_3$O-; OH; NH$_2$ etc.

3'-Methyl analogs $R_2$ = H; -CH$_3$; (CH$_2$)$_n$CH$_3$ ; X = Halogen; NO$_2$; CF$_3$; CH$_3$; CH$_3$O-; OH; NH$_2$ etc.

Compound 4, 5 Series

Compound 6 Series $R_1$ = CH$_3$; (CH$_2$)n-CH$_3$; (CH$_2$)n-COOH $R_2$ = (CH$_2$)n-CH$_3$; (CH$_2$)n-COOH $R_3$ = ortho, meta, para: halogen; NO$_2$; CF$_3$; CH$_3$-; CH$_3$O-; NH$_2$; OH; etc

INDOMETHACIN ANALOGS FOR THE TREATMENT OF CASTRATE-RESISTANT PROSTATE CANCER

CROSS REFERENCE TO RELATED APPLICATIONS

This application is a divisional of U.S. patent application Ser. No. 16/530,907, filed Aug. 2, 2019 (pending), which itself is a divisional of U.S. patent application Ser. No. 15/899,171, filed Feb. 19, 2018 (now U.S. Pat. No. 10,398,678), which itself is a U.S. patent application Ser. No. 15/132,937, filed Apr. 19, 2016 (now U.S. Pat. No. 9,895,351), which itself is a continuation of U.S. patent application Ser. No. 14/352,421, filed Apr. 17, 2014 (now U.S. Pat. No. 9,346,803), which itself is a United States National Stage filing of PCT International Patent Application Serial No. PCT/US2012/060508, filed Oct. 17, 2012, which itself is based on and claims priority to U.S. Provisional Patent Application Ser. No. 61/548,004, filed Oct. 17, 2011. The disclosure of each of these applications is herein incorporated by reference in its entirety.

GOVERNMENT INTEREST

This invention was made with government support under grant numbers CA90744 and CA89450 awarded by the National Institutes of Health. The government has certain rights in the invention.

TECHNICAL FIELD

The presently disclosed subject matter relates to methods and compositions for inhibiting a biological activity of a human aldo-keto reductase family 1, member C3 (AKR1C3; also known as type 5 17β-hydroxysteroid dehydrogenase) polypeptide. In some embodiments, the compositions comprise indomethacin derivatives that are AKR1C3-specific inhibitors. In some embodiments, the methods comprise administering a composition comprising an AKR1C3-specific inhibitor to a subject in order to modulate cellular or tissue proliferation, which in some embodiments can be a prostate cancer and in some embodiments a castrate-resistant prostate cancer.

BACKGROUND

Prostate cancer is the second most common cancer in men, and 160,000 new cases are diagnosed annually in the United States (Jermal et al., 2007). Twenty-percent of all cases develop into castrate-resistant prostate cancer (CRPC), which often presents with metastatic bone disease and is always fatal (Knudsen & Scher, 2009). CRPC often arises because tumors synthesize androgens independently of the testes (Knudsen & Penning, 2010). Thus, treatment approaches for such cancers represent a need in the art.

SUMMARY

This Summary lists several embodiments of the presently disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned, likewise, those features can be applied to other embodiments of the presently disclosed subject matter, whether listed in this Summary or not. To avoid excessive repetition, this Summary does not list or suggest all possible combinations of such features.

In some embodiments, the presently disclosed subject matter provides compounds having one of the following structures:

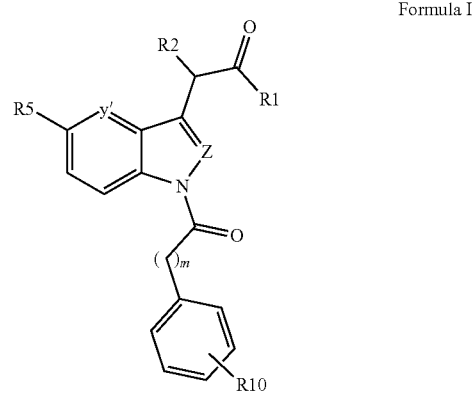

Formula I

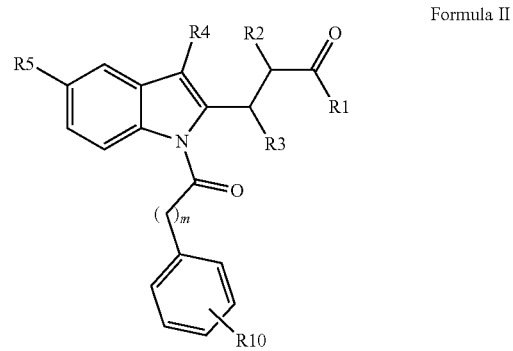

Formula II

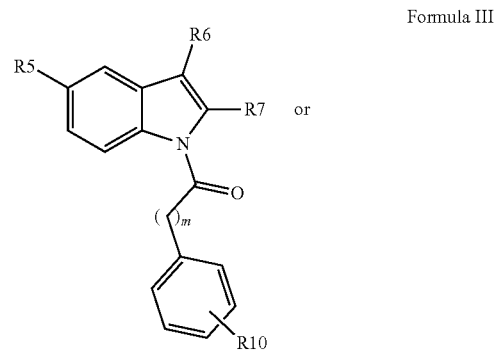

Formula III or

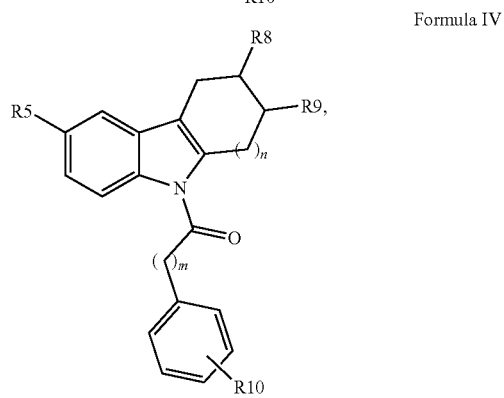

Formula IV wherein:

R1 is selected from the group consisting of OH, OCH₃, OCH₂CH₃ and HNSO₂X;

R2 is hydrogen or R— or S—C₁-C₆ alkyl;

R3 is hydrogen or R— or S—C₁-C₆ alkyl;

R4 is C₁ to C₆ alkyl;

R5 is hydrogen, C₁ to C₆ alkoxy or halogen;

R6 is C₁ to C₆ alkyl or C₁ to C₆ alkylcarboxylic acid or C₁ to C₆ alkyl-C(O)OR12 or C₁ to C₆ alkyl-C(O)N(H)SO₂X;

R7 is hydrogen or C₂ to C₆ alkyl or C₂ to C₆ alkylcarboxylic acid or C₂ to C₆ alkyl-C(O)OR12 or C₂ to C₆ alkyl-C(O)N(H)SO₂X;

R8 is hydrogen or R- or S-carboxylic acid or C(O)OR12 or C(O)N(H)SO₂X;

R9 is hydrogen or R- or S-carboxylic acid or C(O)OR12 or C(O)N(H)SO₂X; the ring to which R8 or R9 are bound is cyclopentyl or cyclohexyl;

R10 is present in two, three, four, or five positions in the phenyl ring and each instance is independently selected from the group consisting of hydrogen, halogen, nitro, C₁ to C₆ alkyl, singly or multiply halogen substituted C₁ to C₆ alkyl, C₁ to C₆ alkoxy, amino, and hydroxy;

X is methyl or singly or multiply halogen substituted methyl; phenyl, optionally singly or multiply substituted phenyl or thiophenyl, wherein the single or multiple substitutions of the phenyl or thiophenyl are each independently selected from the group consisting of halogen, nitro, C₁ to C₆ alkyl, singly or multiply halogen substituted C₁ to C₆ alkyl, trifluoromethyl, acetyl, isopropyl, C₁ to C₆ alkoxy, trifluoromethyloxy, phenoxy, cyano, hydroxy, and amino;

Y and Z are each individually CH or N; and m and n are each individually 0 or 1.

In some embodiments, the compound has one of the following structures:

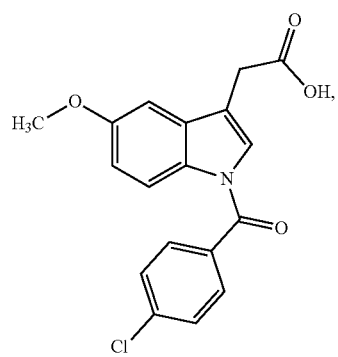

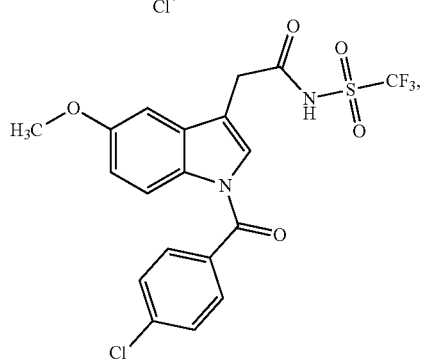

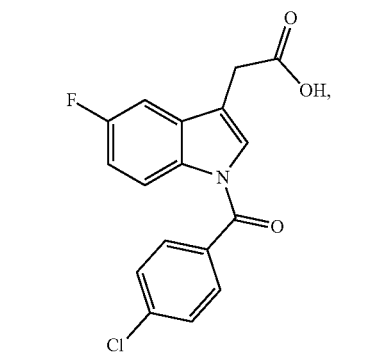

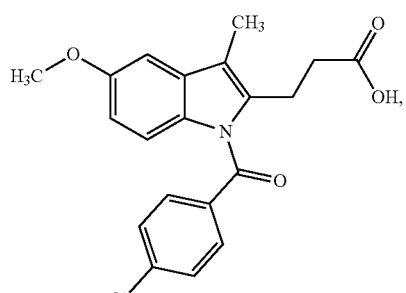

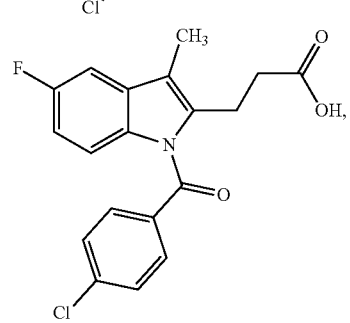

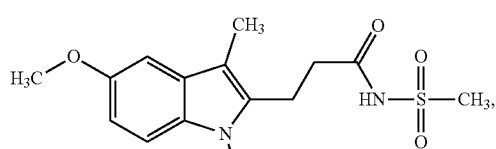

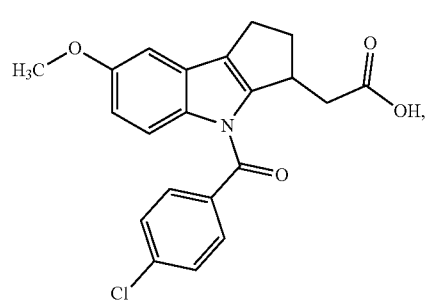

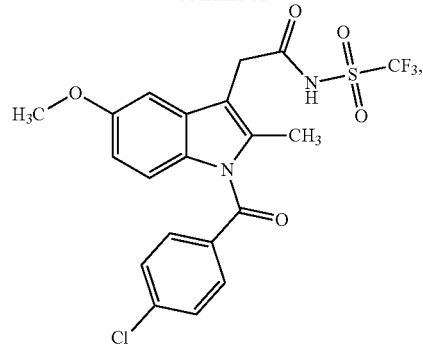
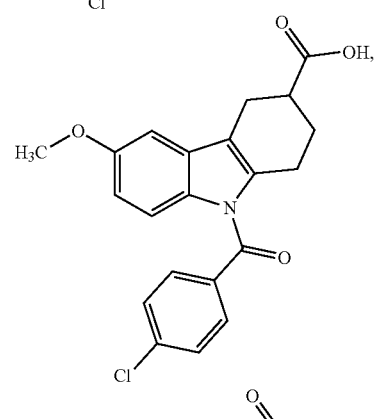
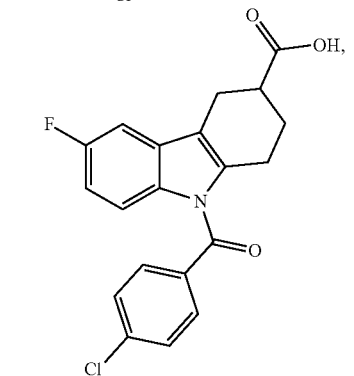
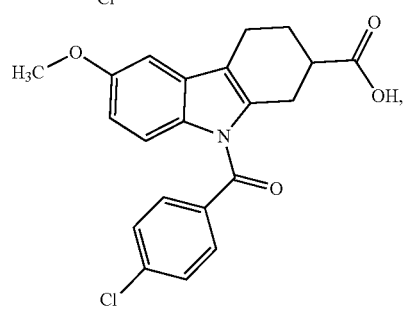
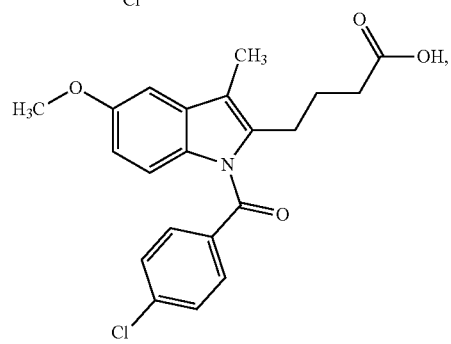
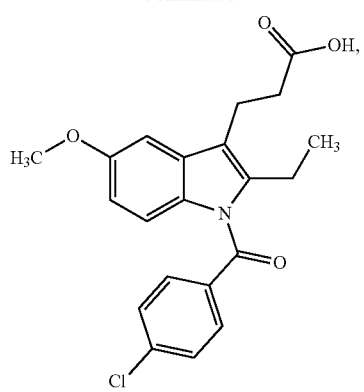
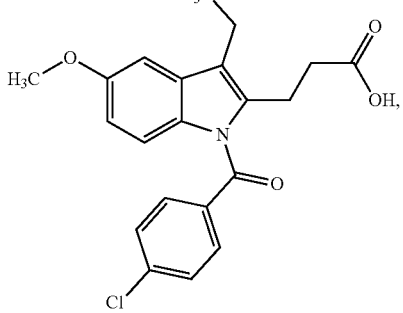
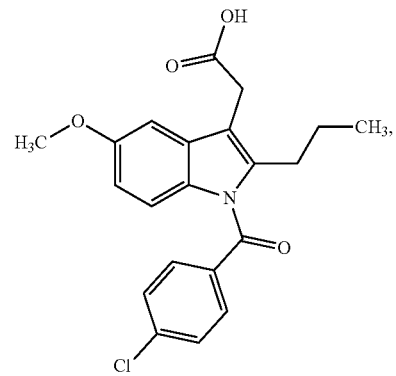
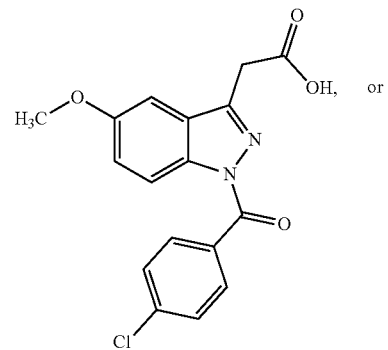

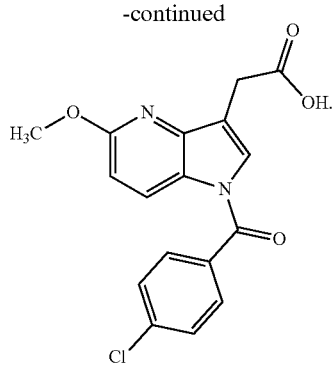

The presently disclosed subject matter also provides methods for producing an indomethacin derivative that substantially lacks cyclooxygenase inhibitory activity but that has AKR1C3 inhibitory activity. In some embodiments, the methods comprise modifying indomethacin, or a derivative or salt thereof, to produce a compound with one of the structures set forth hereinabove as Formulae I-IV.

In some embodiments, the compound has one of the following structures:

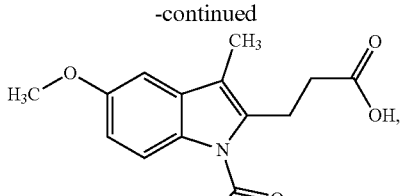

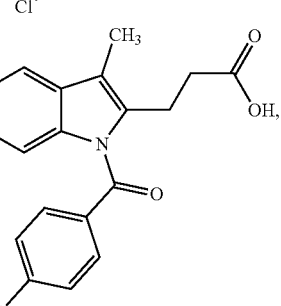

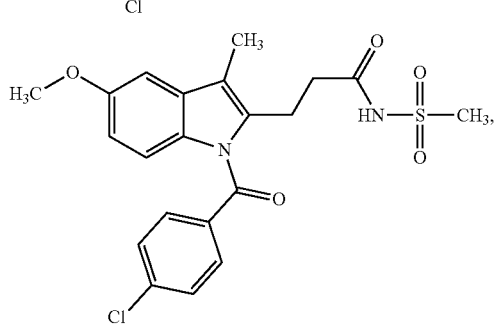

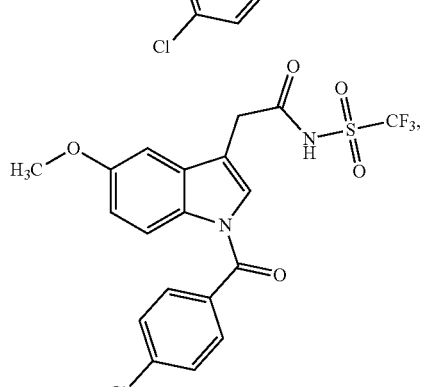

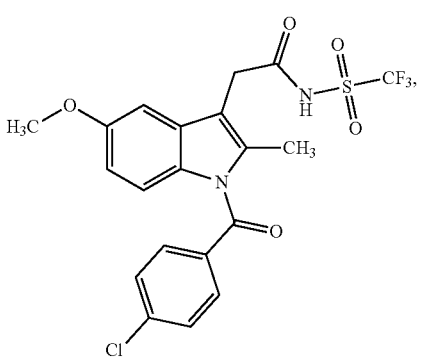

-continued
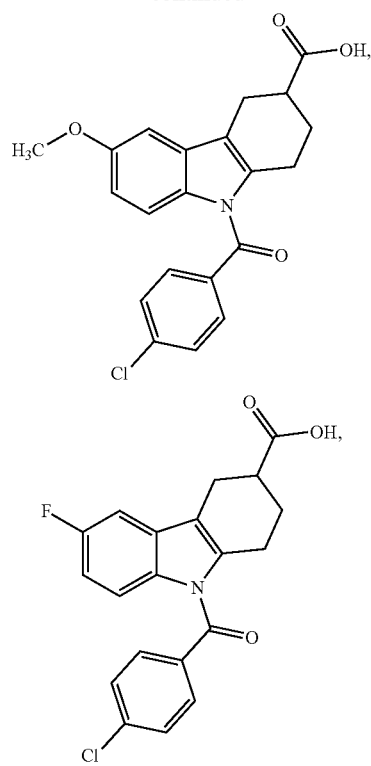
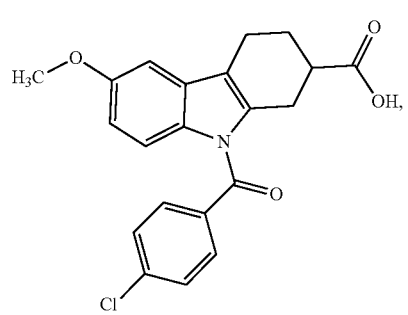
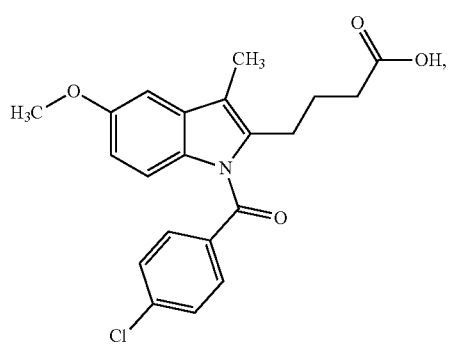
-continued
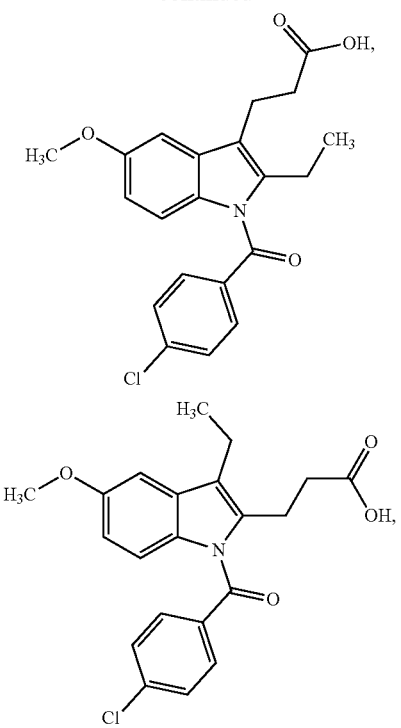
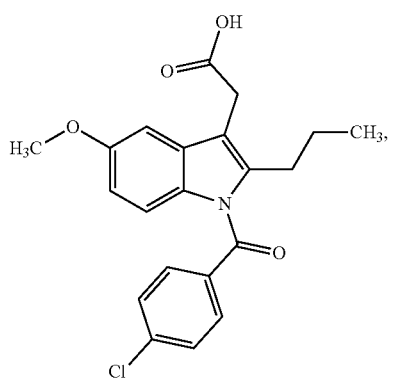
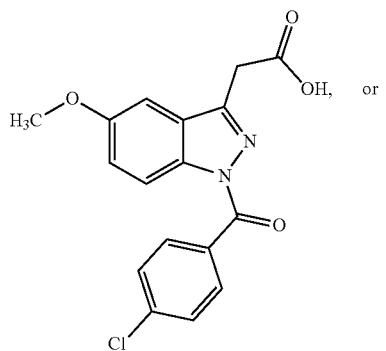
or

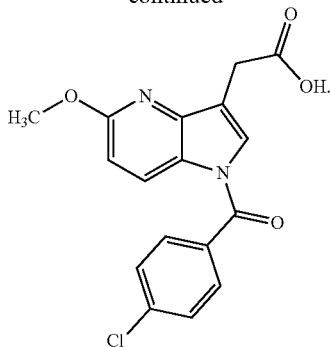

The presently disclosed subject matter also provides methods for producing an indomethacin derivative that substantially lacks cyclooxygenase inhibitory activity but that has AKR1C3 inhibitory activity. In some embodiments, the methods comprise performing a microwave-assisted reaction between a $C_1$ to $C_6$ alkoxy- or halo-substituted phenylhydrazine or a salt thereof and a cyclic or acyclic aliphatic ketoacid or alkyl ester thereof thereby providing an indole alkyl carboxylic acid or ester thereof, wherein the indole alkyl carboxylic acid or ester is a synthetic precursor of the indomethacin derivative. In some embodiments, the microwave-assisted reaction is performed in the presence of sulfuric acid. In some embodiments, the microwave-assisted reaction is performed in an alcoholic solvent, preferably methanol or ethanol, and in some embodiments, the microwave-assisted reaction is performed in acetic acid. In some embodiments, the $C_1$ to $C_6$ alkoxy- or halo-substituted phenylhydrazine or salt thereof is a compound of Formula V:

Formula V

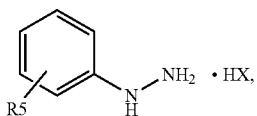

wherein R5 is hydrogen, $C_1$ to $C_6$ alkoxy, or halogen, and X is halogen, optionally Cl. In some embodiments, the cyclic or acyclic aliphatic ketoacid or alkyl ester thereof is a compound of Formula VI:

Formula VI

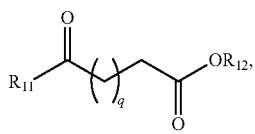

or a compound of Formula VII:

Formula VII

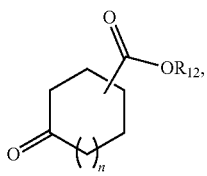

wherein R11 is $C_1$-$C_6$ alkyl; R12 is H, methyl or ethyl; q is an integer from 0 to 2; and n is 0 or 1. In some embodiments, the cyclic or acyclic aliphatic ketoacid or alkyl ester thereof is selected from the group consisting of 3-oxopentanoic acid, 4-oxobutanoic acid, 4-oxopentanoic acid, 5-oxohexanoic acid, 4-oxohexanoic acid, 4-oxoheptanoic acid, 4-oxocyclohexanecarboxylic acid, 3-oxocyclohexanecarboxylic acid or a methyl or ethyl ester thereof. In some embodiments, the indole alkyl carboxylic acid or ester has a structure of one of Formula VIII or Formula IX:

Formula VIII

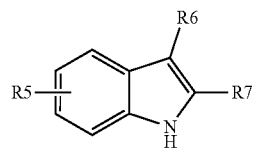

Formula IX

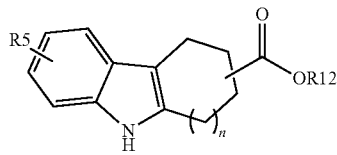

wherein R5 is hydrogen, $C_1$ to $C_6$ alkoxy or halogen; R6 is $C_1$ to $C_6$ alkyl or $C_1$ to $C_6$ alkylcarboxylic acid or $C_1$ to $C_6$ alkyl-C(O)OR$_{12}$; R7 is $C_2$ to $C_6$ alkylcarboxylic acid or $C_2$ to $C_6$ alkyl-C(O)OR$_{12}$; R12 is H, methyl or ethyl; and n is 0 or 1.

In some embodiments, the methods further comprise reacting the indole alkyl carboxylic acid or ester thereof with an aliphatic or aromatic acid halide to introduce an acyl substituent at the indole nitrogen atom, thereby providing a N-acylated indole alkyl carboxylic acid or ester thereof. In some embodiments, the reacting is performed by contacting the indole alkyl carboxylic acid or ester with an alkoxide, preferably sodium or potassium tert-butoxide, thereby deprotonating the indole nitrogen atom; and contacting the deprotonated indole alkyl carboxylic acid or ester with the aliphatic or aromatic acid halide. In some embodiments, one or both of the contacting steps are performed in tetrahydrofuran (THF). In some embodiments, the aliphatic or aromatic acid halide is an acid chloride. In some embodiments, the acid chloride is selected from the group consisting of 4-chlorobenzoyl chloride, 4-fluorobenzoyl chloride, 3-(trifluoromethyl)benzoyl chloride, 4-(trifluoromethyl)benzoyl chloride, 4-methoxybenzoyl chloride, 4-methylbenzoyl chloride. 4-(chloromethyl)benzoyl chloride, and 2-(4-chlorophenylacetyl chloride.

In some embodiments, the methods further comprise hydrolysis of an ester group in an N-acylated indole alkyl carboxylic ester to provide a N-acylated indole alkyl carboxylic acid. In some embodiments, the hydrolysis is performed using trimethyltin hydroxide and microwave radiation. In some embodiments, the hydrolysis is performed using 1,2-dichloroethane as a solvent.

The presently disclosed subject matter also provides methods for inhibiting a biological activity of an AKR1C3 polypeptide. In some embodiments, the methods comprise contacting the AKR1C3 polypeptide with an effective amount of a compound as disclosed herein. In some embodiments, the compound has a structure as set forth herein. In some embodiments, the AKR1C3 polypeptide is present within a subject. In some embodiments, the subject is a human. In some embodiments, the subject is a male and the AKR1C3 polypeptide is present in the prostate of the subject. In some embodiments, the prostate of the subject comprises a tumor, optionally a castrate-resistant tumor.

The presently disclosed subject matter also provides methods for inhibiting undesirable AKR1C3 biological activity in a subject. In some embodiments, the methods comprise administering to the subject an effective amount of a compound as disclosed herein. In some embodiments, the compound has a structure as set forth herein. In some embodiments, the subject is a human. In some embodiments, the subject is a male and the undesirable AKR1C3 biological activity is present in a tumor, optionally a castrate-resistant tumor, present in the prostate of the subject.

The presently disclosed subject matter also provides methods for treating a prostate tumor in a subject. In some embodiments, the method comprising administering the subject a therapeutically effective amount of a compound as disclosed herein. In some embodiments, the compound has one of the following structures:

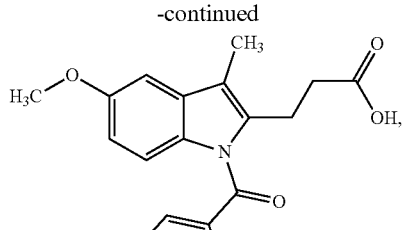

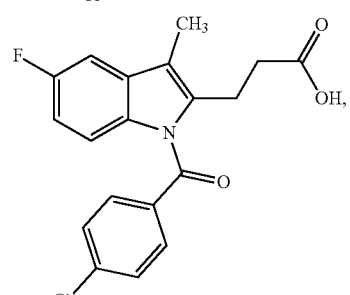

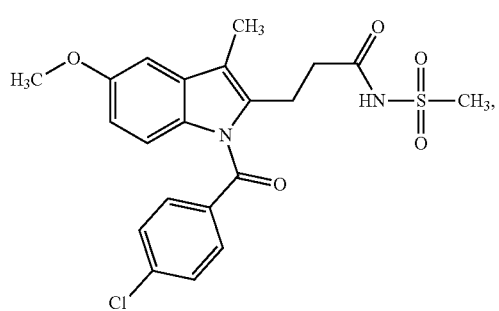

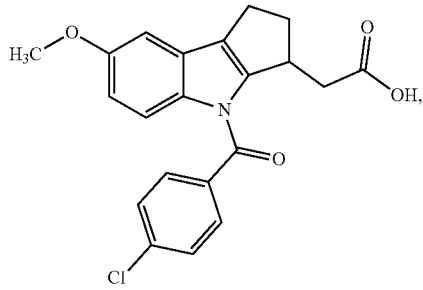

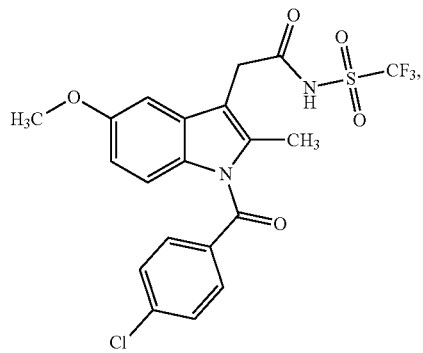

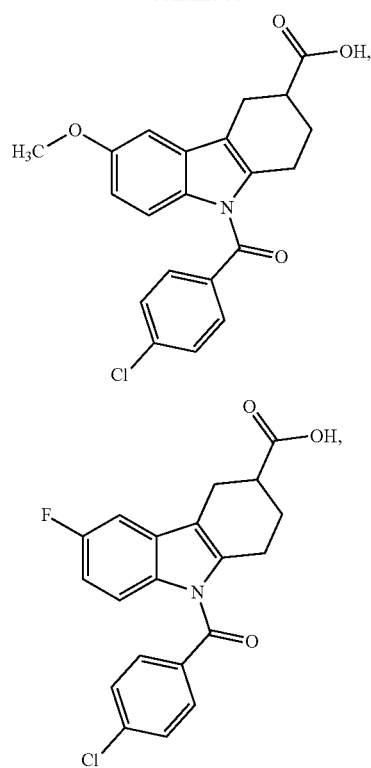
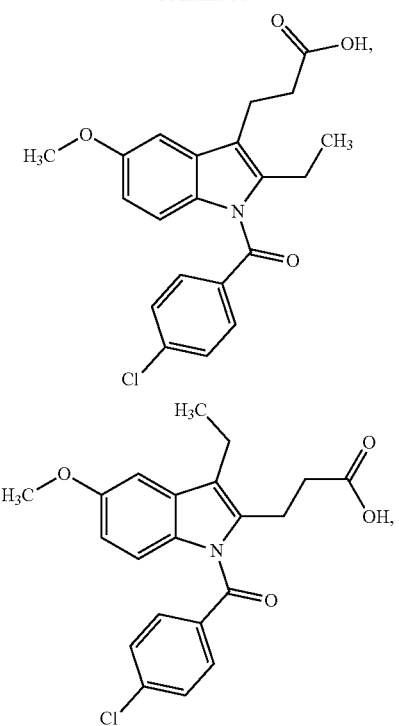
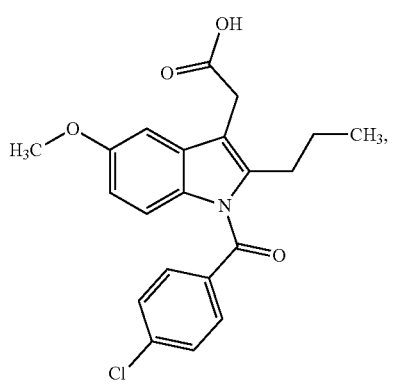
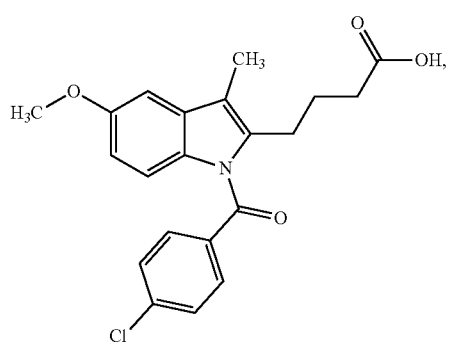
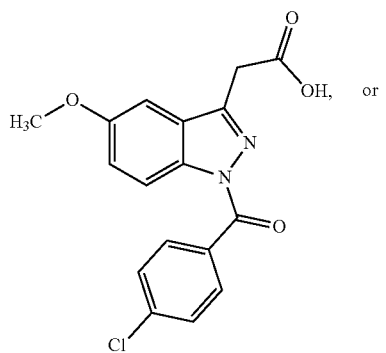

-continued

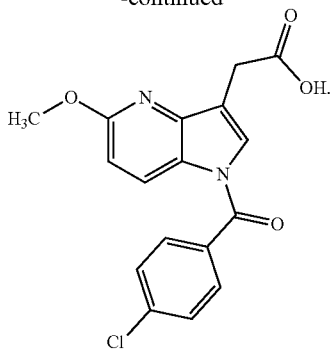

In some embodiments, the prostate tumor is a castrate-resistant prostate tumor. In some embodiments, the administering is via a route selected from the group consisting of peroral, intravenous, intraperitoneal, inhalation, intraprostatic, and intratumoral.

Thus, it is an object of the presently disclosed subject matter to provide compounds that are AKR1C3-specific inhibitors.

An object of the presently disclosed subject matter having been stated hereinabove, and which is achieved in whole or in part by the presently disclosed subject matter, other objects will become evident as the description proceeds when taken in connection with the accompanying Figures as best described herein below.

BRIEF DESCRIPTION OF THE DRAWINGS

FIG. 1A shows how the inhibition of CYP17A1 in the adrenal by abiraterone acetate leads to the buildup of the potent mineralocorticoid desoxycorticosterone, and how the inhibition of AKR1C3 in the prostate by indomethacin and related compounds would block DHT production. FIG. 1B shows the respective roles of AKR1C3 in DHT biosynthesis and the roles of AKR1C1 and AKR1C2 in DHT inactivation within the prostate. HSD3B1=3β-hydroxysteroid dehydrogenase/ketosteroid isomerase (KSI); SRDA5A1 and SRD 5A2 are type 1 and type 2 5α-reductase, respectively; HSD17B6=RoDH like 3β-hydroxysteroid dehydrogenase; AR=androgen receptor, ERβ=estrogen receptorβ.

FIG. 5 depicts an exemplary general synthesis scheme for the AKR1C3-specific inhibitors of the presently disclosed subject matter. In FIG. 5, R13 is H or $C_1$ to $C_6$ alkyl, and q is 0, 1, or 2. With respect to particular embodiments of Formulas I, II, III, and IV, the substitution pattern that is desired can be obtained by selecting the respective ketoacid/ester combinations employed and hence the progression of the Fischer indolization (e.g., "normal" vs. "inverse" cyclization).

FIG. 6 depicts an exemplary synthesis scheme for producing the 2,3,4,9-tetrahydro-1H-carbazole-carboxylic acid derivatives of the presently disclosed subject matter.

FIG. 7 depicts an exemplary synthesis scheme for producing the 2-aza indole derivatives of the presently disclosed subject matter.

FIG. 8 depicts an exemplary synthesis scheme for a microwave-aided method for the synthesis of 4-aza indole derivatives of the presently disclosed subject matter.

FIG. 12A is a control experiment that lacks any inhibitor.

FIGS. 14C and 14D). OS=oxyanion site, SC=steroid cavity, SP=subpocket. Ligand is in black. Two molecules of DM-Indo are bound. One molecule is anchored to Y55 and H117 via its carboxylic acid. The other molecule skirts SP-1 and enters SC. Both binding poses differ from indomethacin.

DETAILED DESCRIPTION

The present subject matter will be now be described more fully hereinafter with reference to the accompanying Examples, in which representative embodiments of the presently disclosed subject matter are shown. The presently disclosed subject matter can, however, be embodied in different forms and should not be construed as limited to the embodiments set forth herein. Rather, these embodiments are provided so that this disclosure will be thorough and complete, and will fully convey the scope of the presently disclosed subject matter to those skilled in the art.

I. General Considerations

All prostate cancers are initially androgen-dependent. Localized prostate cancer is typically treated by radiation therapy, radical prostatectomy, and/or by watchful waiting. Locally invasive or metastatic disease is typically treated by androgen ablation with surgical or chemical castration. The drug of choice for chemical castration is the luteinizing hormone-releasing hormone (LH-RH) agonist Leuprolide acetate (LUPRON). Leuprolide acetate inhibits the release of LH from the anterior pituitary and prevents Leydig cell testosterone biosynthesis. Supplementation of castration with blockade of androgen action in the prostate is common and can be achieved with an androgen receptor (AR) antagonist (e.g., bicalutamide) or by inhibition of type 1 5α-reductase (SRD5A1) and type 2 5α-reductase (SRD5A2) with dutasteride. Bicalutamide is a relatively weak ligand for the AR (Tran et al., 2009).

Figure 1A:
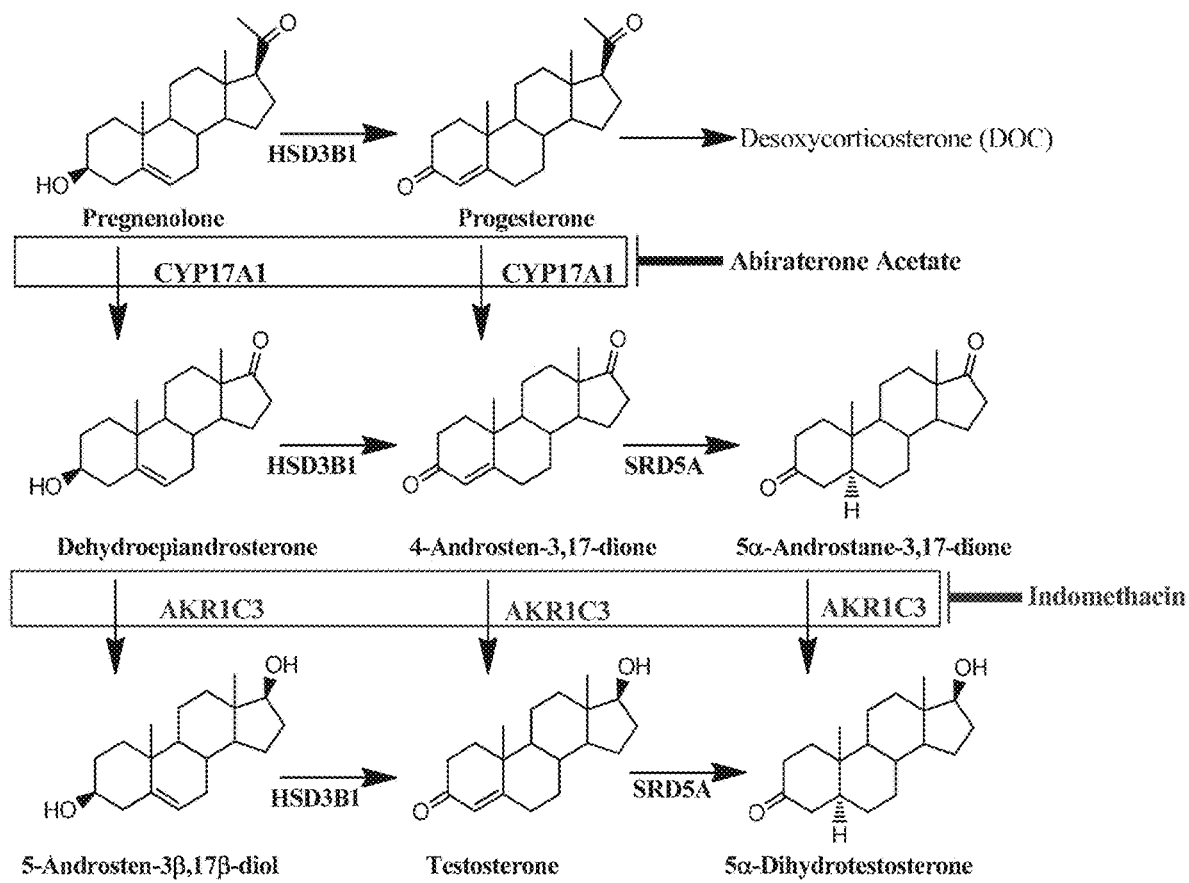
FIGS. 1A and 1B are schematic diagrams of the role of AKR1C3 in the conversion of DHEA to the potent androgens testosterone and 5α-dihydrotestosterone (DHT) in the prostate.
Figure 1B:
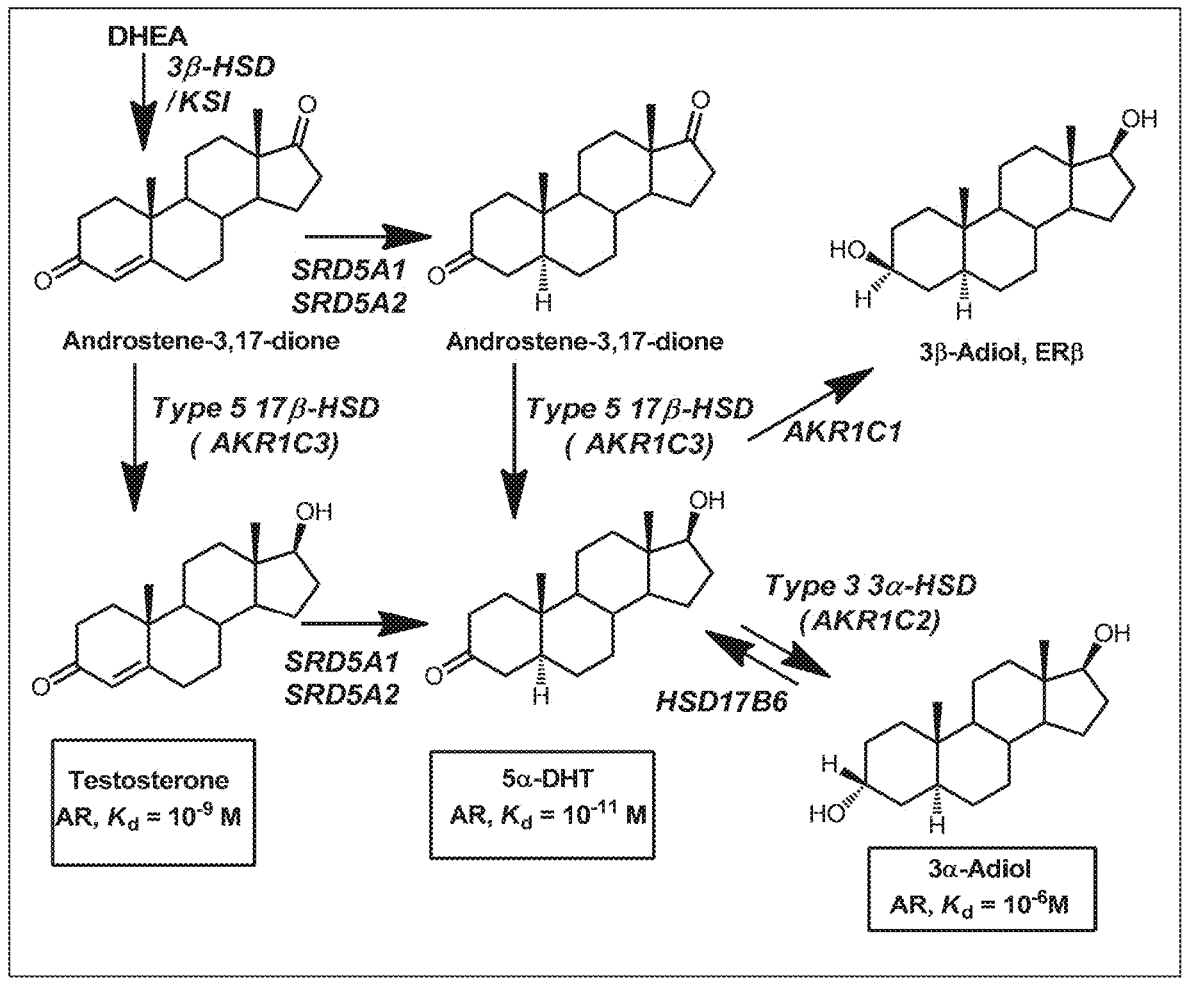
Figure 2A:
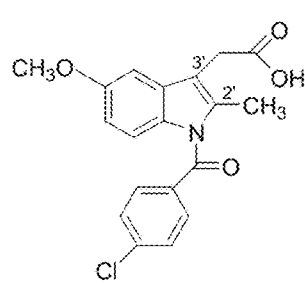
FIGS. 2A and 2B depict structures of exemplary indomethacin derivatives that are AKR1C3-specific inhibitors of the presently disclosed subject matter.
Figure 2A:
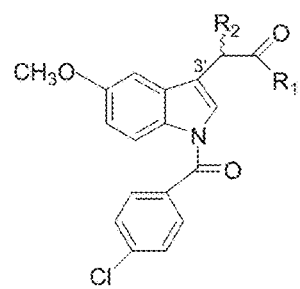
Figure 2A:
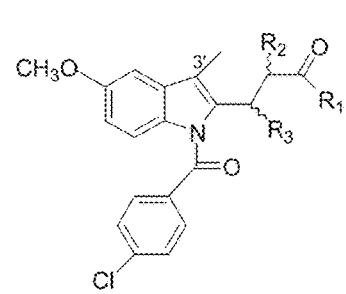
Figure 2A:
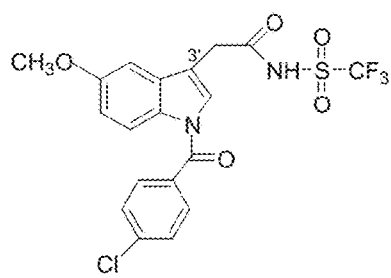
Figure 2A:
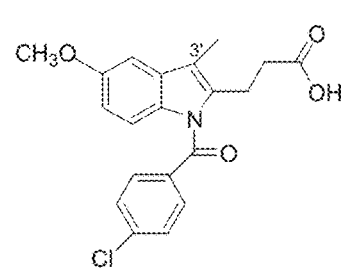
Figure 2A:
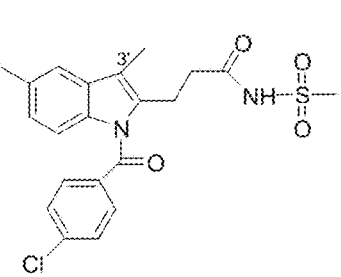
Figure 2B:
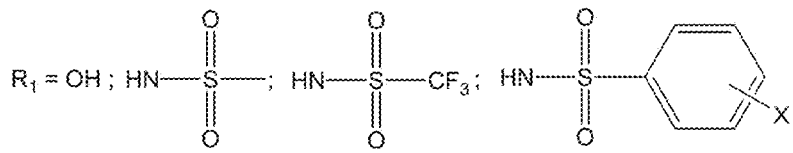
Figure 2B:
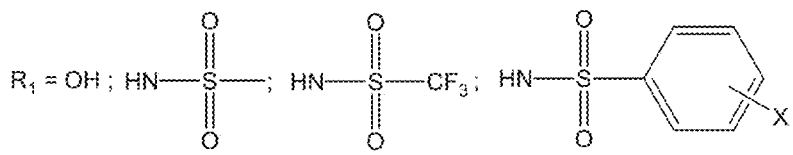

An enzyme responsible for much of the production of testosterone and DHT in the prostate, type 5 17β-hydroxysteroid dehydrogenase (also known as Aldo-Keto Reductase 1C3; AKR1C3) has been identified. This enzyme catalyzes the NADPH-dependent reduction of $\Delta^4$-androstene-3,17-dione (a weak androgen) to form testosterone (a potent androgen), and the NADPH-dependent reduction of 5α-androstane-3,17-dione (a weak androgen) to form DHT (a potent androgen), and plays a central role in androgen biosynthesis (Lin et al., 1997; Penning et al., 2000; Fung et al., 2006; see also FIG. 1). During the development of CRPC, AKR1C3 is among the most highly up-regulated genes in the androgen biosynthetic pathway (Stanbrough et al., 2006; Montgomery et al., 2008).

The use of 5α-reductase inhibitors in the treatment of CRPC has yet to be reported. However, chemoprevention trials of prostate cancer with both finasteride (a selective 5α-reductase type 2 inhibitor) and dutasteride have produced controversial outcomes (Thompson et al., 2007; Andriole et al., 2010; Walsh, 2010). Leuprolide acetate or surgical castration, with or without supplementation with bicalutamide, comprises the mainstay of androgen deprivation therapy (ADT) for prostate cancer. While this is effective at suppressing the growth of metastatic cancer in the short term, the cancer almost invariably reappears.

Tumor reappearance can occur due to adaptive intratumoral androgen synthesis that bypasses the effects of ADT (Attard et al., 2009a). This conclusion is supported by the success of the new drug abiraterone acetate at arresting CRPC and reducing the size of bone metastases in ongoing phase II/III clinical trials (Attard et al., 2009b; Reid et al., 2010). Abiraterone acetate, ZYTIGA® (available from Johnson & Johnson, New Brunswick, N.J., United States of America) is a steroidal P45017α-hydroxylase/17,20-lyase (CYP17) inhibitor that blocks the conversion of pregnenolone to dehydroepiandrosterone (DHEA). It blocks this step in the adrenal, which is the major source of circulating DHEA, or in the prostate if there is de novo steroidogenesis from cholesterol (see FIG. 1A).

A major drawback, however, is that CYP17 is relatively high up in the steroidogenic pathway. Its inhibition in the adrenal diverts pregnenolone to form the mineralocorticoid desoxycorticosterone (DOC). In addition, CYP17 inhibition prevents the formation of cortisol, which via a feedback loop inhibits the production of adrenocorticotropic hormone (ACTH) in the anterior pituitary. The combined effect is elevated DOC production and potentially life-threatening hypertension. Abiraterone is therefore co-administered with a glucocorticoid to suppress the adrenal-anterior pituitary axis. Chronic use of glucocorticoids can lead to drug-induced Cushing's syndrome, immunosuppression, and osteoporosis. A second generation analog of abiraterone acetate is VN/124TOK001, which is both a CYP17 inhibitor and an AR antagonist that targets the receptor for degradation (Vasaitis et al., 2008). This agent is currently in early clinical trials.

Another approach has been to develop an AR antagonist that is more potent than bicalutamide. Bicalutamide has low-affinity for the AR, and thus its effects can be easily surmounted by intratumoral androgen synthesis. MDV3100 (4-(3-(4-cyano-3-(trifluoromethyl)phenyl)-5,5-dimethyl-4-oxo-2-thioxoimidazolidin-1-yl)-2-fluoro-N-methylbenzamide (ENZALUTAMIDE®); Medivation, Inc., San Francisco, Calif., United States of America) is a small molecule AR antagonist that prevents both AR nuclear translocation and binding to DNA and is more potent than bicalutamide (Tran et al., 2009). Phase I/II clinical trials of MDV3100 showed that this agent reduced serum prostate specific antigen (PSA) and circulating tumor cells, and caused radiographic stabilization of the disease (Scher et al., 2010). However, MDV3100 can cause dose-limiting CNS seizures by binding to the $GABA_A$ receptor in the CNS (Foster et al, 2011). To circumvent these problems a new congener is in clinical trial ARN-509 (Clegg et al., 2012). Treatment of CRPC with either abiraterone acetate or MDV3100 can also lead to drug resistance indicating the need for better agents (Efstathiou et al., 2011; Hu et al, 2012 and Mostaghel et al., 2011) None of these approaches targeted AKR1C3, however, the penultimate enzyme involved in androgen biosynthesis in the prostate.

The development of a selective AKR1C3 inhibitor has met with difficulty since AKR1C3 is closely related to AKR1C1 and AKR1C2, which inactivate DHT in the prostate, and their inhibition would be undesirable (Rizner et al., 2003; Steckelbroeck et al., 2004; see also FIG. 1B). Attempts to target AKR1C3 for inhibition have been reported. Compounds include steroid-based inhibitors (e.g., 6-medroxyprogesterone actetate and estrogen-based lactones; see e.g., Qui et al., 2007; Khanim et al., 2009); cyclopentane derivatives (see e.g., Davies et al., 2009; Stefane et al., 2009); benzodiazepine based inhibitors (Usami et al., 2002); and dietary flavones (Krazeisen et al., 2002; Skarydova et al., 2009). None of these competing compounds has been shown to selectively inhibit AKR1C3, and in many instances, they have been shown to bind to other drug targets (e.g., steroid and benzodiazepine receptors).

Astellas Pharma, Inc. of Japan has filed two PCT International Patent Applications for AKR1C3 inhibitors directed to N-sulfonylindole derivatives (PCT International Patent Application Publication No. WO 2007/100066) and benzimidazole derivatives (PCT International Patent Application Publication No. WO 2009/014150). The compositions disclosed are distinct from the compounds disclosed herein. The particular uses disclosed in these two PCT International Patent Applications for the inhibitors relate to treating benign prostatic hyperplasia (BPH) and prostate cancer generally, but CRPC is not described. It is noted that the N-sulfonylindoles disclosed have not been shown to be selective for AKR1C3 in vivo or in vitro. The benzimidazole derivatives disclosed in PCT International Patent Application Publication No. WO 2009/014150 have also not been shown to be selective for AKR1C3 in vivo or in vitro, but were shown to inhibit $\Delta^4$-androstene-3,17-dione-mediated growth of LNCaP cells stably expressing AKR1C3. See also Adeniji et al., 2011.

Certain non-steroidal anti-inflammatory drugs (NSAIDs) inhibit members of the AKR1C family of enzymes. In a NSAID screen it was found that only indomethacin was a selective inhibitor for AKR1C3 over closely related AKR1C isoforms (Byrns et al., 2008). AKR1C3 is thought to be a superior target for CRPC due to the following: (a) it catalyzes the formation of potent androgens, testosterone and 5α-DHT in the prostate and acts downstream from CYP17 (Fung et al., 2006; Penning et al., 2006; Stanbrough et al., 2006); (b) it is highly up-regulated in CRPC (Stanbrough et al., 2006; Montgomery et al., 2008; Mitsiades et al., 2012); and (c) the CRPC phenotype is characterized by elevated transcript levels for AKR1C3 and decreased transcript levels for 5α-reductase type 2, which results in an increased testosterone: 5α-DHT ratio and suggests that testosterone and not 5α-DHT as the driver of CRPC (Montgomery et al., 2008). Regardless, AKR1C3 is necessary for the formation of either androgen within the prostate. As set forth in more detail herein below, the compounds disclosed herein are selective inhibitors for AKR1C3. These compounds differ from the N-phenylanthranilates that have been recently described as selective AKR1C3 inhibitors (Adeniji et al, 2011, 2012).

To elaborate, disclosed herein are the structures of novel indomethacin analogs (see FIGS. 2 and 3) that selectively inhibit AKR1C3 in the nanomolar range, but unlike indomethacin itself, do not inhibit cyclooxygenase (COX) targets of NSAIDs, namely COX-1 or COX-2. The disclosed compounds are potent and selective inhibitors in in vitro drug screens against AKR1C3; they do not inhibit other highly related AKR1C isoforms; they block the conversion of $\Delta^4$-androstene-3,17-dione to testosterone in prostate cancer cells stably transfected with AKR1C3; and they do not act as AR agonists or antagonists in mammalian cell-based reporter gene assays. Indomethacin blocks the $\Delta^4$-androstene-3,17-dione mediated expression of prostate specific antigen (PSA) in VCaP cells (a human androgen dependent castrate resistant prostate cancer cell line) and growth and proliferation of a tumor in a xenograft model of CRPC (Cai et al., 2011). Unique indomethacin analogs disclosed herein are expected to exhibit the same properties as indomethacin in CRPC but without affecting COX-1 or COX-2 activity. Indomethacin is an FDA approved drug, and thus the analogs disclosed herein are expected to have similar absorption, distribution, metabolism, excretion, and toxicity (ADMET) profiles in humans. As such, the compounds disclosed herein and their congeners represent effective agents for the treatment of prostate cancer including, but not limited to CRPC, as well as other diseases and disorders associated with undesirable AKR1C3 biological activities.

II. Definitions

While the following terms are believed to be well understood by one of ordinary skill in the art, the following definitions are set forth to facilitate explanation of the presently disclosed subject matter.

All technical and scientific terms used herein, unless otherwise defined below, are intended to have the same meaning as commonly understood by one of ordinary skill in the art. Mention of techniques employed herein are intended to refer to the techniques as commonly understood in the art, including variations on those techniques or substitutions of equivalent techniques that would be apparent to one of skill in the art. While the following terms are believed to be well understood by one of ordinary skill in the art, the following definitions are set forth to facilitate explanation of the presently disclosed subject matter.

Following long-standing patent law convention, the terms "a", "an", and "the" refer to "one or more" when used in this application, including the claims. Thus, the phrase "a cell" refers to one or more cells, and can thus also refer to a tissue or an organ.

The term "about", as used herein to refer to a measurable value such as an amount of weight, time, dose (e.g., therapeutic dose), etc. is meant to encompass in some embodiments variations of ±20%, in some embodiments ±10%, in some embodiments ±5%, in some embodiments ±1%, in some embodiments ±0.1%, in some embodiments ±0.5%, and in some embodiments ±0.01% from the specified amount, as such variations are appropriate to perform the disclosed methods.

As used herein, the term "and/or" when used in the context of a list of entities, refers to the entities being present singly or in any possible combination or subcombination. Thus, for example, the phrase "A, B, C, and/or D" includes A, B, C, and D individually, but also includes any and all combinations and subcombinations of A, B, C, and D.

As used herein, the term "AKR1C3" refers to an aldo-keto reductase family 1, member C3 (3-alpha dehydrogenase, type II; also referred to as type 5 17β-hydroxysteroid dehydrogenase) gene or gene product. Generally, AKR1C3 gene products catalyze the conversion of aldehydes and ketones to the corresponding alcohols utilizing the cofactors NADH and/or NADPH. More particularly, AKR1C3 gene products catalyze the NADPH-dependent reduction of $\Delta^4$-androstene-3,17-dione to testosterone and the NADPH-dependent reduction of 5-androstane-3,17-dione to DHT. AKR1C3 gene products have been identified in several species, and biosequences corresponding thereto are present in the GENBANK® database. By way of example and not limitation, in some embodiments an AKR1C3 gene product comprises, consists essentially of, and/or consists of a sequence as set forth in Table 1. It is noted that functional characterizations of AKR1C gene products and their biological activities from species other than humans has demonstrated differences among the biological activities of these polypeptides among different species. For example, unlike human AKR1C3, the mouse does not appear to include an AKR1C family member that catalyzes 11β-ketoreduction of prostaglandin (PG) D2. Additionally, mouse prostate appears to lack AKR1C isoforms, unlike humans (see Veliça et al., 2009).

TABLE 1

GENBANK ® Accession Nos. for Exemplary AKR1C3 Biosequences

| Species | Nucleotide Sequence | Amino Acid Sequence |
| --- | --- | --- |
| Homo sapiens | NM_003739 | NP_003730 |
| Macaca mulatta | XM_001118637 | XP_001118637 |
| Pan troglodytes | XM_003312435 | XP_003312483 |
| Pongo abelii | NM_001134068 | NP_001127540 |
| Bos taurus | NM_001038584 | NP_001033673 |
| Canis lupus familiaris | NM_001012344 | NP_001012344 |
| Xenopus (Silurana) tropicalis | NM_001078713 | NP_001072181 |

As used herein, the term "cell" refers not only to the particular subject cell (e.g., a living biological cell), but also to the progeny or potential progeny of such a cell. Because certain modifications can occur in succeeding generations due to either mutation or environmental influences, such progeny cells might not, in fact, be identical to the parent cell, but are still included within the scope of the term as used herein.

The term "comprising", which is synonymous with "including" "containing", or "characterized by", is inclusive or open-ended and does not exclude additional, unrecited elements and/or method steps. "Comprising" is a term of art that means that the named elements and/or steps are present, but that other elements and/or steps can be added and still fall within the scope of the relevant subject matter.

As used herein, the phrase "consisting of" excludes any element, step, or ingredient not specifically recited. For example, when the phrase "consists of" appears in a clause of the body of a claim, rather than immediately following the preamble, it limits only the element set forth in that clause, other elements are not excluded from the claim as a whole.

As used herein, the phrase "consisting essentially of" limits the scope of the related disclosure or claim to the specified materials and/or steps, plus those that do not materially affect the basic and novel characteristic(s) of the disclosed and/or claimed subject matter. For example, a therapeutic method of the presently disclosed subject matter can "consist essentially of" one or more enumerated steps as set forth herein, which means that the one or more enumerated steps produce most or substantially all of the therapeutic benefit intended to be produced by the claimed method. It is noted, however, that additional steps can be encompassed within the scope of such a therapeutic method, provided that the additional steps do not substantially contribute to the therapeutic benefit for which the therapeutic method is intended.

With respect to the terms "comprising", "consisting essentially of", and "consisting of", where one of these three terms is used herein, the presently disclosed and claimed subject matter can include the use of either of the other two terms. For example, the presently disclosed subject matter relates in some embodiments to compositions that comprise the AKR1C3 inhibitors disclosed herein. It is understood that the presently disclosed subject matter thus also encompasses compositions that in some embodiments consist essentially of the AKR1C3 inhibitors disclosed herein, as well as compositions that in some embodiments consist of the AKR1C3 inhibitors disclosed herein. Similarly, it is also understood that in some embodiments the methods of the presently disclosed subject matter comprise the steps that are disclosed herein, in some embodiments the methods of the presently disclosed subject matter consist essentially of the steps that are disclosed, and in some embodiments the methods of the presently disclosed subject matter consist of the steps that are disclosed herein.

As used herein, the term "enzyme" refers to a polypeptide that catalyzes a transformation of a substrate into a product at a rate that is substantially higher than occurs in a non-enzymatic reaction.

As used herein the term "gene" refers to a hereditary unit including a sequence of DNA that occupies a specific location on a chromosome and that contains the genetic instruction for a particular characteristic or trait in an organism.

Similarly, the phrase "gene product" refers to biological molecules that are the transcription and/or translation products of genes. Exemplary gene products include, but are not limited to mRNAs and polypeptides that result from translation of mRNAs. As would be understood by those of ordinary skill, gene products can also be manipulated in vivo or in vitro using well known techniques, and the manipulated derivatives can also be gene products. For example, a cDNA is an enzymatically produced derivative of an RNA molecule (e.g., an mRNA), and a cDNA is considered a gene product. Additionally, polypeptide translation products of mRNAs can be enzymatically fragmented using techniques well known to those of skill in the art, and these peptide fragments are also considered gene products.

As used herein, the term "inhibitor" refers to a chemical substance that inactivates or decreases the biological activity of a polypeptide (e.g., an enzymatic activity). In some embodiments, the polypeptide is an AKR1C3 polypeptide. In some embodiments, the biological activity of the AKR1C3 polypeptide catalyzes the reduction of $\Delta^4$-androstene-3,17-dione to yield testosterone. In some embodiments, the biological activity of the AKR1C3 polypeptide catalyzes the reduction of 5α-androstane-3,17-dione to DHT.

As used herein, the term "interact" includes "binding" interactions and "associations" between molecules. Interactions can be, for example, protein-protein, protein-small molecule, protein-nucleic acid, and nucleic acid-nucleic acid in nature.

As used herein, the term "modulate" refers to an increase, decrease, or other alteration of any, or all, chemical and biological activities or properties of a biochemical entity, e.g., a wild type or mutant polypeptide. As such, the term "modulate" can refer to a change in the expression level of a gene (or a level of RNA molecule or equivalent RNA molecules encoding one or more proteins or protein subunits), or of an activity of one or more proteins or protein subunits, such that expression, level, or activity is greater than or less than that observed in the absence of the modulator. For example, the term "modulate" can mean "inhibit" or "suppress", but the use of the word "modulate" is not limited to this definition.

The term "modulation" as used herein refers to both upregulation (i.e., activation or stimulation) and downregulation (i.e., inhibition or suppression) of a response. Thus, the term "modulation", when used in reference to a functional property or biological activity or process (e.g., enzyme activity or receptor binding), refers to the capacity to upregulate (e.g., activate or stimulate), downregulate (e.g., inhibit or suppress), or otherwise change a quality of such property, activity, or process. In certain instances, such regulation can be contingent on the occurrence of a specific event, such as activation of a signal transduction pathway, and/or can be manifest only in particular cell types.

The term "modulator" refers to a polypeptide, nucleic acid, macromolecule, complex, molecule, small molecule, compound, species, or the like (naturally occurring or non-naturally occurring) that can be capable of causing modulation. Modulators can be evaluated for potential activity as inhibitors or activators (directly or indirectly) of a functional property, biological activity or process, or a combination thereof, (e.g., agonist, partial antagonist, partial agonist, inverse agonist, antagonist, and the like) by inclusion in assays. In such assays, many modulators can be screened at one time. The activity of a modulator can be known, unknown, or partially known.

Modulators can be either selective or non-selective. As used herein, the term "selective" when used in the context of a modulator (e.g., an inhibitor) refers to a measurable or otherwise biologically relevant difference in the way the modulator interacts with one molecule (e.g., an AKR1C3 polypeptide) versus another similar but not identical molecule (e.g., another member of the an AKR family including, but not limited to AKR1C1, AKR1C2, etc.). In some embodiments, compounds that exhibit $IC_{50}$ values in the mid-nanomolar range and are greater than 100 times more potent as inhibitors of AKR1C3 versus other highly related AKR isoforms (e.g., AKR1C1 and AKR1C2) are referred to herein as selective inhibitors.

It must be understood that it is not required that the degree to which the interactions differ be completely opposite. Put another way, the term selective modulator encompasses not only those molecules that only bind to a given polypeptide (e.g., AKR1C3) and not to related family members (e.g., AKR1C1, AKR1C2, etc.). The term is also intended to include modulators that are characterized by interactions with polypeptides of interest and from related family members that differ to a lesser degree. For example, selective modulators include modulators for which conditions can be found (such as the nature of the substituents present on the modulator) that would allow a biologically relevant difference in the binding of the modulator to the polypeptide of interest (e.g., AKR1C3) versus polypeptides derived from different family members (e.g., AKR1C1, AKR1C2, etc.).

When a selective modulator is identified, the modulator will bind to one molecule (for example, AKR1C3) in a manner that is different (for example, stronger) than it binds to another molecule (for example, (e.g., AKR1C1, AKR1C2, etc.). As used herein, the modulator is said to display "selective binding" or "preferential binding" to the molecule to which it binds more strongly.

As used herein, "significance" or "significant" relates to a statistical analysis of the probability that there is a non-random association between two or more entities. To determine whether or not a relationship is "significant" or has "significance", statistical manipulations of the data can be performed to calculate a probability, expressed as a "p-value". Those p-values that fall below a user-defined cutoff point are regarded as significant. For example, a p-value less than or equal to in some embodiments 0.05, in some embodiments less than 0.01, in another example less than 0.005, and in yet another example less than 0.001, are regarded as significant.

As used herein, the term "significant increase" refers to an increase in activity (for example, enzymatic activity) that is larger than the margin of error inherent in the measurement technique, in some embodiments an increase by about 2 fold or greater over a baseline activity (for example, the activity of the wild type enzyme in the presence of an activator), in some embodiments an increase by about 5 fold or greater, and in still some embodiments an increase by about 10 fold or greater.

With respect to the binding of one or more molecules (for example, a modulator) to one or more polypeptides (for example, an AKR1C3 polypeptide), a significant increase can also refer to: (a) a biologically relevant difference in binding of two or more related compounds to the same polypeptide; and/or (b) a biologically relevant difference in binding of the same compound to two different polypeptides. In this aspect, "significant" is to be thought of in its ordinary meaning: namely, a difference between two occurrences that is important (i.e., biologically or medically relevant). By way of example, a significant increase can also refer to an increase in the amount of a derivative of an NSAID (for example, an indomethacin derivative of the presently disclosed subject matter) that interacts with a non-COX polypeptide (for example, an AKR1C3 polypeptide) per unit dose of the derivative administered as compared to the amount of the non-derivatized NSAID (e.g., indomethacin) that interacts with the same non-COX polypeptide per unit dose of the non-derivatized NSAID. In this example, because the derivative binds to COX enzymes less strongly than the parent NSAID, on a mole-for-mole basis, more of the derivative should be available to interact with non-COX polypeptides than would the parent NSAID.

As used herein, the terms "significantly less" and "significantly reduced" refer to a result (for example, an amount of a product of an enzymatic reaction or an extent of binding to a target such as, but not limited to a cyclooxygenase) that is reduced by more than the margin of error inherent in the measurement technique, in some embodiments a decrease by about 2 fold or greater with respect to a baseline activity (for example, the baseline activity of the enzyme in the absence of the inhibitor), in some embodiments, a decrease by about 5 fold or greater, and in still some embodiments a decrease by about 10 fold or greater.

The term "subject" as used herein refers to a member of any invertebrate or vertebrate species. Accordingly, the term "subject" is intended to encompass any member of the Kingdom Animalia including, but not limited to the phylum Chordata (i.e., members of Classes Osteichythyes (bony fish), Amphibia (amphibians), Reptilia (reptiles), Aves (birds), and Mammalia (mammals)), and all Orders and Families encompassed therein.

Similarly, all genes, gene names, and gene products disclosed herein are intended to correspond to orthologs from any species for which the compositions and methods disclosed herein are applicable. Thus, the terms include, but are not limited to genes and gene products from humans and other mammals. It is understood that when a gene or gene product from a particular species is disclosed, this disclosure is intended to be exemplary only, and is not to be interpreted as a limitation unless the context in which it appears clearly indicates. Thus, for example, the genes and/or gene products disclosed herein are intended to encompass homologous genes and gene products from other animals including, but not limited to other mammals, fish, amphibians, reptiles, and birds.

The methods and compositions of the presently disclosed subject matter are particularly useful for warm-blooded vertebrates. Thus, the presently disclosed subject matter concerns mammals (including, but not limited to humans) and birds. More particularly provided is the use of the methods and compositions of the presently disclosed subject matter on mammals such as humans and other primates, as well as those mammals of importance due to being endangered (such as Siberian tigers), of economic importance (animals raised on farms for consumption by humans) and/or social importance (animals kept as pets or in zoos) to humans, for instance, carnivores other than humans (such as cats and dogs), swine (pigs, hogs, and wild boars), ruminants (such as cattle, oxen, sheep, giraffes, deer, goats, bison, and camels), rodents (such as mice, rats, and rabbits), marsupials, and horses. Also provided is the use of the disclosed methods and compositions on birds, including those kinds of birds that are endangered, kept in zoos, as well as fowl, and more particularly domesticated fowl, e.g., poultry, such as turkeys, chickens, ducks, geese, guinea fowl, and the like, as they are also of economic importance to humans. Thus, also provided is the application of the methods and compositions of the presently disclosed subject matter to livestock, including but not limited to domesticated swine (pigs and hogs), ruminants, horses, poultry, and the like.

III. Compositions

In some embodiments, the presently disclosed subject matter provides compounds having one of the following structures:

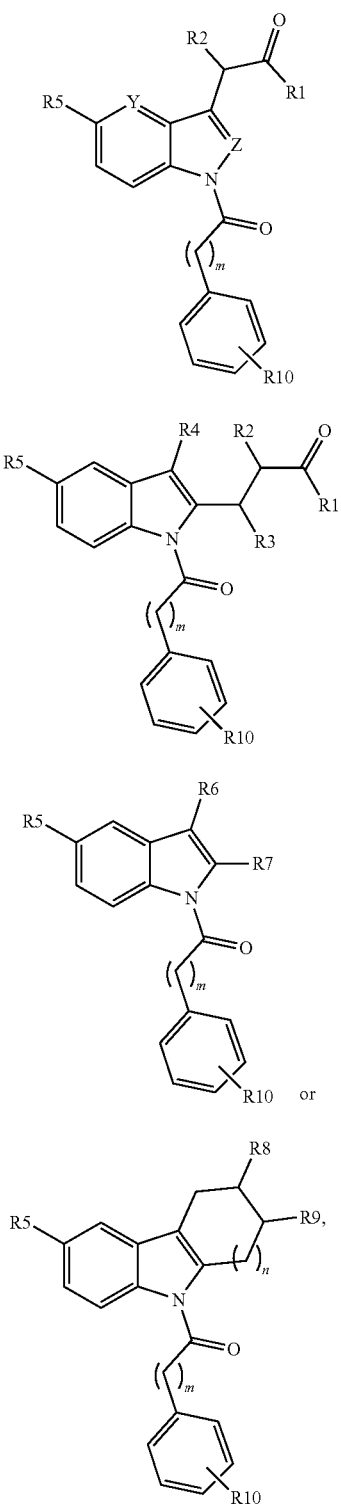

Formula I

Formula II

Formula III

Formula IV wherein R1 is selected from the group consisting of OH, $OCH_3$, $OCH_2CH_3$ and $HNSO_2X$; R2 is hydrogen or R— or S—$C_1$-$C_6$ alkyl; R3 is hydrogen or R— or S—$C_1$-$C_6$ alkyl; R4 is $C_1$ to $C_6$ alkyl; R5 is hydrogen, $C_1$ to $C_6$ alkoxy or halogen; R6 is $C_1$ to $C_6$ alkyl or $C_1$ to $C_6$ alkylcarboxylic acid or $C_1$ to $C_6$ alkyl-C(O)OR12 or $C_1$ to $C_6$ alkyl-C(O)N(H)$SO_2X$; R7 is hydrogen or $C_2$ to $C_6$ alkyl or $C_2$ to $C_6$ alkylcarboxylic acid or $C_2$ to $C_6$ alkyl-C(O)OR12 or $C_2$ to $C_6$ alkyl-C(O)N(H)$SO_2X$; R8 is hydrogen, R- or S-carboxylic acid or C(O)OR12 or C(O)N(H)$SO_2X$; R9 is hydrogen, R- or S-carboxylic acid or C(O)OR12 or C(O)N(H)$SO_2X$; the ring to which R8 or R9 are bound is cyclopentyl or cyclohexyl; R10 is present in two, three, four, or five positions in the phenyl ring and each instance is independently selected from the group consisting of hydrogen, halogen, nitro, $C_1$ to $C_6$ alkyl, singly or multiply halogen substituted $C_1$ to $C_6$ alkyl, $C_1$ to $C_6$ alkoxy, amino, and hydroxy; X is methyl or singly or multiply halogen substituted methyl; phenyl, optionally singly or multiply substituted phenyl or thiophenyl, wherein the single or multiple substitutions of the phenyl or thiophenyl are each independently selected from the group consisting of halogen, nitro, $C_1$ to $C_6$ alkyl, singly or multiply halogen substituted $C_1$ to $C_6$ alkyl, trifluoromethyl, acetyl, isopropyl, $C_1$ to $C_6$ alkoxy, trifluoromethyloxy, phenoxy, cyano, hydroxy, and amino; Y and Z are each individually CH or N; and m and n are each individually 0 or 1.

In particular, non-limiting embodiments, the presently disclosed compounds have one of the following structures:

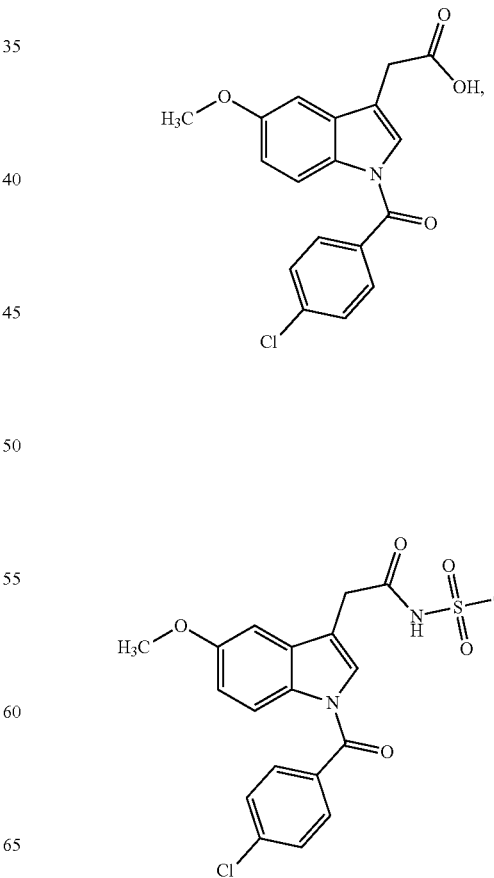

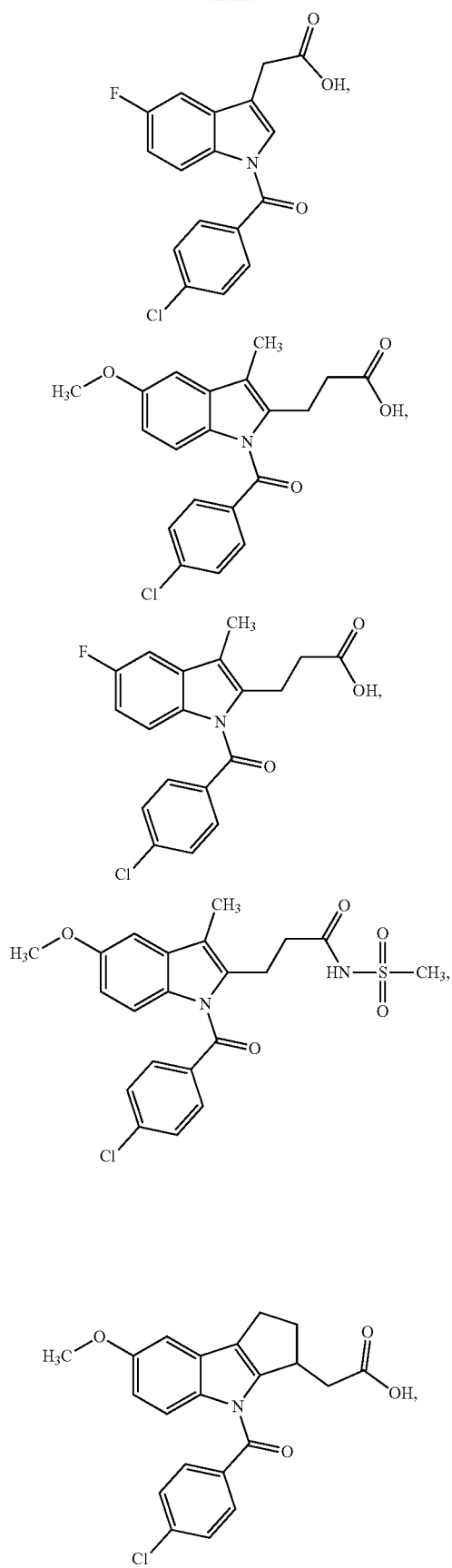
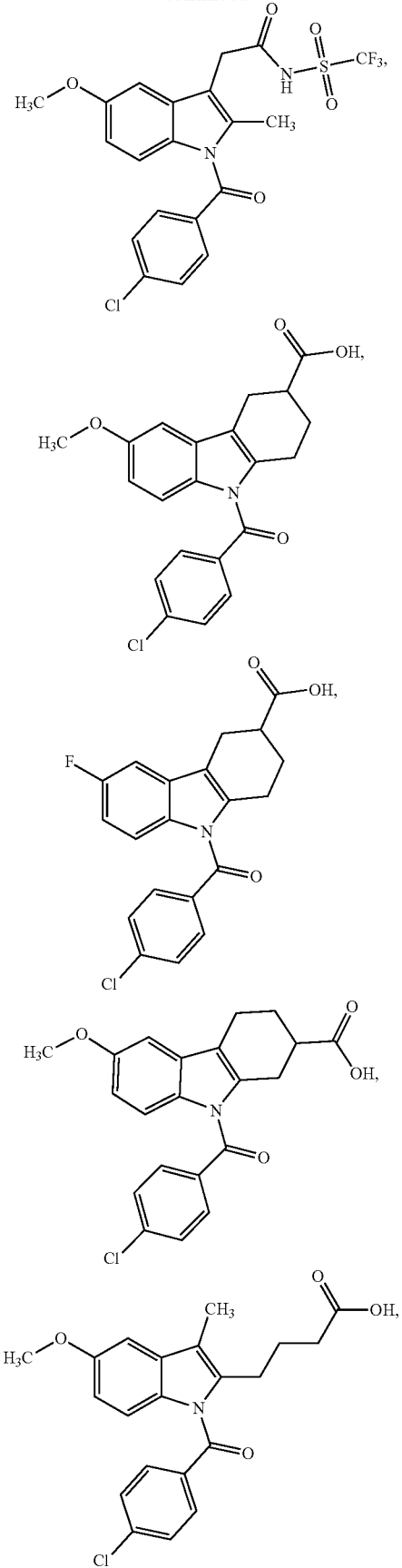

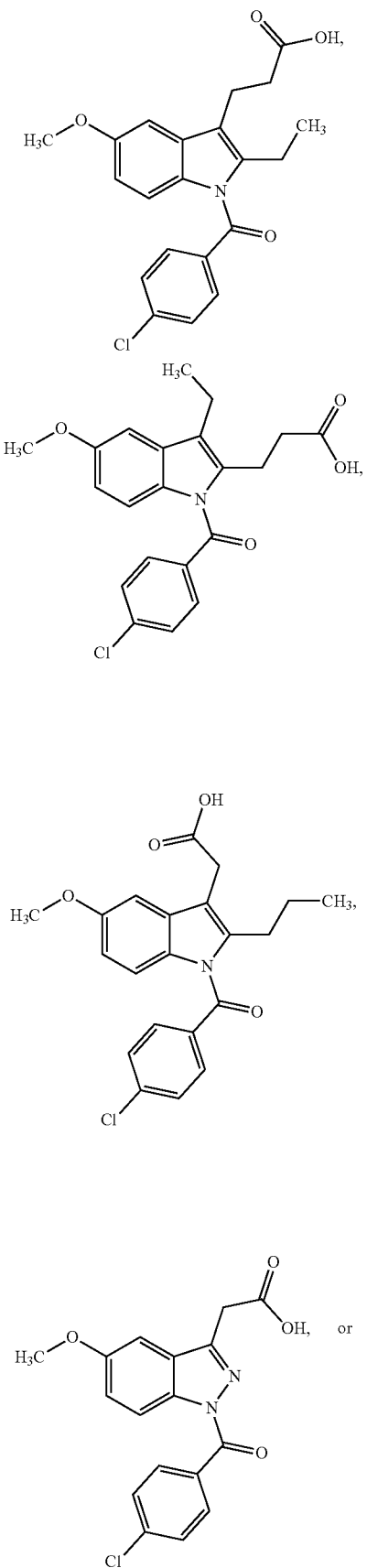

Throughout the specification, drawings, and claims, some structural formulas are depicted without including certain methyl groups and/or hydrogens. In the structural formulas, solid lines represent bonds between two atoms, and unless otherwise indicated, between carbon atoms. Thus, bonds that have no atom specifically recited on one end and/or the other have a carbon atom at that and/or the other end. For example, a structural formula depicted as "—O—" represents C—O—C. Given that hydrogens are not explicitly placed in all structural formulas, implicit hydrogens are understood to exist in the structural formulas as necessary. Thus, a structural formula depicted as "—O" can represent $H_3C$—O, as appropriate given the valences of the particular atoms.

As used herein, the term "alkyl" means in some embodiments $C_{1-10}$ inclusive (i.e. carbon chains comprising 1, 2, 3, 4, 5, 6, 7, 8, 9, or 10 carbon atoms); in some embodiments $C_{1-6}$ inclusive (i.e. carbon chains comprising 1, 2, 3, 4, 5, or 6 carbon atoms); and in some embodiments $C_{1-4}$ inclusive (i.e. carbon chains comprising 1, 2, 3, or 4, carbon atoms) linear, branched, or cyclic, saturated or unsaturated (i.e., alkenyl and alkynyl) hydrocarbon chains, including for example, methyl, ethyl, propyl, isopropyl, butyl, isobutyl, tert-butyl, pentyl, hexyl, ethenyl, propenyl, butenyl, pentenyl, hexenyl, butadienyl, propynyl, butynyl, pentynyl, hexynyl, and allenyl groups.

The alkyl group can be optionally substituted with one or more alkyl group substituents, which can be the same or different, where "alkyl group substituent" includes alkyl, halo, arylamino, acyl, hydroxy, aryloxy, alkoxyl, alkylthio, arylthio, aralkyloxy, aralkylthio, carboxy, alkoxycarbonyl, oxo, and cycloalkyl. In this case, the alkyl can be referred to as a "substituted alkyl". Representative substituted alkyls include, for example, benzyl, trifluoromethyl, and the like. There can be optionally inserted along the alkyl chain one or more oxygen, sulfur or substituted or unsubstituted nitrogen atoms, wherein the nitrogen substituent is hydrogen, alkyl (also referred to herein as "alkylaminoalkyl"), or aryl. Thus, the term "alkyl" can also include esters and amides. "Branched" refers to an alkyl group in which an alkyl group, such as methyl, ethyl, or propyl, is attached to a linear alkyl chain.

The term "aryl" is used herein to refer to an aromatic substituent, which can be a single aromatic ring or multiple aromatic rings that are fused together, linked covalently, or linked to a common group such as a methylene or ethylene moiety. The common linking group can also be a carbonyl as in benzophenone or oxygen as in diphenylether or nitrogen as in diphenylamine. The aromatic ring(s) can include phenyl, naphthyl, biphenyl, diphenylether, diphenylamine, and benzophenone among others. In particular embodiments, the term "aryl" means a cyclic aromatic comprising about 5 to about 10 carbon atoms, including 5 and 6-membered hydrocarbon and heterocyclic aromatic rings.

An aryl group can be optionally substituted with one or more aryl group substituents which can be the same or different, where "aryl group substituent" includes alkyl, aryl, aralkyl, hydroxy, alkoxyl, aryloxy, aralkoxyl, carboxy, acyl, halo, nitro, alkoxycarbonyl, aryloxycarbonyl, aralkoxycarbonyl, acyloxyl, acylamino, aroylamino, carbamoyl, alkylcarbamoyl, dialkylcarbamoyl, arylthio, alkylthio, alkylene and —NR'R", where R' and R" can be each independently hydrogen, alkyl, aryl and aralkyl. In this case, the aryl can be referred to as a "substituted aryl". Also, the term "aryl" can also included esters and amides related to the underlying aryl group.

Specific examples of aryl groups include but are not limited to cyclopentadienyl, phenyl, furan, thiophene, pyrrole, pyran, pyridine, imidazole, isothiazole, isoxazole, pyrazole, pyrazine, pyrimidine, and the like.

The term "alkoxy" is used herein to refer to the —OZ$^1$ radical, where $Z^1$ is selected from the group consisting of alkyl (in some embodiments, $C_1$ to $C_6$ alkyl), substituted alkyl, cycloalkyl, substituted cycloalkyl, heterocycloalkyl, substituted heterocycloalkyl, silyl groups, and combinations thereof as described herein. Suitable alkoxy radicals include, for example, methoxy, ethoxy, benzyloxy, t-butoxy, etc. A related term is "aryloxy" where $Z^1$ is selected from the group consisting of aryl, substituted aryl, heteroaryl, substituted heteroaryl, and combinations thereof. Examples of suitable aryloxy radicals include phenoxy, substituted phenoxy, 2-pyridinoxy, 8-quinalinoxy, and the like.

The term "amino" is used herein to refer to the group —NZ$^1$Z$^2$, where each of $Z^1$ and $Z^2$ is independently selected from the group consisting of hydrogen, alkyl, substituted alkyl, cycloalkyl, substituted cycloalkyl, heterocycloalkyl, substituted heterocycloalkyl, aryl, substituted aryl, heteroaryl, substituted heteroaryl, alkoxy, aryloxy, silyl and combinations thereof. Additionally, the amino group can be represented as N$^+$ $Z^1$ $Z^2$ $Z^3$, with the previous definitions applying and $Z^3$ being either H or alkyl.

As used herein, the term "acyl" refers to an organic acid group wherein the —OH of the carboxyl group has been replaced with another substituent (i.e., as represented by RCO—, wherein R is an alkyl or an aryl group as defined herein). As such, the term "acyl" specifically includes arylacyl groups, such as an acetylfuran and a phenacyl group. Specific examples of acyl groups include acetyl and benzoyl.

"Aroyl" means an aryl-CO— group wherein aryl is as previously described. Exemplary aroyl groups include benzoyl and 1- and 2-naphthoyl.

"Cyclic" and "cycloalkyl" refer to a non-aromatic mono- or multicyclic ring system of about 3 to about 10 carbon atoms, e.g., 3, 4, 5, 6, 7, 8, 9, or 10 carbon atoms. The cycloalkyl group can be optionally partially unsaturated. The cycloalkyl group also can be optionally substituted with an alkyl group substituent as defined herein, oxo, and/or alkylene. There can be optionally inserted along the cyclic alkyl chain one or more oxygen, sulfur or substituted or unsubstituted nitrogen atoms, wherein the nitrogen substituent is hydrogen, lower alkyl, or aryl, thus providing a heterocyclic group. Representative monocyclic cycloalkyl rings include cyclopentyl, cyclohexyl, and cycloheptyl. Multicyclic cycloalkyl rings include adamantyl, octahydronaphthyl, decalin, camphor, camphane, and noradamantyl.

"Aralkyl" refers to an aryl-alkyl- group wherein aryl and alkyl are as previously described. Exemplary aralkyl groups include benzyl, phenylethyl, and naphthylmethyl.

"Aralkyloxyl" refers to an aralkyl-O— group wherein the aralkyl group is as previously described. An exemplary aralkyloxyl group is benzyloxyl.

"Dialkylamino" refers to an —NRR' group wherein each of R and R' is independently an alkyl group as previously described. Exemplary alkylamino groups include ethylmethylamino, dimethylamino, and diethylamino.

"Alkoxycarbonyl" refers to an alkyl-O—CO— group. Exemplary alkoxycarbonyl groups include methoxycarbonyl, ethoxycarbonyl, butyloxycarbonyl, and t-butyloxycarbonyl.

"Aryloxycarbonyl" refers to an aryl-O—CO— group. Exemplary aryloxycarbonyl groups include phenoxy- and naphthoxy-carbonyl.

"Aralkoxycarbonyl" refers to an aralkyl-O—CO— group. An exemplary aralkoxycarbonyl group is benzyloxycarbonyl.

"Carbamoyl" refers to an $H_2N$—CO— group.

"Alkylcarbamoyl" refers to a R'RN—CO— group wherein one of R and R' is hydrogen and the other of R and R' is alkyl as previously described.

"Dialkylcarbamoyl" refers to a R'RN—CO— group wherein each of R and R' is independently alkyl as previously described.

"Acyloxyl" refers to an acyl-O— group wherein acyl is as previously described.

"Acylamino" refers to an acyl-NH— group wherein acyl is as previously described.

"Aroylamino" refers to an aroyl-NH— group wherein aroyl is as previously described.

The term "amino" refers to the —NH$_2$ group.
The term "carbonyl" refers to the —(C=O)— group.
The term "carboxyl" refers to the —COOH group.
The term "hydroxyl" refers to the —OH group.
The term "hydroxyalkyl" refers to an alkyl group substituted with an —OH group.
The term "mercapto" refers to the —SH group.
The term "oxo" refers to a compound described previously herein wherein a carbon atom is replaced by an oxygen atom.
The term "nitro" refers to the —NO$_2$ group.
The term "thio" refers to a compound described herein wherein a carbon or oxygen atom is replaced by a sulfur atom.
The term "sulfate" refers to the —SO$_4$ group.

IV. Exemplary Synthesis Methods

In some embodiments, the presently disclosed subject matter provides methods for producing indomethacin derivatives that substantially lack and/or are devoid of cyclooxygenase inhibitory activity, but which have AKR1C3 inhibitory activity. It is noted that any suitable synthesis scheme can be employed for producing the presently disclosed indomethacin derivatives, and one of ordinary skill in the art will understand what synthesis schemes can be employed based on the formulae disclosed herein (including, but not limited to Formulae I-IV).

Representative synthesis schemes are discussed in more detail herein below in the EXAMPLES and are presented in FIGS. 5-8. It is understood that the representative schemes are non-limiting, and further that the scheme depicted in FIG. 5 as being applicable for synthesizing derivatives of Formula III can also be employed with modifications that would be apparent to one of ordinary skill in the art after review of the instant specification for synthesizing any derivative that falls within the scope of Formula IV.

Figure 6:
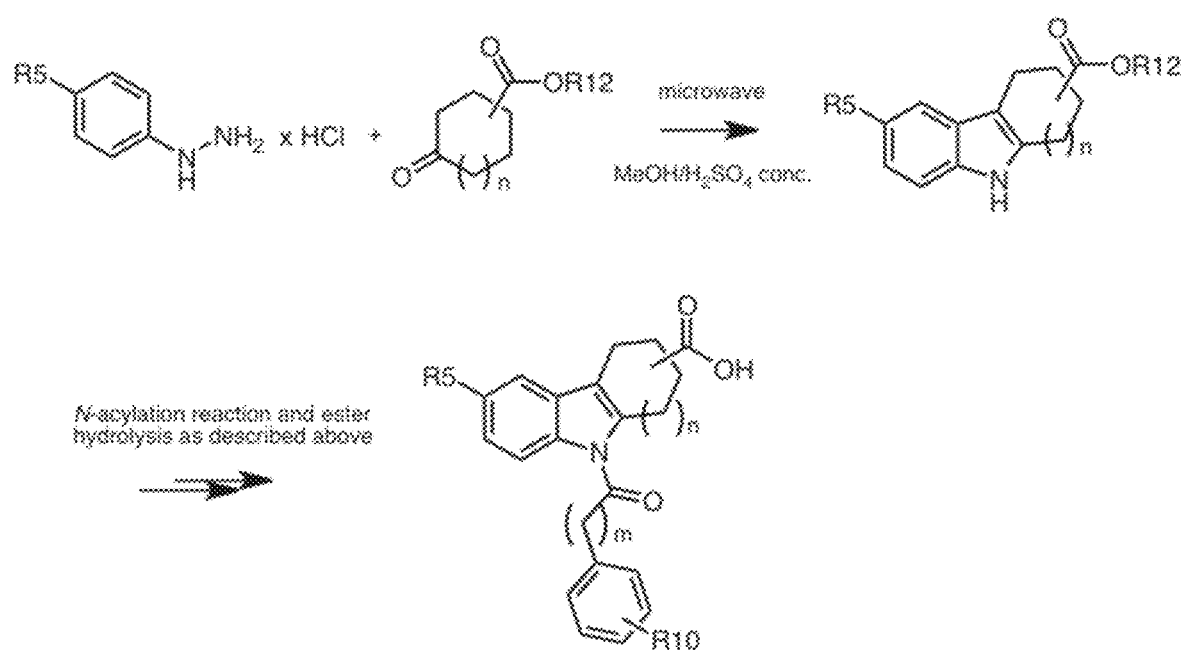

Similarly, the scheme depicted in FIG. 6 as applicable, for example, for synthesizing derivatives of Formula III can also be employed with modifications that would be apparent to one of ordinary skill in the art after review of the instant specification for synthesizing any derivative that falls within the scope of Formula IV. Representative, non-limiting embodiments of the synthesis scheme depicted in FIG. 6 can be found in EXAMPLE 1.

Figure 7:
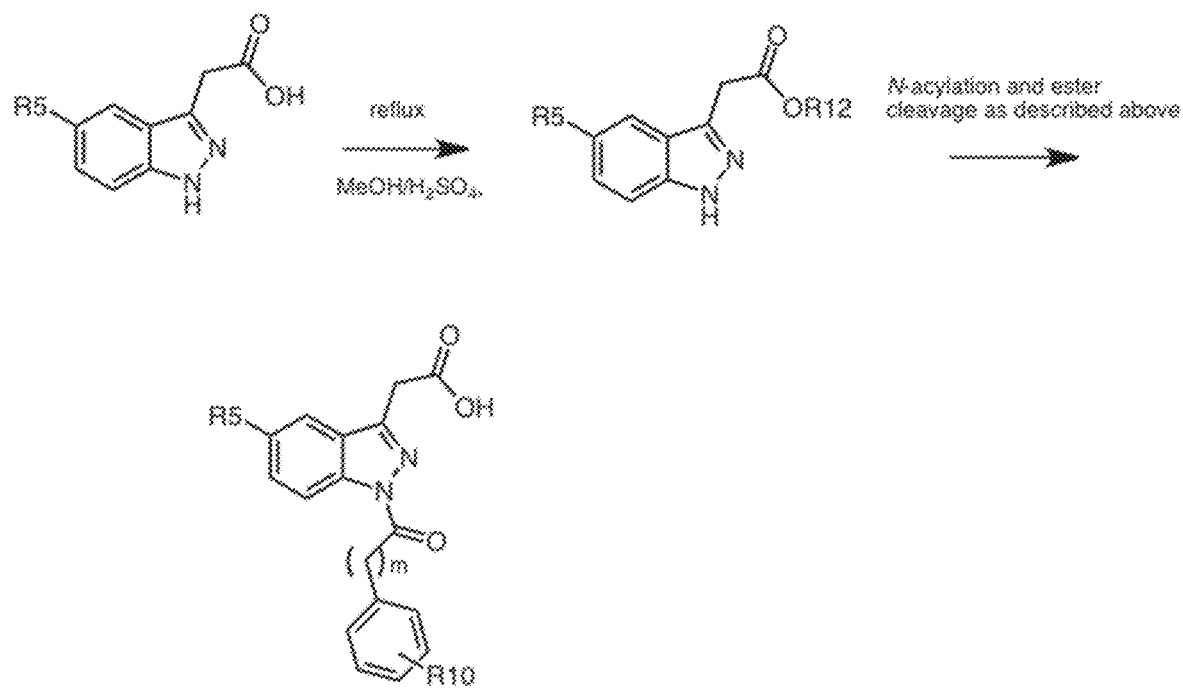

Also similarly, the scheme depicted in FIG. 7 as being applicable for synthesizing particular derivatives of Formula I can also be employed with modifications that would be apparent to one of ordinary skill in the art after review of the instant specification for synthesizing other derivatives that fall within the scope of Formula I, for example by starting with a different starting material and/or reactants. Representative, non-limiting embodiments of the synthesis scheme depicted in FIG. 7 can also be found in EXAMPLE 1.

Figure 8:
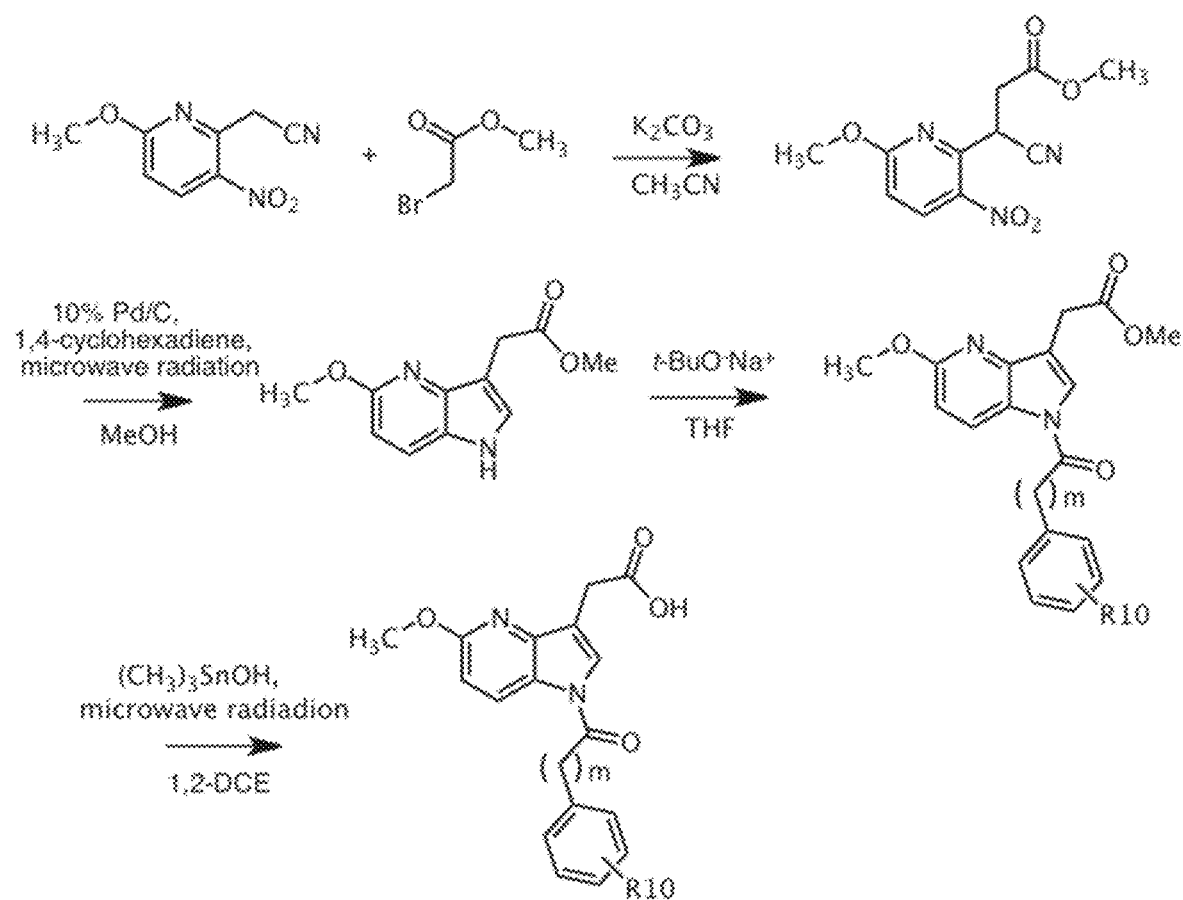

And finally, the exemplary scheme depicted in FIG. 8 can be employed for microwave-aided synthesis of 4-aza indole derivatives of the presently disclosed subject matter. Representative, non-limiting embodiments of the synthesis scheme depicted in FIG. 8 can also be found in EXAMPLE 1.

As such, in some embodiments the presently claimed synthesis methods comprise modifying indomethacin, or a derivative or salt thereof, to produce a compound with one of the following structures:

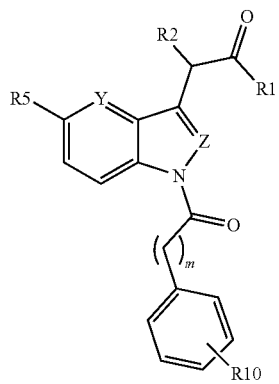

Formula I

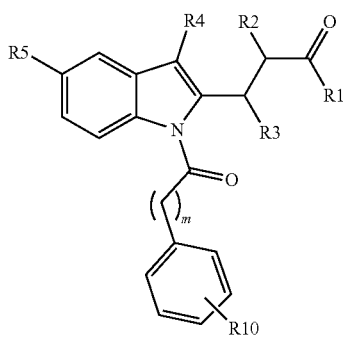

Formula II

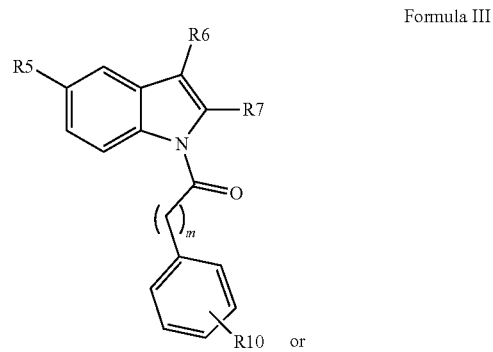

Formula III

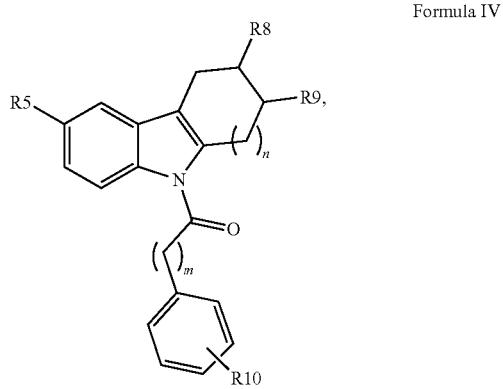

Formula IV wherein R1 is selected from the group consisting of OH, $OCH_3$, $OCH_2CH_3$ and $HNSO_2X$; R2 is hydrogen or R— or S—$C_1$-$C_6$ alkyl; R3 is hydrogen or R— or S—$C_1$-$C_6$ alkyl; R4 is $C_1$ to $C_6$ alkyl; R5 is hydrogen, $C_1$ to $C_6$ alkoxy or halogen; R6 is $C_1$ to $C_6$ alkyl or $C_1$ to $C_6$ alkylcarboxylic acid or $C_1$ to $C_6$ alkyl-C(O)OR12 or $C_1$ to $C_6$ alkyl-C(O)N(H)$SO_2X$; R7 is hydrogen or $C_2$ to $C_6$ alkyl or $C_2$ to $C_6$ alkylcarboxylic acid or $C_2$ to $C_6$ alkyl-C(O)OR12 or $C_2$ to $C_6$ alkyl-C(O)N(H)$SO_2X$; R8 is hydrogen, R- or S-carboxylic acid or C(O)OR12 or C(O)N(H)$SO_2X$; R9 is hydrogen, R- or S-carboxylic acid or C(O)OR12 or C(O)N(H)$SO_2X$; the ring to which R8 or R9 are bound is cyclopentyl or cyclohexyl; R10 is present in two, three, four, or five positions in the phenyl ring and each instance is independently selected from the group consisting of hydrogen, halogen, nitro, $C_1$ to $C_6$ alkyl, singly or multiply halogen substituted $C_1$ to $C_6$ alkyl, $C_1$ to $C_6$ alkoxy, amino, and hydroxy; X is methyl or singly or multiply halogen substituted methyl; phenyl, optionally singly or multiply substituted phenyl or thiophenyl, wherein the single or multiple substitutions of the phenyl or thiophenyl are each independently selected from the group consisting of halogen, nitro, $C_1$ to $C_6$ alkyl, singly or multiply halogen substituted $C_1$ to $C_6$ alkyl, trifluoromethyl, acetyl, isopropyl, $C_1$ to $C_6$ alkoxy, trifluoromethyloxy, phenoxy, cyano, hydroxy, and amino; Y and Z are each individually CH or N; and m and n are each individually 0 or 1.

In some embodiments, the compound thereby produced has one of the following structures:
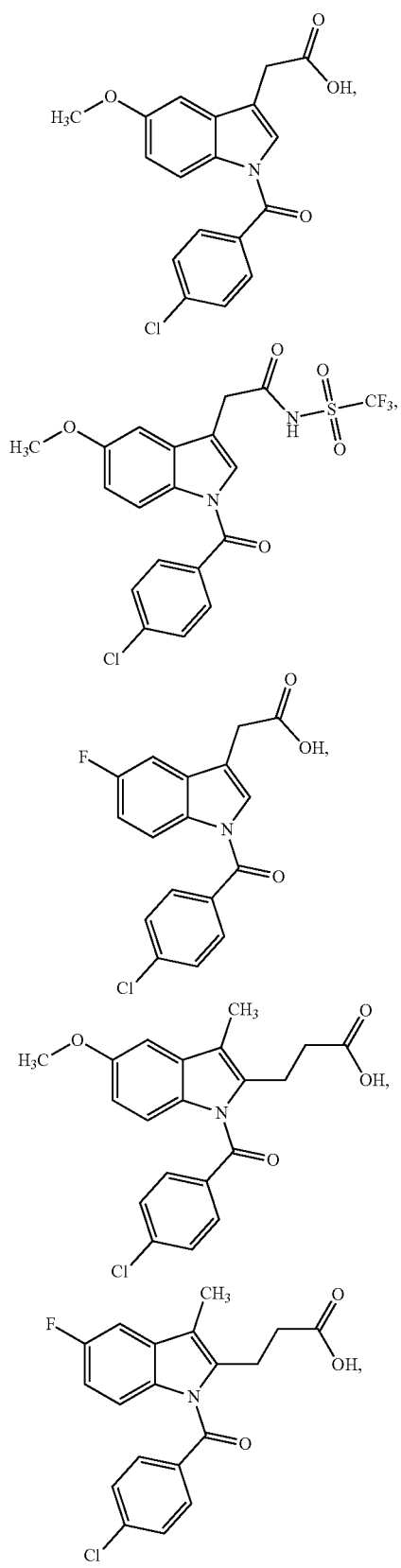
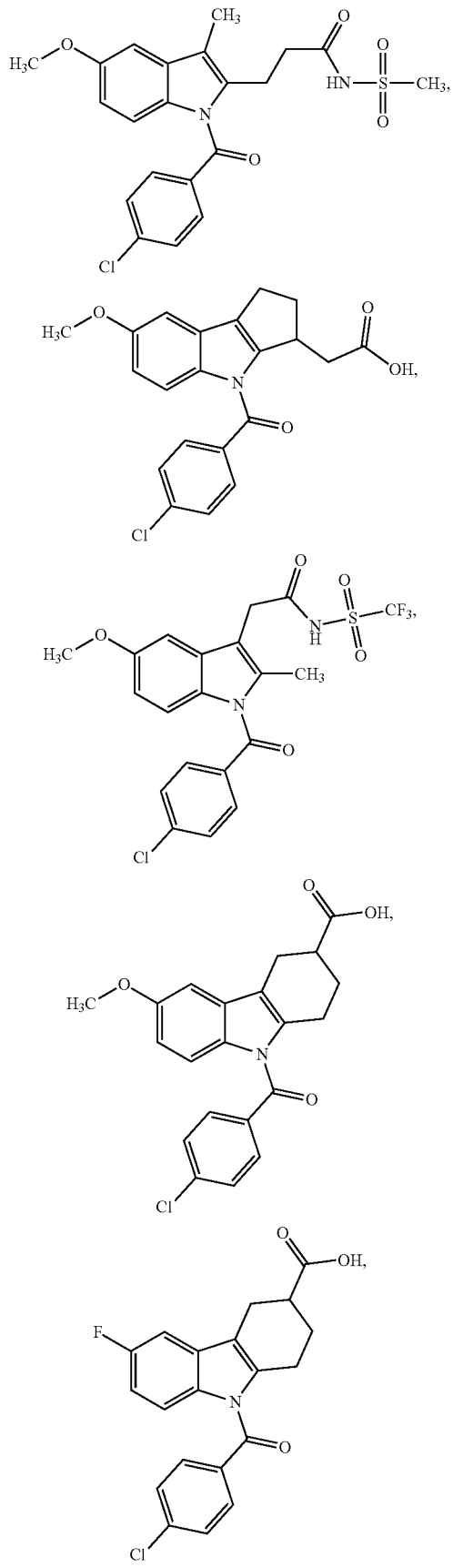 [SMILES: COc1ccc2c(c1)c(C)c(CCC(=O)NS(C)(=O)=O)n2C(=O)c1ccc(Cl)cc1 ; COc1ccc2c(c1)c1c(n2C(=O)c2ccc(Cl)cc2)C(CC(=O)O)CC1 ; COc1ccc2c(c1)c(CC(=O)NS(=O)(=O)C(F)(F)F)c(C)n2C(=O)c1ccc(Cl)cc1 ; COc1ccc2c(c1)c1c(n2C(=O)c2ccc(Cl)cc2)CCC(C(=O)O)C1 ; O=C(O)C1CCc2c(c3cc(F)ccc3n2C(=O)c2ccc(Cl)cc2)C1]
-continued

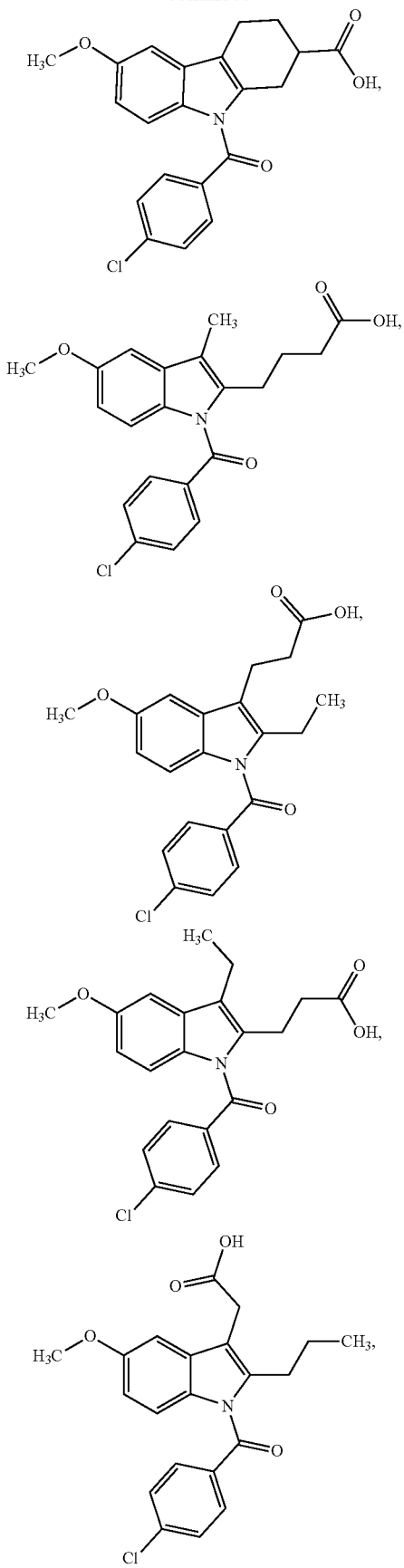

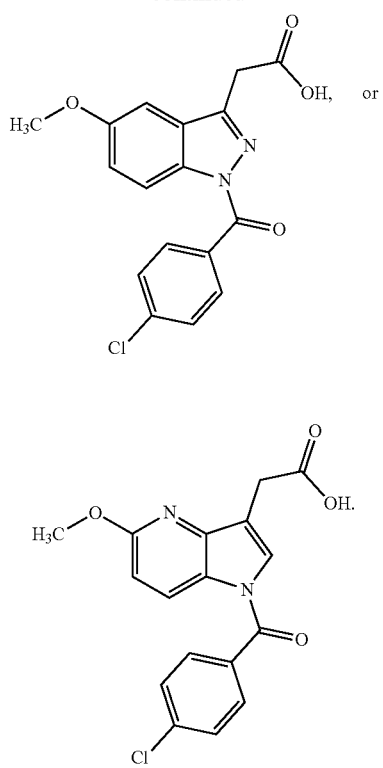

In some embodiments, the presently disclosed subject matter also provides methods for producing indomethacin derivatives that substantially lack and/or are devoid of cyclooxygenase inhibitory activity but which have AKR1C3 inhibitory activity that comprise performing a microwave-assisted reaction between (a) an alkoxy- or halo-substituted phenylhydrazine or a salt thereof and (b) a cyclic or acyclic aliphatic ketoacid or alkyl ester thereof thereby providing an indole alkyl carboxylic acid or ester thereof, wherein the indole alkyl carboxylic acid or ester is a synthetic precursor of the indomethacin derivative. In some embodiments, the microwave-assisted reaction is performed in the presence of sulfuric acid. In some embodiments, the microwave-assisted reaction is performed in an alcoholic solvent, which in some embodiments is methanol, ethanol, or acetic acid.

In some embodiments, the $C_1$ to $C_6$ alkoxy- or halo-substituted phenylhydrazine or the salt thereof that is employed in the reaction is a compound of Formula V:

Formula V

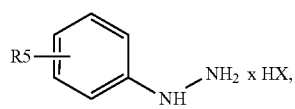

wherein R5 is hydrogen, $C_1$ to $C_6$ alkoxy or halogen and X is halogen, optionally Cl.

In some embodiments, the cyclic or acyclic aliphatic ketoacid or alkyl ester thereof that is employed in the reaction is a compound of Formula VI or a compound of Formula VII, wherein Formula VI and Formula VII have the following structures:

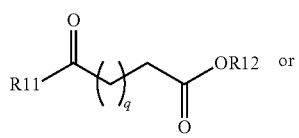

Formula VI

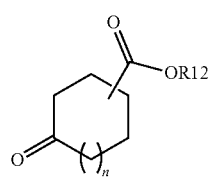

Formula VII wherein R11 is $C_1$-$C_6$ alkyl; R12 is H, methyl or ethyl; q is an integer from 0 to 2; and n is 0 or 1.

In some embodiments, the cyclic or acyclic aliphatic ketoacid or alkyl ester thereof is selected from the group consisting of 3-oxopentanoic acid, 4-oxobutanoic acid, 4-oxopentanoic acid, 5-oxohexanoic acid, 4-oxohexanoic acid, 4-oxoheptanoic acid, 4-oxocyclohexanecarboxylic acid, 3-oxocyclohexanecarboxylic acid or a methyl or ethyl ester thereof.

In some embodiments, the indole alkyl carboxylic acid or ester has a structure of Formula VIII or of Formula IX:

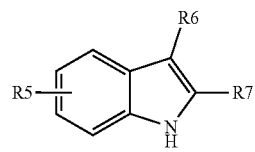

Formula VIII

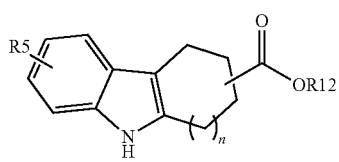

Formula IX wherein R5 is hydrogen, $C_1$ to $C_6$ alkoxy or halogen; R6 is $C_1$ to $C_6$ alkyl or $C_1$ to $C_6$ alkylcarboxylic acid or $C_1$ to $C_6$ alkyl-C(O)O$R_{12}$; R7 is $C_2$ to $C_6$ alkylcarboxylic acid or $C_2$ to $C_6$ alkyl-C(O)OR12; R12 is H, methyl or ethyl; and n is 0 or 1.

In some embodiments, the instant synthesis methods further comprise reacting an indole alkyl carboxylic acid or ester thereof with an aliphatic or aromatic acid halide to introduce an acyl substituent at the indole nitrogen atom, thereby producing an N-acylated indole alkyl carboxylic acid or ester thereof. In some embodiments, the reacting step comprises contacting the indole alkyl carboxylic acid or ester with an alkoxide, preferably sodium or potassium tert-butoxide, thereby deprotonating the indole nitrogen atom; and contacting the deprotonated indole alkyl carboxylic acid or ester with the aliphatic or aromatic acid halide. In some embodiments, one or both of the contacting steps are performed in tetrahydrofuran (THF). In some embodi-ments, the aliphatic or aromatic acid halide is an acid chloride, optionally wherein the acid chloride is selected from the group consisting of 4-chlorobenzoyl chloride, 4-fluorobenzoyl chloride, 3-(trifluoromethyl)benzoyl chloride, 4-(trifluoromethyl)benzoyl chloride, 4-methoxybenzoyl chloride, 4-methylbenzoyl chloride. 4-(chloromethyl)benzoyl chloride, and 2-(4-chlorophenylacetylchloride.

In some embodiments, the instant synthesis methods further comprise hydrolyzing an ester group in an N-acylated indole alkyl carboxylic ester to produce an N-acylated indole alkyl carboxylic acid. In some embodiments, the hydrolyzing step comprises using trimethyltin hydroxide and microwave radiation. In some embodiments, the hydrolyzing step is performed using 1,2-dichloroethane as a solvent.

V. Methods for Modulating AKR1C3 Polypeptide Biological Activities

Also provided herein are methods for using the disclosed AKR1C3 inhibitors to modulate AKR1C3 polypeptide biological activities. In some embodiments, the methods comprise contacting the AKR1C3 polypeptide with an effective amount of a compound as disclosed herein including, but not limited to those disclosed herein above in Section IV.

The methods disclosed herein for using the disclosed AKR1C3 inhibitors to modulate, optionally inhibit, AKR1C3 polypeptide biological activities can be used for in vivo, ex vivo, and/or in vitro modulation, optionally inhibition, of AKR1C3 polypeptide biological activities. As such, in some embodiments the AKR1C3 polypeptide is present within a subject, optionally wherein the subject is a mammal, including but not limited to a human.

In some embodiments, the presently disclosed methods relate to modulating an AKR1C3 polypeptide biological activity that is associated with a prostate tumor or cancer, or a pre-cancerous condition thereof. As such, in some embodiments the subject is a male and the AKR1C3 polypeptide is present in the prostate of the subject. In some embodiments, the prostate of the subject comprises a tumor, optionally a castrate-resistant tumor.

As such, in some embodiments the presently disclosed subject matter provides methods for inhibiting undesirable AKR1C3 polypeptide biological activity in a subject by administering to the subject an effective amount of a compound as disclosed herein. As with the presently disclosed methods for modulating AKR1C3 polypeptide biological activities generally, in some embodiments the instant methods are applicable to subjects that are mammals, including but not limited to subjects that are humans. Thus, in some embodiments the subject is a male and the undesirable AKR1C3 biological activity is present in a tumor, optionally a castrate-resistant tumor, present in the prostate of the subject.

Therefore, in some embodiments the presently disclosed subject matter also relates to methods for treating prostate tumors and/or cancers, optionally a castrate-resistant prostate tumor, in a subject comprising administering to the subject a therapeutically effective amount of an AKR1C3 inhibitor disclosed herein.

In some embodiments, the AKR1C3 inhibitor has a structure as set forth in one of Formulae I-IV below.

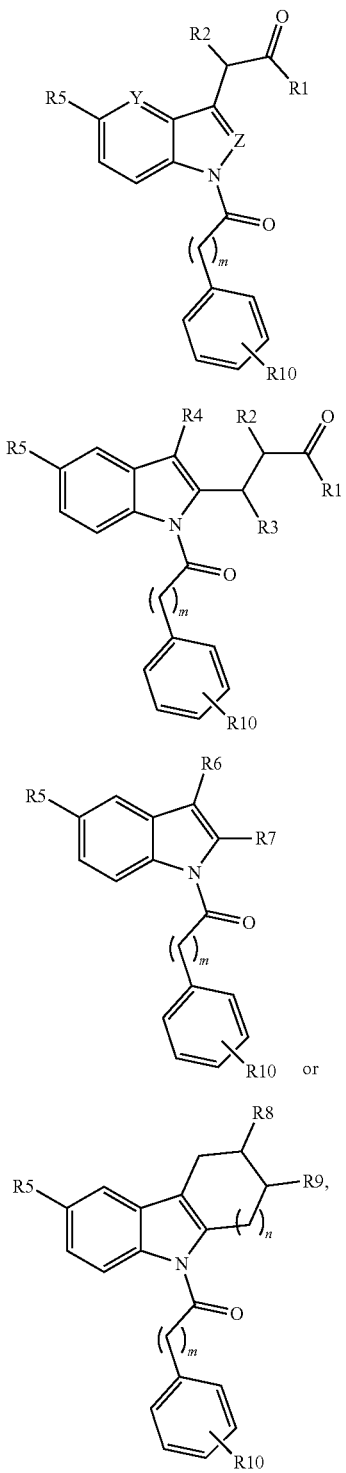

Formula I

Formula II

Formula III

Formula IV wherein R1 is selected from the group consisting of OH, OCH$_3$, OCH$_2$CH$_3$ and HNSO$_2$X; R2 is hydrogen or R— or S—C$_1$-C$_6$ alkyl; R3 is hydrogen or R— or S—C$_1$-C$_6$ alkyl; R4 is C$_1$ to C$_6$ alkyl; R5 is hydrogen, C$_1$ to C$_6$ alkoxy or halogen; R6 is C$_1$ to C$_6$ alkyl or C$_1$ to C$_6$ alkylcarboxylic acid or C$_1$ to C$_6$ alkyl-C(O)OR$_{12}$ or C$_1$ to C$_6$ alkyl-C(O)N(H)SO$_2$X; R7 is hydrogen or C$_2$ to C$_6$ alkyl or C$_2$ to C$_6$ alkylcarboxylic acid or C$_2$ to C$_6$ alkyl-C(O)OR$_{12}$ or C$_2$ to C$_6$ alkyl-C(O)N(H)SO$_2$X; R8 is hydrogen, R- or S-carboxylic acid or C(O)OR$_{12}$ or C(O)N(H)SO$_2$X; R9 is hydrogen, R- or S-carboxylic acid or C(O)OR$_{12}$ or C(O)N(H)SO$_2$X; the ring to which R8 or R9 are bound is cyclopentyl or cyclohexyl; R10 is present in two, three, four, or five positions in the phenyl ring and each instance is independently selected from the group consisting of hydrogen, halogen, nitro, C$_1$ to C$_6$ alkyl, singly or multiply halogen substituted C$_1$ to C$_6$ alkyl, C$_1$ to C$_6$ alkoxy, amino, and hydroxy; X is methyl or singly or multiply halogen substituted methyl; phenyl, optionally singly or multiply substituted phenyl or thiophenyl, wherein the single or multiple substitutions of the phenyl or thiophenyl are each independently selected from the group consisting of halogen, nitro, C$_1$ to C$_6$ alkyl, singly or multiply halogen substituted C$_1$ to C$_6$ alkyl, trifluoromethyl, acetyl, isopropyl, C$_1$ to C$_6$ alkoxy, trifluoromethyloxy, phenoxy, cyano, hydroxy, and amino; Y and Z are each individually CH or N; and m and n are each individually 0 or 1.

In some embodiments, the AKR1C3 inhibitor has one of the following structures:

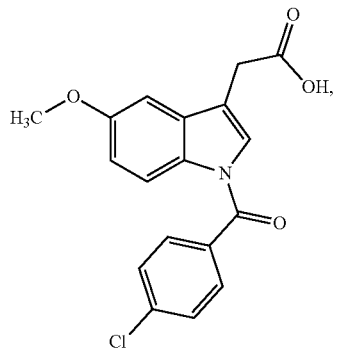

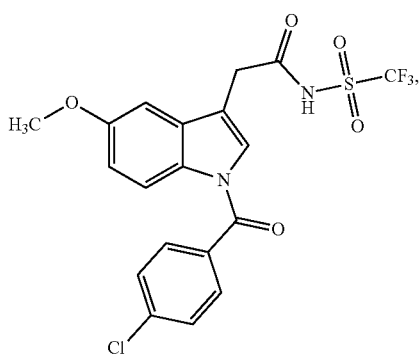

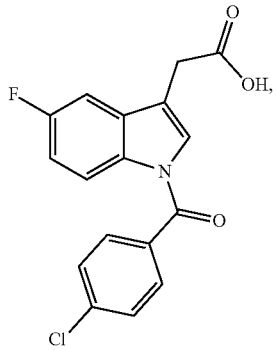

45
-continued
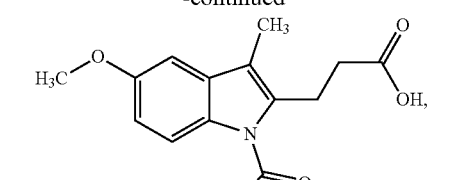
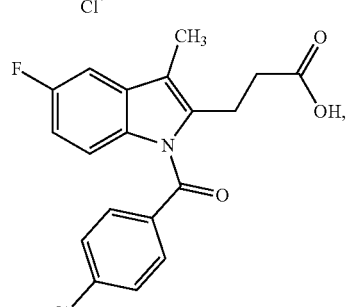
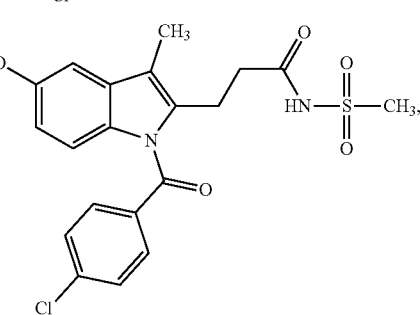
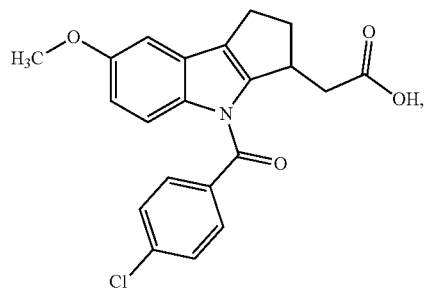
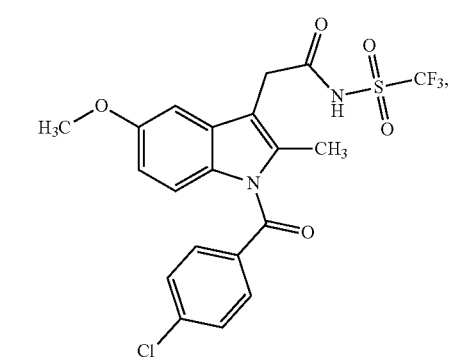
46
-continued
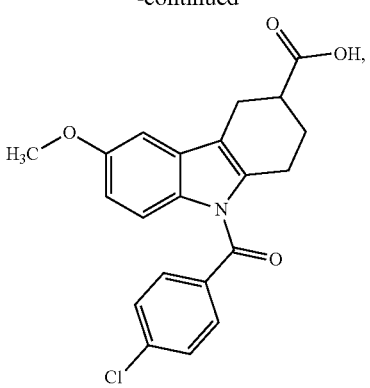
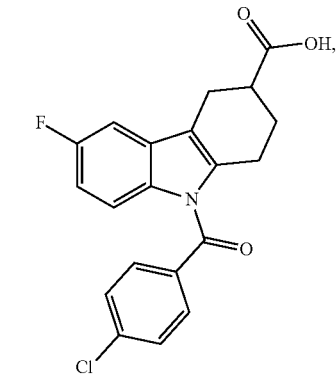
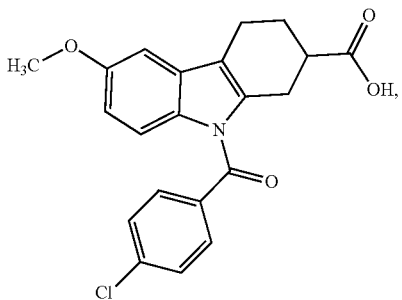

-continued

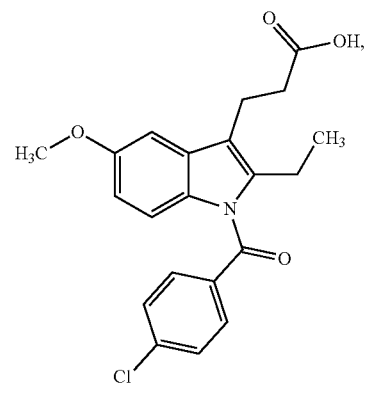

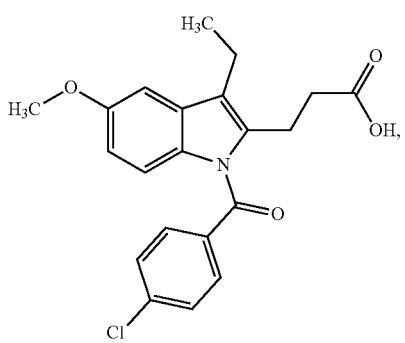

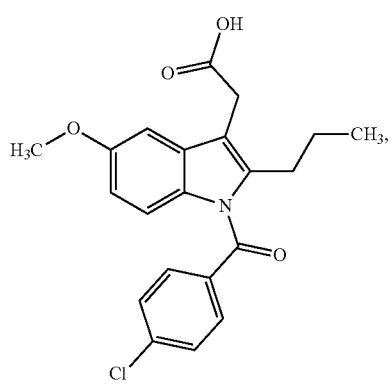

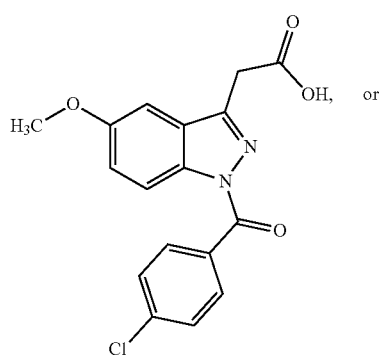

or

-continued

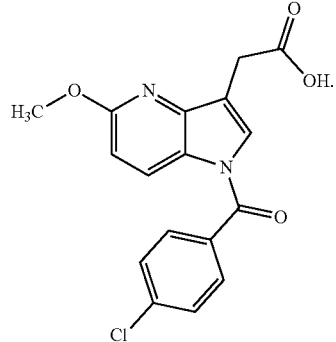

V.A. Formulations

An AKR1C3 inhibitor composition as described herein comprises in some embodiments a composition that includes a pharmaceutically acceptable carrier. Suitable formulations include aqueous and non-aqueous sterile injection solutions that can contain antioxidants, buffers, bacteriostats, bactericidal antibiotics, and solutes that render the formulation isotonic with the bodily fluids of the intended recipient; and aqueous and non-aqueous sterile suspensions, which can include suspending agents and thickening agents.

The compositions used in the methods can take such forms as suspensions, solutions, or emulsions in oily or aqueous vehicles, and can contain formulatory agents such as suspending, stabilizing, and/or dispersing agents. The compositions used in the methods can take forms including, but not limited to peroral, intravenous, intraperitoneal, inhalation, intraprostatic, and intratumoral formulations. Alternatively or in addition, the active ingredient can be in powder form for constitution with a suitable vehicle (e.g., sterile pyrogen-free water) before use.

The formulations can be presented in unit-dose or multi-dose containers, for example sealed ampules and vials, and can be stored in a frozen or freeze-dried (lyophilized) condition requiring only the addition of sterile liquid carrier immediately prior to use.

For oral administration, the compositions can take the form of, for example, tablets or capsules prepared by a conventional technique with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycollate); or wetting agents (e.g., sodium lauryl sulfate). The tablets can be coated by methods known in the art. For example, a neuroactive steroid can be formulated in combination with hydrochlorothiazide, and as a pH stabilized core having an enteric or delayed-release coating which protects the neuroactive steroid until it reaches the colon.

Liquid preparations for oral administration can take the form of, for example, solutions, syrups or suspensions, or they can be presented as a dry product for constitution with water or other suitable vehicle before use. Such liquid preparations can be prepared by conventional techniques with pharmaceutically acceptable additives such as suspending agents (e.g., sorbitol syrup, cellulose derivatives or hydrogenated edible fats); emulsifying agents (e.g. lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations can also contain buffer salts, flavoring, coloring, and sweetening agents as appropriate. Preparations for oral administration can be suitably formulated to give controlled release of the active compound. For buccal administration the compositions can take the form of tablets or lozenges formulated in conventional manner.

The compounds can also be formulated as a preparation for implantation or injection. Thus, for example, the compounds can be formulated with suitable polymeric or hydrophobic materials (e.g., as an emulsion in an acceptable oil) or ion exchange resins, or as sparingly soluble derivatives (e.g., as a sparingly soluble salt).

The compounds can also be formulated in rectal compositions (e.g., suppositories or retention enemas containing conventional suppository bases such as cocoa butter or other glycerides), creams or lotions, or transdermal patches.

In some embodiments, the presently disclosed subject matter employs an AKR1C3 inhibitor composition that is pharmaceutically acceptable for use in humans. One of ordinary skill in the art understands the nature of those components that can be present in an AKR1C3 inhibitor composition that is pharmaceutically acceptable for use in humans and also what components should be excluded from an AKR1C3 inhibitor composition that is pharmaceutically acceptable for use in humans.

V.B. Doses

As used herein, the phrases "treatment effective amount", "therapeutically effective amount", "treatment amount", and "effective amount" are used interchangeably and refer to an amount of a therapeutic composition sufficient to produce a measurable response (e.g., a biologically or clinically relevant response in a subject being treated). Actual dosage levels of active ingredients in the pharmaceutical compositions of the presently disclosed subject matter can be varied so as to administer an amount of the active compound(s) that is effective to achieve the desired therapeutic response for a particular subject. The selected dosage level can depend upon the activity of the therapeutic composition, the route of administration, combination with other drugs or treatments, the severity of the condition being treated, the condition and prior medical history of the subject being treated, etc. However, it is within the skill of the art to start doses of the compound at levels lower than required to achieve the desired therapeutic effect and to gradually increase the dosage until the desired effect is achieved.

The potency of a therapeutic composition can vary, and therefore a "therapeutically effective amount" can vary. However, one skilled in the art can readily assess the potency and efficacy of a candidate modulator of the presently disclosed subject matter and adjust the therapeutic regimen accordingly.

After review of the disclosure herein of the presently disclosed subject matter, one of ordinary skill in the art can tailor the dosages to an individual subject, taking into account the particular formulation, method of administration to be used with the composition, and other factors. Further calculations of dose can consider subject height and weight, severity and stage of symptoms, and the presence of additional deleterious physical conditions. Such adjustments or variations, as well as evaluation of when and how to make such adjustments or variations, are well known to those of ordinary skill in the art of medicine.

Thus, in some embodiments the term "effective amount" is used herein to refer to an amount of an AKR1C3 inhibitor, a pharmaceutically acceptable salt thereof, a derivative thereof, or a combination thereof sufficient to produce a measurable amelioration of a symptom associated with an undesirable AKR1C3 biological activity. Actual dosage levels of active ingredients in an AKR1C3 inhibitor composition of the presently disclosed subject matter can be varied so as to administer an amount of the active compound(s) that is effective to achieve the desired response for a particular subject and/or application. The selected dosage level can depend upon a variety of factors including the activity of the AKR1C3 inhibitor composition, formulation, route of administration, combination with other drugs or treatments, severity of the condition being treated, and physical condition and prior medical history of the subject being treated. In some embodiments, a minimal dose is administered, and dose is escalated in the absence of dose-limiting toxicity to a minimally effective amount. Determination and adjustment of an effective dose, as well as evaluation of when and how to make such adjustments, are known to those of ordinary skill in the art.

For administration of an AKR1C3 inhibitor composition as disclosed herein, conventional methods of extrapolating human dosage based on doses administered to a murine animal model can be carried out using techniques known to one of ordinary skill in the art. Drug doses can also be given in milligrams per square meter of body surface area because this method rather than body weight achieves a good correlation to certain metabolic and excretionary functions. Moreover, body surface area can be used as a common denominator for drug dosage in adults and children as well as in different animal species as described by Freireich et al., 1966. Briefly, to express a mg/kg dose in any given species as the equivalent mg/m$^2$ dose, multiply the dose by the appropriate km factor. In an adult human, 100 mg/kg is equivalent to 100 mg/kg×37 kg/m$^2$=3700 mg/m$^2$.

In some embodiments of the presently disclosed subject matter, the AKR1C3 inhibitor composition comprises an effective amount of a compound of any of Formulae I-IV disclosed herein, pharmaceutically acceptable salts thereof, derivatives thereof, or combinations thereof.

For additional guidance regarding formulations and doses, see U.S. Pat. Nos. 5,326,902; 5,234,933; PCT International Publication No. WO 93/25521; Remington et al., 1975; Goodman et al., 1996; Berkow et al., 1997; Speight et al., 1997; Ebadi, 1998; Duch et al., 1998; Katzung, 2001; Gerbino, 2005.

V.C. Routes of Administration

The presently disclosed AKR1C3 inhibitor compositions can be administered to a subject in any form and/or by any route of administration. In some embodiments, the formulation is a sustained release formulation, a controlled release formulation, or a formulation designed for both sustained and controlled release. As used herein, the term "sustained release" refers to release of an active agent such that an approximately constant amount of an active agent becomes available to the subject over time. The phrase "controlled release" is broader, referring to release of an active agent over time that might or might not be at a constant level. Particularly, "controlled release" encompasses situations and formulations where the active ingredient is not necessarily released at a constant rate, but can include increasing release over time, decreasing release over time, and/or constant release with one or more periods of increased release, decreased release, or combinations thereof. Thus, while "sustained release" is a form of "controlled release", the latter also includes delivery modalities that employ changes in the amount of an active agent (e.g., an AKR1C3 inhibitor composition) that are delivered at different times.

In some embodiments, the sustained release formulation, the controlled release formulation, or the combination thereof is selected from the group consisting of an oral formulation, a peroral formulation, a buccal formulation, an enteral formulation, a pulmonary formulation, a rectal formulation, a vaginal formulation, a nasal formulation, a lingual formulation, a sublingual formulation, an intravenous formulation, an intraarterial formulation, an intracardial formulation, an intramuscular formulation, an intraperitoneal formulation, a transdermal formulation, an intracranial formulation, an intracutaneous formulation, a subcutaneous formulation, an aerosolized formulation, an ocular formulation, an implantable formulation, a depot injection formulation, a transdermal formulation and combinations thereof. In some embodiments, the route of administration is selected from the group consisting of oral, peroral, buccal, enteral, pulmonary, rectal, vaginal, nasal, lingual, sublingual, intravenous, intraarterial, intracardial, intramuscular, intraperitoneal, transdermal, intracranial, intracutaneous, subcutaneous, ocular, via an implant, and via a depot injection. Where applicable, continuous infusion can enhance drug accumulation at a target site (see, e.g., U.S. Pat. No. 6,180,082). See also U.S. Pat. Nos. 3,598,122; 5,016,652; 5,935,975; 6,106,856; 6,162,459; 6,495,605; and 6,582,724; and U.S. Patent Application Publication No. 2006/0188558 for transdermal formulations and methods of delivery of compositions. In some embodiments, the administering is via a route selected from the group consisting of peroral, intravenous, intraperitoneal, inhalation, intraprostatic, and intratumoral.

The particular mode of drug administration used in accordance with the methods of the presently disclosed subject matter depends on various factors, including but not limited to the vector and/or drug carrier employed, the severity of the condition to be treated, and mechanisms for metabolism or removal of the drug following administration.

V.D. Combination Therapies

In some embodiments, a method of treatment that comprises administration of an AKR1C3 inhibitor of the presently disclosed subject matter can also comprise any other therapy known or expected to be of benefit to a subject with a condition, disease, or disorder associated with an undesirable AKR1C3 biological activity. By way of example and not limitation, prostate cancer, including but not limited to CRPC, is a condition, disease, or disorder associated with an undesirable AKR1C3 biological activity. Any standard therapy that is used to treat prostate cancer or a precursor condition thereof can be employed before, concurrently with, and/or after administration of an AKR1C3 inhibitor of the presently disclosed subject matter. Standard treatment approaches for prostate cancer include, but are not limited to brachytherapy and other forms of radiation treatment(s), chemotherapy, cryosurgery/cryotherapy, hormone therapy, surgery (including, but not limited to prostatectomy), and prostate monitoring (see e.g., U.S. Pat. No. 7,405,227).

VI. Other Applications

As disclosed herein, the initial target for a selective inhibitor of AKR1C3 is CRPC, which results in 27,000 deaths annually in the U.S. and for which current treatments are ineffective. However, AKR1C3 is also involved in the metabolism of other steroids as well as prostaglandins, implicating other disease targets.

For example, AKR1C3 through its 17β-hydroxysteroid dehydrogenase activity also converts estrone (a weak estrogen) to 17β-estradiol (a potent estrogen) and regulates local estrogen production in the breast. AKR1C3 is expressed in normal breast tissue, its upregulation has been detected in 65-85% of breast cancer tissues, and its upregulation is associated with poor prognosis. Selective AKR1C3 inhibitors thus in some embodiments have a role in the hormonal ablative therapy of breast cancer (Lin et al., 2004; Jansson et al., 2006; Suzuki et al., 2007).

In addition to its HSD activities, AKR1C3 is characterized as human prostaglandin (PG) F synthase. Homogenous recombinant AKR1C3 stereospecifically and efficiently converts $PGH_2$ to $PGF_{2\alpha}$ and $PGD_2$ to $9\alpha,11\beta$-$PGF_2$ (see e.g., Matsuura et al., 1998; Suzuki-Yamamoto et al., 1999). Conversion of $PGD_2$ to a $PGF_2$ isomer by leukemia cells was reduced by the AKR1C3 inhibitor indomethacin or a shRNA targeting AKR1C3 and led to anti-proliferative effects. Currently, a non-selective AKR1C3 inhibitor, 6-medroxyprogesterone acetate, is being used in early clinical trials to treat acute myeloid leukemia (AML) in Europe, based on a clearly defined role of AKR1C3 in regulating the differentiation of AML cells (Khanim et al., 2009). Thus, in some embodiments the AKR1C3 inhibitors disclosed herein can be employed for the treatment of AML. The presently disclosed AKR1C3 inhibitors can also be used to assess the role of AKR1C3 in cancer biology since AKR1C3 can also affect other pro-proliferative signaling pathways.

PGF2α produced by AKR1C3 acts through the F prostanoid (FP) receptor to induce cell proliferation, invasiveness, and angiogenesis in endometrial cancer (see e.g., Milne & Jabbour, 2003; Sales et al., 2004; Sales et al., 2005). Thus, in some embodiments the AKR1C3 inhibitors of the presently disclosed subject matter are employed in the treatment of endometrial cancer.

By depleting PGD2 levels, AKR1C3 prevents its spontaneous dehydration and rearrangement to form anti-proliferative and anti-inflammatory PGJ2 isomers, including 15-deoxy-Δ12,14-PGJ2 (15dPGJ2). 15dPGJ2 covalently reacts with a key cysteine residue in PPARγ, resulting in its activation (see e.g., Harris & Phipps, 2002; Shiraki et al., 2005). 15dPGJ2 also reacts with cysteine residues in other proteins, including DNA binding domains of nuclear factor κB (NF-κB) and ERα, resulting in the loss of transcriptional activity (see e.g., Straus et al., 2000; Kim et al., 2007). Prevention of PGD2 depletion by the AKR1C3 inhibitors of the presently disclosed subject matter would retain these anti-proliferative signaling pathways in tumors and thus in some embodiments can be employed therapeutically for these purposes.

Additionally, due to its roles in progesterone and prostaglandin F2α metabolism, in some embodiments the presently disclosed AKR1C3 inhibitors can be employed to prevent premature parturition. Indomethacin is currently used successfully for this condition, but has severe side effects due to inhibition of COX in developing organs. As such, the presently disclosed AKR1C3 inhibitors can be employed as they substantially lack COX inhibitory activity.

EXAMPLES

The following Examples provide further illustrative embodiments. In light of the present disclosure and the general level of skill in the art, those of skill will appreciate that the following Example is intended to be exemplary only and that numerous changes, modifications, and alterations can be employed without departing from the scope of the presently disclosed subject matter.

Materials and Methods for the Examples

Solvents and Reagents: All reagents and solvents were of commercial quality and were used without further purification. HPLC grade solvents obtained from Fischer (Pittsburgh, Pa., United States of America) were used for chromatographic separations. Column chromatography was performed using standard grade silica gel from Sorbent Technologies, Twinsburg, Ohio, United States of America (Catalog No. 10930-5, Porosity: 60 A, Particle Size: 32-63 mm, 230×450 mesh, pH range 6.5-7.5). Flash chromatography was conducted on a Biotage SP1 automated flash chromatography system equipped with a fixed wavelength UV detector ($\lambda$=254 nm) using prefabricated Flash KP-SIL columns (size according to requirements). Analytical thin-layer chromatography (TLC) analyses were performed on fluorescent silica gel 60 $F_{254}$ plates (250 um) from Whatman (PARTISIL® LK6D, Catalog No. 4865-821). Spots were visualized under natural light, and UV illumination at I=254 and 365 nm.

Instrumental Analysis: $^1H$ and $^{13}C$ spectra were collected on a Bruker AV-400 with sample changer (BACS 60) at 400 and 100 MHz, respectively. Chemical shifts are reported in ppm relative to residual solvent peaks as an internal standard set to d 2.52 and d 40.45 (DMSO-$d_6$). $^{19}F$ NMR spectra were collected on a Bruker AV-300 at 282 MHz. Data are reported as follows: chemical shift, multiplicity (s=singlet, d=doublet, t=triplet, q=quartet, p=pentet, sext=sextet, sept=septet, br=broad, dd=doublet of doublets, dq=doublet of quartets, td=triplet of doublets, pd=pentet of doublets, m=multiplet), coupling constant (Hz), and integration.

Low-resolution mass analyses (LCMS) were carried out on an Agilent 1200 LCMS system with electrospray ionization (Agilent 6130 quadrupole analyzer, positive ion mode). ESI-MS results are given as m/z ratio ([M+1]$^+$). Purity of compounds was determined by analytical high performance liquid chromatography (HPLC) on a YMC J'sphere H-80 S-4 column (3.0×50 mm), which was eluted with a gradient (see time table below) with an ACN—$H_2O$ (plus 0.1% TFA) system at a flow rate of 1.4 mL/min. (HP)LC was performed on an Agilent 1200 analytical LCMS with UV detection at 214 and 254 nm along with ELCD detection. LC results are presented as tR (min) and relative purity (%). The purity of all tested compounds is >95%, if not denoted otherwise.

HPLC samples were diluted to a final concentration of about 0.1-0.2 mg/ml using MeOH. If required, samples were filtered through a Spartan-Filter 13/0,45 RC into the 1 ml HPLC glass vials in order to separate from particulate material.

Agilent 1200 Binary Pump and Thermostat Settings:
Solvent A: 95% (water (0.1% TFA)
Solvent B: 5.0% (Acetonitrile)

| Gradient | | |
|---|---|---|
| Time | Solv. B | Flow |
| 0.00 | 5.0 | 1.400 |
| 3.60 | 100.0 | |
| 4.00 | 100.0 | |
| 4.05 | 5.0 | |

Stop time: 4.20 min
Pressure Limits (bar)
Minimum pressure: 0
Maximum pressure: 400
Column temperature: 45° C.

Example 1

Exemplary Synthesis Schemes

A library of indomethacin analogs were synthesized. Initial synthesis was directed towards removal of the 2'-methyl group of indomethacin to produce 2'-des-methyl analogs and/or the replacement of the carboxylic side chain with a 3'-methyl group to produce 3'-methyl-analogs. The basic structures of these derivatives are depicted in FIG. 2. These alterations eliminated COX-1 and COX-2 inhibition (see Prusakiewicz et al., 2004).

Figure 3:
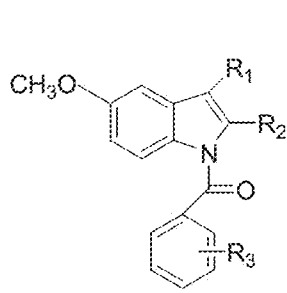
FIG. 3 depicts other structures of exemplary indomethacin derivatives that are AKR1C3-specific inhibitors of the presently disclosed subject matter.
Figure 3:
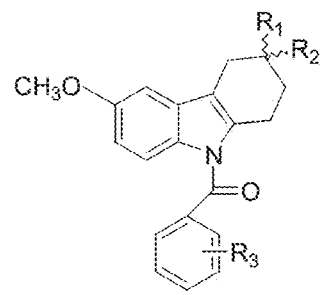
Figure 4:
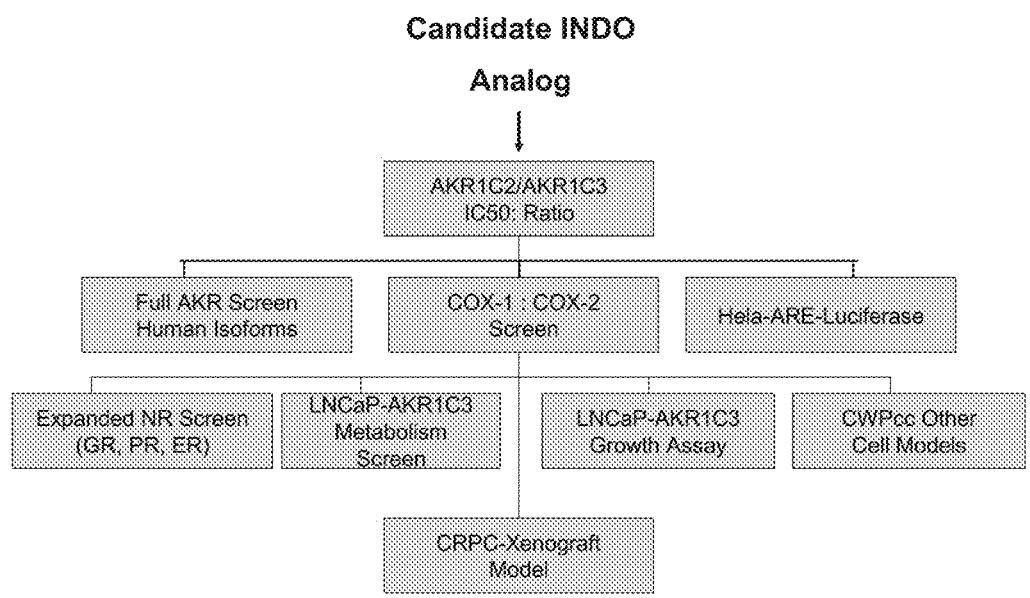
FIG. 4 is a schematic diagram of an initial screening strategy to identify AKR1C3-specific inhibitors of the presently disclosed subject matter, where: COX-1 and COX-2=prostaglandin $H_2$ synthase 1 and 2, respectively; ARE-luciferase=androgen response element driven luciferase reporter gene activity; NR=nuclear receptor (GR=glucocorticoid receptor; PR=progesterone receptor; and AR=androgen receptor)' LNCaP-AKR1C3 (androgen dependent human prostate cancer cell line stably transfected with AKR1C3); CRPC=castrate resistant prostate cancer.

Lead Compounds 1, 2, and 3 were used to generate a second generation of compounds represented by the Compound 4, 5 Series and the Compound 6 Series (see FIG. 3).

The presently disclosed subject matter thus includes, but is not limited to, these and related structures as well as uses thereof.

Figure 5:
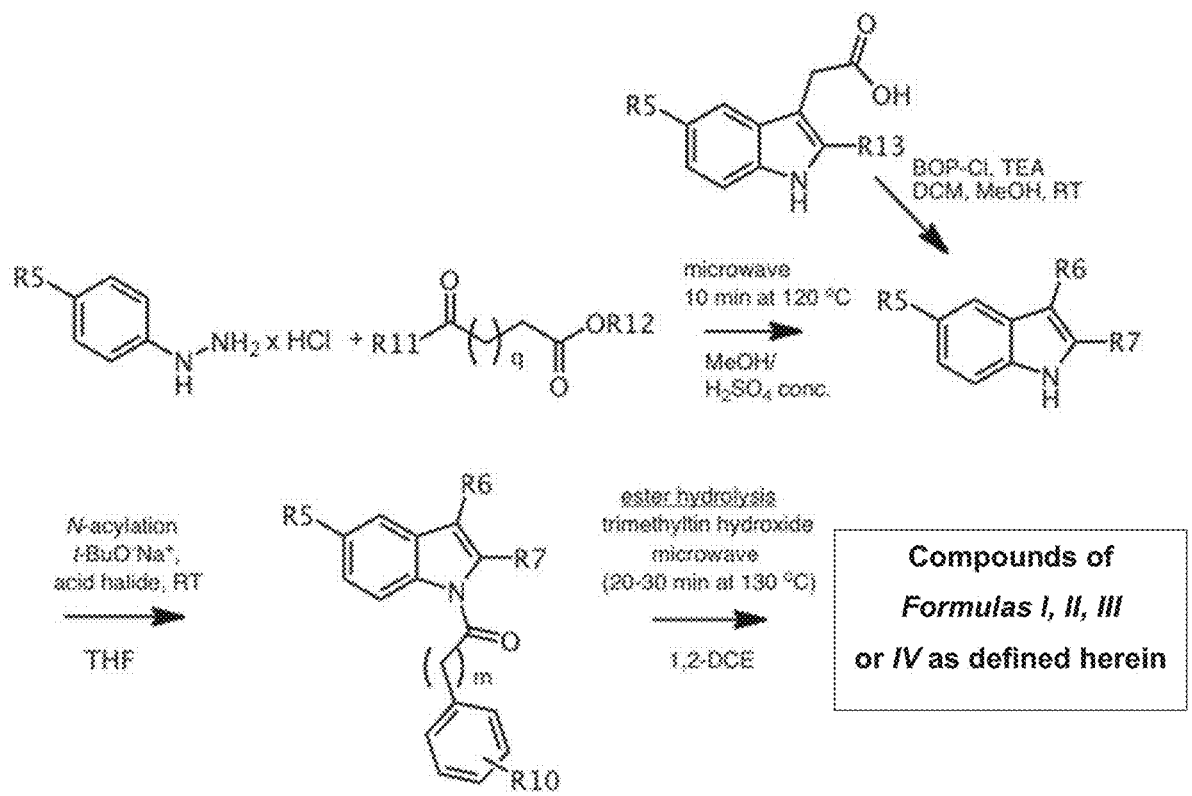
FIGS. 5-8 depict exemplary, non-limiting synthesis schemes for producing the AKR1C3-specific inhibitors of the presently disclosed subject matter. For each of these Figures, individual R groups are as defined hereinabove, and m is 0, 1, or 2 as defined hereinabove.

Exemplary synthesis schemes for representative embodiments as set forth in FIG. 5 are as follows:

Example A: methyl 2-(5-methoxy-1H-indol-3-yl)acetate. A reaction mixture containing 2-(5-methoxy-1H-indol-3-yl) acetic acid (0.5 g, 2.44 mmol) and BOP—Cl (0.62 g, 2.44 mmol) in 7 mL of anhydrous $CH_2Cl_2$ was treated with triethyl amine (0.49 g, 4.87 mmol) and allowed to stir at ambient temperature for 5 min. The mixture was then combined with anhydrous methanol (0.34 mL) and continuously stirred overnight at room temperature. Following dilution with dichloromethane (30 mL), the organic solution was washed with water (2×15 mL), dried over $Na_2SO_4$, and filtered (using a commercial phase separator syringe with attached drying cartridge). The organic filtrate was collected and concentrated in vacuo and the crude ester was purified by flash chromatography on silica gel (ethyl acetate/hexane gradient) to afford the title compound as viscous yellow oil, which permanently crystallized upon storage at −20° C. (453 mg, 85%). $C_{12}H_{13}NO_3$, $M_r$=219.24; $^1H$ NMR (400 MHz, DMSO-$d_6$) d: 3.60 (s, 3H), 3.70 (s, 2H), 3.74 (s, 3H), 6.72 (dd, J=2.4/8.8 Hz, 1H), 6.96 (d, J=2.4 Hz, 1H), 7.19 (d, J=2.4 Hz, 1H), 7.23 (d, J=8.8 Hz, 1H), 10.77 (s, 1H); LCMS (ESI) tR: 1.95 min (>99%, UV254), m/z: 220.1 [M+1]$^+$.

Example B: methyl 2-(5-fluoro-2-methyl-1H-indol-3-yl) acetate. A stirred mixture of 39.3 mg (0.34 mmol) of 4-oxopentanoic acid, *50 mg (0.31 mmol) of (4-fluorophenyl)hydrazine hydrochloride, 1 mL of methanol and 40 µL of concentrated sulfuric acid in a 2 mL microwave process vial was heated for 10 min at 120° C. under argon in a microwave synthesizer. The alcoholic solution was concentrated to about one-third of its original volume and then transferred to a phase separator syringe filled with cold water (2 mL). The organic compound was repeatedly extracted with dichloromethane (3×3 mL) and the combined organic phases were washed with brine (2 mL), dried over Na$_2$SO$_4$ and filtered. Removal of the organic solvent and treatment of the residue with a little hexane afford the title compound in 84% yield (39 mg) as viscous mass. C$_{12}$H$_{12}$FNO$_2$, M$_r$=221.23; $^1$H NMR (400 MHz, DMSO-d$_6$) d: 2.31 (s, 3H), 3.57 (s, 3H), 3.65 (s, 2H), 6.81 (td, J=2.4/9.2 Hz, 1H), 7.10 (dd, J=2.4/10.0 Hz, 1H), 7.21 (dd, J=4.4/8.8 Hz, 1H), 10.97 (s, 1H); $^{19}$F NMR (282 MHz, DMSO-d$_6$) d: −123.78 (d, 5'-F); LCMS (ESI) tR: 2.18 min (95%, UV220, ELSD), m/z: 222.2 [M+1]$^+$. [* instead of the acid one could also use the methyl ester with the same outcome]

Example C: methyl 3-(5-fluoro-3-methyl-1H-indol-2-yl) propanoate. A stirred mixture of 88.8 mg (0.68 mmol) of 4-oxohexanoic acid, * 100 mg (0.62 mmol) of (4-fluorophenyl)hydrazine hydrochloride, 3 mL of methanol and 80 μL of concentrated sulfuric acid in a 5 mL microwave process vial was heated for 10 min at 120° C. under argon in a microwave synthesizer. The alcoholic solution was concentrated to about one-third of its original volume and then transferred to a phase separator syringe filled with cold water (4 mL). The organic compound was repeatedly extracted with dichloromethane (3×5 mL) and the combined organic phases were washed with brine (4 mL), dried over Na$_2$SO$_4$ and filtered. Removal of the organic solvent and treatment of the residue with a little hexane afford the title compound in 46% yield (67 mg) as viscous mass. C$_{13}$H$_{14}$FNO$_2$, M$_r$=235.25; $^1$H NMR (400 MHz, DMSO-d$_6$) d: 2.12 (s, 3H), 2.66 (t, J=8.0 Hz, 2H), 2.93 (t, J=7.6 Hz, 2H), 3.58 (s, 3H), 6.80 (td, J=2.8/9.2 Hz, 1H), 7.10 (dd, J=2.4/10.2 Hz, 1H), 7.20 (dd, J=4.6/8.6 Hz, 1H), 10.74 (bs, 1H); $^{19}$F NMR (282 MHz, DMSO-d$_6$) d: −124.03 (d, 5'-F); LCMS (ESI) tR: 2.58 min (>99%, UV220), m/z: 236.2 [M+1]$^+$. [* instead of the acid one could also use the methyl ester with the same outcome.]

Example D: methyl 2-(1-(4-chlorobenzoyl)-5-methoxy-1H-indol-3-yl)acetate. Methyl 2-(5-methoxy-1H-indol-3-yl)acetate (60 mg, 0.27 mmol) and NaH (8 mg, 0.33 mmol) were stirred in anhydrous DMF (1 mL) at 0° C. under argon for 30 min, at which time 4-chlorobenzoyl chloride (57 mg, 0.33 mmol) was added. The reaction mixture was stirred overnight at room temperature and was then poured into cold water (2 mL). The organic compound was immediately extracted with dichloromethane (2×2 mL), dried over Na$_2$SO$_4$, filtered, and concentrated in vacuo. The residue was purified on silica (ethyl acetate/hexane gradient) and recrystallized from hexane. Yield: 18 mg (18%). C$_{19}$H$_{16}$ClNO$_4$, M$_r$=357.79; $^1$H NMR (400 MHz, DMSO-d$_6$) d: 3.61 (s, 3H), 3.78 (s, 2H), 3.81 (s, 3H), 7.00 (dd, J=2.4/9.0 Hz, 1H), 7.12 (d, J=2.4 Hz, 1H), 7.35 (s, 1H), 7.65-7.77 (m, 4H), 8.17 (d, J=8.8 Hz, 1H); LCMS (ESI) tR: 2.81 min (>99%, ELSD), m/z: 358.0 [M+1]$^+$.

Example E: methyl 3-(1-(4-chlorobenzoyl)-5-fluoro-2-methyl-1H-indol-3-yl)propanoate. To a cooled solution (ice bath, 0-5° C.) of methyl 3-(5-fluoro-2-methyl-1H-indol-3-yl)propanoate (80 mg, 0.34 mmol) in THF (2.5 mL) was added $^t$BuONa (2 M in THF, 204 μL, 0.41 mmol), and the mixture was stirred for 20 min at the low temperature. 4-chlorobenzoyl chloride (71.4 mg, 0.41 mmol) was added and the reaction was stirred overnight at room temperature. The reaction was combined with saturated aqueous NH$_4$Cl (1 mL; provided in a 10 mL glass vial) and the organic compound was extracted with ethyl acetate (3×3 mL), washed with brine and water, dried over Na$_2$SO$_4$ and concentrated in vacuo. The crude residue was subjected to flash chromatography (SiO$_2$, ethyl acetate/hexane gradient) to afford the pure title compound as yellow oil in 49% yield (62 mg). C$_{20}$H$_{17}$ClFNO$_3$, M$_r$=373.81; $^1$H NMR (400 MHz, DMSO-d$_6$) d: 2.19 (s, 3H), 2.59 (t, J=7.4 Hz, 2H), 2.92 (t, J=7.6 Hz, 2H), 3.56 (s, 3H), 6.94 (td, J=2.4/9.2 Hz, 1H), 7.08 (dd, J=4.6/9.0 Hz, 1H), 7.39 (dd, J=2.4/9.2 Hz, 1H), 7.63-7.68 (m, 4H); LCMS (ESI) tR: 3.21 min (>95%, ELSD), m/z: 374.3 [M+1]$^+$.

Example F: methyl 2-(5-methoxy-1-(4-(trifluoromethyl)benzoyl)-1H-indol-3-yl)acetate. To a cooled solution (ice bath, 0-5° C.) of methyl methyl 2-(5-methoxy-1H-indol-3-yl)acetate (80 mg, 0.36 mmol) in THF (2.5 mL) was added $^t$BuONa (2 M in THF, 219 uL, 0.44 mmol), and the mixture was stirred for 20 min at the low temperature. 4-(trifluoromethyl)benzoyl chloride (91.3 mg, 0.44 mmol) was added and the reaction was stirred overnight at room temperature. The reaction was combined with saturated aqueous NH$_4$Cl (1 mL; provided in a 10 mL glass vial) and the organic compound was extracted with ethyl acetate (3×3 mL), washed with brine and water, dried over Na$_2$SO$_4$ and concentrated in vacuo. The crude residue was subjected to flash chromatography (SiO$_2$, ethyl acetate/hexane gradient) to afford the pure title compound as brownish oil in 29% yield (41 mg). C$_2$H$_{16}$F$_3$NO$_4$, M$_r$=391.34; $^1$H NMR (400 MHz, DMSO-d$_6$) d: 3.61 (s, 3H), 3.78 (s, 2H), 3.81 (s, 3H), 7.02 (dd, J=2.4/9.2 Hz, 1H), 7.13 (d, 2.4 Hz, 1H), 7.31 (s, 1H), 7.93-7.98 (m, 4H), 8.22 (d, J=8.8 Hz, 1H); $^{19}$F NMR (282 MHz, DMSO-d$_6$) d: −59.61 (s, —CF$_3$); LCMS (ESI) tR: 2.78 min (>99%, ELSD), m/z: 392.0 [M+1]$^+$.

Example G: 2-(1-(4-chlorobenzoyl)-5-methoxy-1H-indol-3-yl)acetic acid. In a microwave process vial methyl 2-(1-(4-chlorobenzoyl)-5-methoxy-1H-indol-3-yl)acetate (10 mg, 0.028 mmol) was dissolved in 1,2-dichloro ethane (1 mL) and after addition of trimethyltin hydroxide (25 mg, 0.14 mmol) the reaction mixture was heated for 30 min at 130° C. in a microwave (TLC analysis indicated complete reaction). Dichloromethane (1 mL) and 50% AcOH (2 mL) were added to the cold reaction solution and the resulting biphasic mixture was agitated until both layers were clear. The organic phase was collected, washed with brine, dried over Na$_2$SO$_4$ and filtered (using a phase separator syringe with drying cartridge). Removal of the solvent (dichloromethane) in vacuo and following silica gel chromatography using an ethyl acetate/hexane gradient (0.5% AcOH) afforded the pure title compound quantitatively. C$_{18}$H$_{14}$ClNO$_4$, M$_r$=343.76; $^1$H NMR (400 MHz, DMSO-d$_6$) d: 3.67 (s, 2H), 3.81 (s, 3H), 6.99 (dd, J=2.4/9.2 Hz, 1H), 7.12 (d, J=2.4 Hz, 1H), 7.32 (s, 1H), 7.65-7.77 (m, 4H), 8.17 (d, J=9.2 Hz, 1H); LCMS (ESI) tR: 2.60 min (>99%, ELSD), m/z: 344.0 [M+1]$^+$.

Example H: 3-(1-(4-chlorobenzoyl)-5-methoxy-3-methyl-1H-indol-2-yl)-2-methylpropanoic acid. 2-methyl-4-oxohexanoic acid (27.6 mg, 0.19 mmol) was added to a stirred solution of 4-chloro-N-(4-methoxyphenyl)benzohydrazide hydrochloride (50 mg, 0.16 mmol) in acetic acid (0.5 mL), the mixture was heated at 80° C. under nitrogen for 3 h, then it was allowed to cool to ambient temperature and stirred overnight. Ice-water (2 mL) was poured into the cold reaction mixture and the formed precipitate was collected by filtration, carefully washed with water and dried in vacuo to yield the title compound (27 mg, 44%) as an off-white solid. C$_{21}$H$_{20}$ClNO$_4$, M$_r$=385.84; $^1$H NMR (400 MHz, DMSO-d$_6$) d: 1.01 (d, J=6.8 Hz, 3H), 2.19 (s, 3H), 2.54 (sex, J=7.2 Hz, 1H), 2.91-3.19 (m, 2H), 3.76 (s, 3H), 6.46 (d, J=9.2 Hz, 1H), 6.64 (dd, J=2.4/9.0 Hz, 1H), 7.02 (d, J=2.4 Hz, 1H); LCMS (ESI) tR: 2.78 min (>99%, ELSD), m/z: 386.1 [M+1]$^+$.

Example I: 3-(1-(4-chlorobenzoyl)-5-methoxy-3-methyl-1H-indol-2-yl)-N-(methylsulfonyl)propanamide. To a cooled mixture (0-5° C.) of 3-(1-(4-chlorobenzoyl)-5-methoxy-3-methyl-1H-indol-2-yl)propanoic acid (40 mg, 0.11 mmol) in CH$_2$Cl$_2$ (1 mL), 1'1'-carbonyldiimidazole (CDI) (17.4 mg, 0.11 mmol) was added. After the mixture was stirred for 2 h at 0-5° C., methansulfonamide (10 mg, 0.11 mmol) and diazobicyclo-[5.4.0]undec-7-ene (DBU) (16.1 μL, 0.11 mmol) were added. The mixture was left stirring overnight. Glacial AcOH (13.2 μL) was added, the reaction mixture was diluted with CH$_2$Cl$_2$ (1 mL), and the organic layer was washed with 10% NaH$_2$PO$_4$ (pH 4) (1×1 mL) and water (3 mL), dried over Na$_2$SO$_4$, filtered, and concentrated under reduced pressure to give a crude residue that was purified by flash chromatography (SiO$_2$, ethyl acetate/hexane, 0.5% AcOH gradient) to afford the title compound as a bright yellow solid (32 mg, 66%). C$_{21}$H$_{21}$ClN$_2$O$_5$S, M$_r$=448.92; $^1$H NMR (400 MHz, DMSO-d$_6$) d: 2.21 (s, 3H), 2.55 (t, J=7.2 Hz, 2H), 3.11 (t, J=7.2 Hz, 2H), 3.16 (s, 3H), 3.75 (s, 3H), 6.43 (d, J=9.2 Hz, 1H), 6.64 (dd, J=9.0 Hz, 1H), 7.02 (d, J=2.4 Hz, 1H), 7.64-7.69 (m, 4H); LCMS (ESI) tR: 2.74 min (>95%, UV254, ELSD), m/z: 249.1 [M+1]$^+$.

Example J: 2-(1-(4-chlorobenzoyl)-5-methoxy-1H-indol-3-yl)acetyl chloride. Oxalyl chloride (30 μL, 0.35 mmol) was added dropwise to a solution of 2-(1-(4-chlorobenzoyl)-5-methoxy-1H-indol-3-yl)acetic acid (100 mg, 0.29 mmol) in 2 mL of dry CH$_2$Cl$_2$ under argon. The reaction mixture was stirred overnight at room temperature. The solvent was evaporated and the crude product was washed with dry hexane (3×1 mL) and dried in vacuo to give the title compound in 95% yield (100 mg). C$_{18}$H$_{13}$Cl$_2$NO$_3$, M$_r$=362.21; $^1$H NMR (400 MHz, DMSO-d$_6$) d: 3.90 (s, 3H), 4.21 (s, 2H), 6.95 (d, J=2.4 Hz, 1H), 7.04 (dd, J=2.4/9.0 Hz, 1H), 7.29 (s, 1H), 7.52-7.55 (m, 2H), 7.67-7.71 (m, 2H), 8.29 (d, J=9.2 Hz, 1H); LCMS (ESI) tR: 2.72 min (>99%, UV254), m/z: 358.2 [M+1]$^+$.

Example K: 2-(1-(4-chlorobenzoyl)-5-methoxy-1H-indo-3-yl)-N-((trifluoromethyl)sulfonyl) acetamide. 80 mg (0.22 mmol) 2-(1-(4-chlorobenzoyl)-5-methoxy-1H-indol-3-yl) acetyl chloride and 49.4 mg (0.33 mmol) trifluoromethanesulfonamide were dissolved in 1.8 mL 1,2-dichloro ethane (or CH$_2$Cl$_2$) under stirring. Then 17.5 mg (0.22 mmol) pyridine were added and the reaction was allowed to run at ambient temperature until the starting material was consumed (~4 h). After the addition of 13 μL of AcOH the organic solution was washed with H$_2$O (3×2 mL), dried over Na$_2$SO$_4$, filtered and the concentrated in vacuo. The crude product was purified by flash chromatography (SiO$_2$, ethyl acetate/hexane, 0.5% AcOH gradient) to afford the title compound in 70% yield (73 mg). C$_{19}$H$_{14}$ClF$_3$N$_2$O$_5$S, M$_r$=474.84; $^1$H NMR (400 MHz, DMSO-d$_6$) d: 3.44 (s, 2H), 3.79 (s, 3H), 6.95 (dd, J=2.6/9.0 Hz, 1H), 7.14 9d, J=2.4 Hz, 1H), 7.23 (s, 1H), 7.64-7.66 (m, 2H), 7.72-7.74 (m, 2H), 8.15 (d, J=8.8 Hz, 1H, C7'-H); $^{19}$F NMR (282 MHz, DMSO-d$_6$) d: –75.58 (s, —CF$_3$); LCMS (ESI) tR: 2.37 min (>99%, UV254, ELSD), m/z: 475.0 [M+1]$^+$.

Exemplary synthesis schemes for representative embodiments as set forth in FIG. 6 are as follows:

Example L: methyl 6-fluoro-2,3,4,9-tetrahydro-1H-carbazole-3-carboxylate. A stirred mixture of 96.2 mg (0.68 mmol) of 4-oxocyclohexanecarboxylic acid, 100 mg (0.62 mmol) of (4-fluorophenyl)hydrazine hydrochloride, 3 mL of methanol and 80 μL of concentrated sulfuric acid in a 5 mL microwave process vial was heated for 10 min at 120° C. under argon in a microwave. The alcoholic solution was concentrated to about one-third of the original volume and then externally cooled (ice bath). An off-white product precipitate formed, which could be filtered off and thereby was carefully washed with a little cold water. Alternatively the reaction mixture was poured onto chopped ice and water and the precipitate collected by filtration to afford the title compound in 100% yield (152 mg). C$_{14}$H$_{14}$FNO$_2$, M$_r$=247.26; $^1$H NMR (400 MHz, DMSO-d$_6$) d: 1.84-1.92 (m, 1H), 2.16-2.20 (m, 1H), 2.66-2.85 (m, 4H), 2.90 (dd, J=4.8/14.6 Hz, 1H), 3.65 (s, 3H), 6.80 (td, J=2.8/9.2 Hz, 1H), 7.10 (dd, J=2.8/10.0 Hz, 1H), 7.20 (dd, J=4.6/8.6 Hz, 1H) 10.80 (bs, 1H); LCMS (ESI) tR: 2.54 min (>99%, UV254, ELSD), m/z: 248.2 [M+1]$^+$.

Example M: methyl 6-methoxy-2,3,4,9-tetrahydro-1H-carbazole-3-carboxylate. (4-Methoxyphenyl)hydrazine hydrochloride (80.0 mg, 0.46 mmol) and methyl 4-oxocyclohexanecarboxylate (85.9 mg, 0.55 mmol) were dissolved in acetic acid (0.5 mL). The mixture was heated at 80° C. with stirring under nitrogen for 3 h, cooled, diluted with water (2 mL) and the resulting precipitate was collected by filtration, gently washed with water and dried in vacuo to yield the title compound (107 mg, 90%) as an off-white solid. C$_{15}$H$_{17}$NO$_3$, M$_r$=259.30; $^1$H NMR (400 MHz, DMSO-d$_6$) d: 1.81-1.91 (m, 1H), 2.15-2.19 (m, 1H), 2.66-2.84 (m, 4H), 2.90 (dd, J=4.6/14.2 Hz, 1H), 3.65 (s, 3H), 3.72 (s, 3H), 6.61 (dd, J=2.4/8.8 Hz, 1H), 6.86 (d, J=2.4 Hz, 1H), 7.11 (d, J=8.8 Hz, 1H), 10.51 (s, 1H); LCMS (ESI) tR: 2.27 min (>99%, ELSD), m/z: 260.2 [M+1]$^+$.

Example N: methyl 9-(4-chlorobenzoyl)-6-fluoro-2,3,4, 9-tetrahydro-1H-carbazole-3-carboxylate. To a cooled solution (ice bath, 0-5° C.) of methyl 6-fluoro-2,3,4,9-tetrahydro-1H-carbazole-3-carboxylate (80 mg, 0.32 mmol) in THF (2.5 mL) was added $^t$BuONa (2 M in THF, 194 μL, 0.39 mmol), and the mixture was stirred for 20 min at the low temperature. 4-Chlorobenzoyl chloride (67.9 mg, 0.39 mmol) was added and the reaction was aged overnight at room temperature. The reaction was poured into saturated aqueous NH$_4$Cl (1 mL; provided in a 10 mL glass vial) and the organic compound extracted with ethyl acetate (3×3 mL), washed with brine and water, dried over Na$_2$SO$_4$ and concentrated in vacuo. The crude residue was subjected to flash chromatography (SiO$_2$, ethyl acetate/hexane gradient) to afford the pure title compound as white crystalline solid in 14% yield (17 mg). C$_{21}$H$_{17}$ClFNO$_3$, M$_r$=385.82; $^1$H NMR (400 MHz, DMSO-d$_6$) d: 1.72-1.79 (m, 1H), 2.06-2.10 (m, 1H), 2.54-2.56 (m, 2H), 2.72-2.78 (m, 1H), 2.83-2.89 (m, 1H), 2.95 (dd, J=5.2/15.4 Hz, 1H), 3.65 (s, 3H), 6.99 (td, J=2.4/9.2 Hz, 1H), 7.23 (dd, J=4.6/9.0 Hz, 1H), 7.34 (dd, J=2.4/9.0 Hz, 1H), 7.62-7.69 (m, 4H); $^{19}$F NMR (282 MHz, DMSO-d$_6$) d: –123.87 (q, 6'-F); LCMS (ESI) tR: 3.24 min (>99%, ELSD), m/z: 386.0 [M+1]$^+$.

Example O: 9-(4-chlorobenzoyl)-6-methoxy-2,3,4,9-tetrahydro-1H-carbazole-2-carboxylic acid. 3-Oxocyclohexanecarboxylic acid (27.2 mg, 0.19 mmol) was added to a stirred solution of 4-chloro-N-(4-methoxyphenyl)benzohydrazide hydrochloride (50 mg, 0.16 mmol) in acetic acid (0.5 mL), the mixture was heated at 80° C. under nitrogen for 3 h, then it was allowed to cool to ambient temperature and stirred overnight. Ice-water (2 mL) was poured into the cold reaction mixture and the formed precipitate was collected by filtration, carefully washed with water and dried in vacuo to yield the title compound (50 mg, 82%) as an off-white solid. C$_{21}$H$_{10}$ClNO$_4$, M$_r$=383.82; $^1$H NMR (400 MHz, DMSO-d$_6$) d: 1.79-1.87 (m, 1H), 2.11-2.14 (m, 1H), 2.57-2.75 (m, 5H), 6.73 (dd, J=2.8/9.0 Hz, 1H), 6.97 (d, J=2.8 Hz, 1H), 7.06 (d, J=9.2 Hz, 1H), 7.62-7.69 (m, 4H); LCMS (ESI) tR: 2.82 min (>99%, ELSD), m/z: 384.0 [M+1]$^+$.

Exemplary synthesis schemes for representative embodiments as set forth in FIG. 7 are as follows:

Example P: methyl 2-(1H-indazol-3-yl)acetate. A solution of 2-(1H-indazol-3-yl)acetic acid (300 mg, 1.70 mmol) in methanol (15 mL) containing 5 drops of concentrated sulfuric acid was refluxed for 14 hours. The reaction mixture was concentrated under reduced pressure to a low volume, and then diluted with ethyl acetate (8 mL). The organic layer was treated with water (2×5 mL) and 10% sodium bicarbonate solution (5 mL). The ethyl acetate phase was collected, dried over sodium sulfate and concentrated to quantitatively obtain the title compound as crystalline solid upon drying at high vacuum. $C_{10}H_{10}N_2O_2$, $M_r$=190.20; $^1$H NMR (400 MHz, DMSO-$d_6$) d: 3.62 (s, 3H), 4.01 (s, 2H), 7.09 (td, J=0.8/7.4 Hz, 1H), 7.33 (td, J=1.0/7.7 Hz, 1H), 7.48 (d, J=8.4 Hz, 1H), 7.69 (d, J=8.4 Hz, 1H); $^{13}$C NMR (100 MHz, DMSO-$d_6$) d: 33.04 (s, —$CH_2$—), 52.17 (s, —$OCH_3$), 110.49 (s, C7'), 120.29 (s), 120.43 (s), 122.20 (s, C4a'), 126.40 (s, C6'), 138.83 (s, C7a'), 141.20 (s, C3'), 171.03 (s, >C=O); LCMS (ESI) tR: 1.65 min (>99%, UV254), m/z: 191.2 [M+1]$^+$.

Example Q: methyl 2-(1-(4-chlorobenzoyl)-1H-indazol-3-yl)acetate. To a cooled solution (ice bath, 0-5° C.) of methyl 2-(1H-indazol-3-yl)acetate (80 mg, 0.42 mmol) in THF (2.5 mL) was added $^t$BuONa (2 M in THF, 252.4 μL, 0.50 mmol), and the mixture was stirred for 25 min at the low temperature. 4-Chlorobenzoyl chloride (88.3 mg, 0.50 mmol) was added and the reaction was aged overnight at room temperature. The reaction was quenched with saturated aqueous $NH_4Cl$ (provided in a commercial phase separator syringe) and the organic compound was extracted with $CH_2Cl_2$, washed with brine and water, dried over $Na_2SO_4$, filtered and concentrated in vacuo. The crude residue was subjected to flash chromatography ($SiO_2$, ethyl acetate/hexane gradient) to afford the title compound as yellow oil, which permanently crystallized upon drying at high vacuum and storage at −20° C. Yield: 51 mg (37%). $C_{17}H_{13}ClN_2O_3$, $M_r$=328.75; $^1$H NMR (400 MHz, DMSO-$d_6$) d: 3.65 (s, 3H), 4.16 (s, 2H), 7.50 (td, J=0.8/7.6 Hz, 1H), 7.63-7.66 (m, 2H), 7.71 (td, J=1.0/7.6 Hz, 1H), 7.91 (d, J=8.0 Hz, 1H), 8.00-8.03 (m, 2H), 8.41 (d, J=8.4 Hz, 1H); LCMS (ESI) tR: 2.80 min (>99%, ELSD), m/z: 329.0 [M+1]$^+$.

The key methyl 2-(5-methoxy-1H-pyrrolo[3,2-b]pyridin-3-yl)acetate intermediate can be synthesized according to the steps outlined in FIG. 8 using microwave irradiation. These steps are presented in more detail as follows:

Example R: alkylation reaction to methyl 3-cyano-3-(6-methoxy-3-nitropyridin-2-yl)propanoate. Under argon, 2-(6-methoxy-3-nitropyridin-2-yl)acetonitrile (500 mg, 2.59 mmol) was dissolved in acetonitrile (11 mL) in a flame dried round-bottom flask. Two equivalents of anhydrous potassium carbonate (0.72 g, 5.18 mmol) were added to this solution, and methyl 2-bromoacetate (245 μL, 2.59 mmol) was introduced dropwise. The reaction mixture was stirred at room temperature until the starting materials were consumed, approximately four hours. The crude material was combined with $CH_2Cl_2$ and inorganic debris was filtered off using a phase separator syringe equipped with a sodium sulfate drying cartridge. The filter cake was washed with small quantities of $CH_2Cl_2$ and all organic filtrates were collected and combined. The organic solvents were evaporated in vacuo at 40° C. and the resulting viscous dark brownish oil either directly used in the next reaction step or purified by flash chromatography on a short silica-gel column (ethyl acetate/hexane gradient) prior to its further chemical reaction. $C_{11}H_{11}N_3O_5$, $M_r$=265.22; $^1$H NMR (400 MHz, DMSO-$d_6$) d: 3.15-3.29 (m, 2H), 3.64 (s, 3H), 3.99 (s, 3H), 5.22 (t, J=7.2 Hz, 1H), 7.08 (d, J=9.2 Hz, 1H), 8.48 (d, J=8.8 Hz, 1H); LCMS (ESI) tR: 1.98 min (96-100%, UV220, UV254, ELSD), m/z: 266.2 [M+1]$^+$.

Example S: microwave-aided one-pot hydrogenation/cyclization reaction toward methyl 2-(5-methoxy-1H-pyrrolo[3,2-b]pyridin-3-yl)acetate. A 2 mL microwave process vial with a stir bar was charged with crude methyl 3-cyano-3-(6-methoxy-3-nitropyridin-2-yl)propanoate (50 mg, 0.19 mmol), 10% Pd/C (5 Mol %, 20 mg, 0.01 mmol), and methanol (1.5 mL). An excess of 1,4-cyclohexadiene (91 mg, 1.13 mmol) was added and the vessel flooded with argon, capped and heated under microwave conditions at 120° C. for 5 min. The reaction was filtered through CELITE® and the solvent was evaporated in vacuo. The crude material was purified by flash chromatography ($SiO_2$, ethyl acetate/hexane gradient) to yield the product as colorless oil. $C_{11}H_{12}N_2O_3$, $M_r$=220.22; $^1$H NMR (400 MHz, DMSO-$d_6$) d: 3.61 (s, 3H), 3.72 (s, 2H), 3.83 (s, 3H), 6.53 (d, J=8.8 Hz, 1H), 7.38 (d, J=2.8 Hz, 1H), 7.66 (d, J=8.4 Hz, 1H), 11.01 (bs, 1H); $^{13}$C NMR (100 MHz, DMSO-$d_6$) d: 29.41 (s, —$CH_2$—), 51.86 (s, —C(O)$OCH_3$), 52.83 (s, —$OCH_3$), 104.86 (s, C6'), 107.19 (s, C3'), 122.78 (s, C2'), 124.60 (s, C7a'), 126.80 (s, C7'), 141.29 (s, C3a'), 159.16 (s, C5'), 172.47 (s, >C=O); LCMS (ESI) tR: 0.69 min (>97%, UV220, ELSD), m/z: 221.2 [M+1]$^+$.

Example 2

Exemplary Screening Strategy

Inhibitors were initially screened for an ability to block the NADP+ dependent oxidation of the artificial substrate S-tetralol catalyzed by AKR1C3. S-tetralol was used since it is also a substrate of the highly related AKR1C1 and AKR1C2 enzymes. Inhibition of AKR1C1 and AKR1C2 is undesirable in the context of prostate cancer since they are involved in the elimination of DHT (see FIG. 1B; see also Rizner et al, 2003; Steckelbroeck et al. 2004).

Initially, the ratios of $IC_{50}$ values for AKR1C2 versus AKR1C3 were compared. High ratios were indicative of high selectivity for AKR1C3. Compounds that did not inhibit AKR1C2 were unlikely to inhibit AKRC1, since AKR1C2 and AKR1C1 share 96% sequence identity. All assays were performed at $K_m$ so that $IC_{50}$ values across enzyme forms were comparable.

Figure 9A:
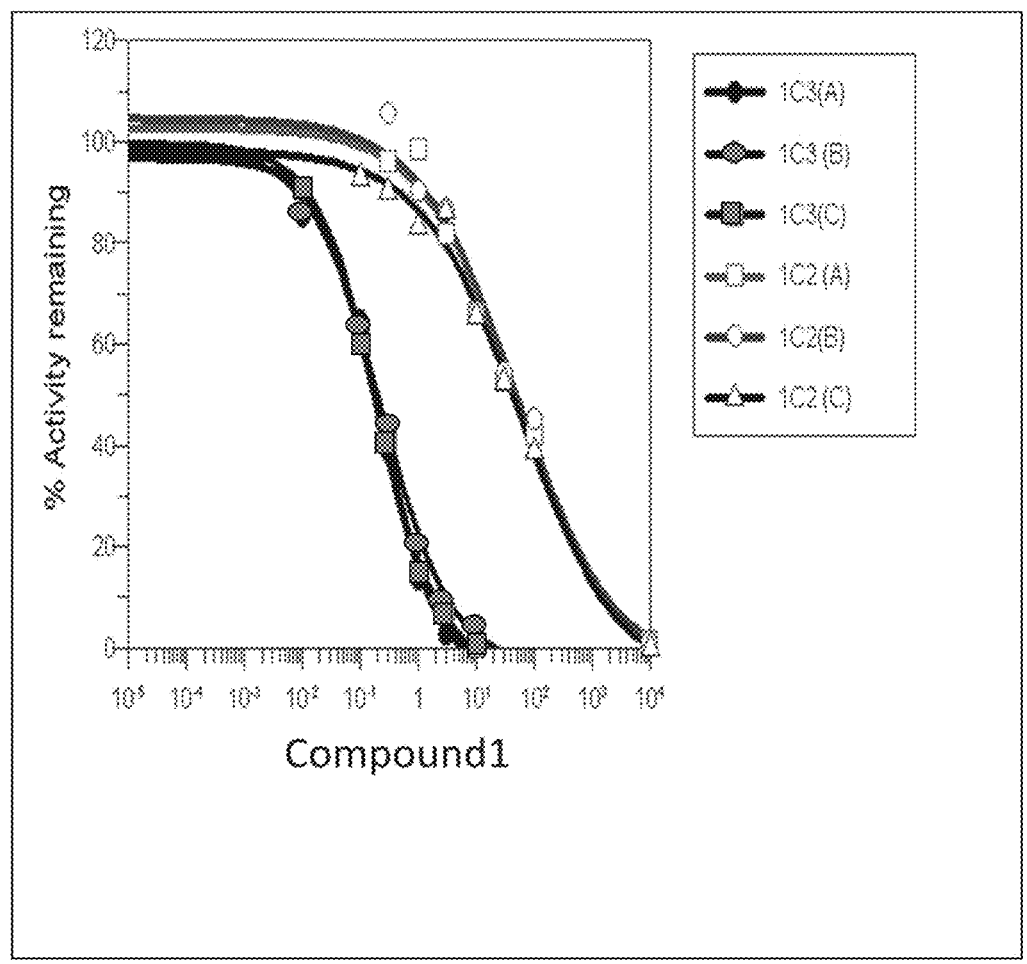
FIGS. 9A and 9B depict exemplary selective inhibition of AKR1C3 by Compound 1 and Compound 3, respectively.
Figure 9B:
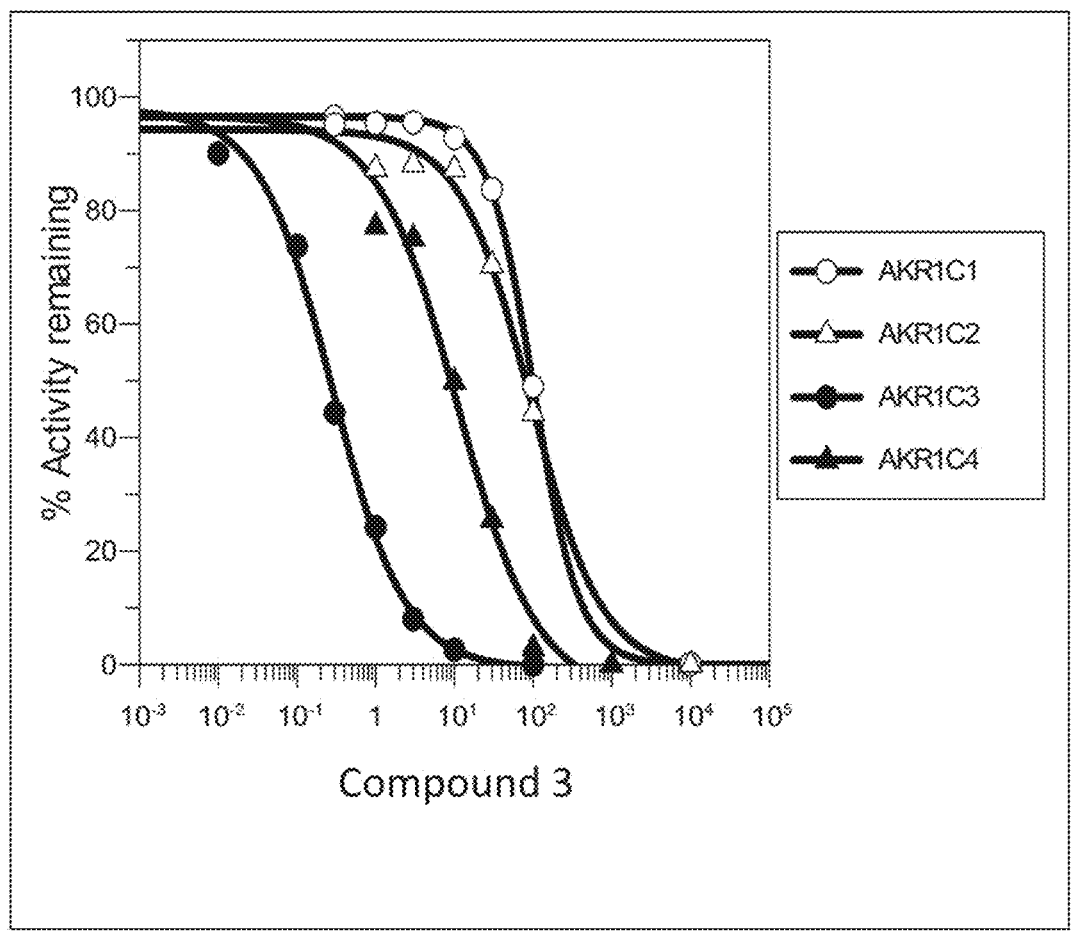

An exemplary screening strategy was against homogeneous recombinant AKR1C3 and its highly related enzyme AKR1C2 to generate full dose-response curves and $IC_{50}$ values. Compounds 1, 2, and 3 showed 240, 111, and 275-fold selectivity for inhibition of AKR1C3 over AKR1C2, respectively (see Table 2). Congeners of the Compound 4, 5 Series and the Compound 6 Series showed similar potency and selectivity. In each case, the $IC_{50}$ values for AKR1C3 were in the mid-nanomolar range. Exemplary dose response curves are shown in FIGS. 9A and 9B.

TABLE 2

Summary of Inhibition Data for Indomethacin Analogs

| Compound | AKR1C3[a] | AKR1C1[a] | AKR1C2[a] | AKR1C4[a] |
|---|---|---|---|---|
| Compound 1 | 0.21 | >100 (>478) | 50.13 (240) | >100 (>478) |
| Compound 2 | 0.13 | 17.73 (136) | 14.45 (111) | 3.51 (27) |
| Compound 3 | 0.34 | 100 (296) | 93.0 (275) | 12.64 (37) |
| Des-methylIndomethacin | 0.96 | >100 (>100) | 100 (100) | 48.7 (357) |

TABLE 2-continued

Summary of Inhibition Data for Indomethacin Analogs

| Compound | AKR1C3[a] | AKR1C1[a] | AKR1C2[a] | AKR1C4[a] |
|---|---|---|---|---|
| (5-methoxy-2-methyl-1-(4-chlorobenzoyl)indol-3-yl)acetamide N-trifluoromethanesulfonyl | 0.74 | >100 (>135) | 81.0 (108) | >100 (>135) |
| 3-(5-methoxy-2-methyl-1-(4-chlorobenzoyl)indol-3-yl)propanoic acid | 0.22 | >100 (>455) | 57.0 (257) | >100 (>455) |
| (5-methoxy-2-methyl-1-(4-methylbenzoyl)indol-3-yl)acetic acid | 0.16 | >100 (>625) | 54.50 (336) | >100 (>625) |
| (5-methoxy-2-methyl-1-(4-(chloromethyl)benzoyl)indol-3-yl)acetic acid | 0.12 | 100 (833) | 40.74 (329) | 49.75 (415) |

TABLE 2-continued

Summary of Inhibition Data for Indomethacin Analogs

| Compound | AKR1C3[a] | AKR1C1[a] | AKR1C2[a] | AKR1C4[a] |
|---|---|---|---|---|
| (structure: 5-methoxy-2-methyl-1-(4-trifluoromethylbenzoyl)indol-3-yl acetic acid) | 0.27 | >100 (>370) | 35.73 (134) | >100 (>370) |
| (structure: 5-methoxy-3-ethyl-1-(4-chlorobenzoyl)indol-2-yl propanoic acid) | 0.09 | 30.71 (341) | 49.57 (538) | 1.95 (22) |
| (structure: 6-methoxy-9-(4-chlorobenzoyl)-2,3,4,9-tetrahydro-1H-carbazole-3-carboxylic acid) | 0.16 | 76.25 (477) | 53.50 (331) | 3.15 (20) |

[a]Numbers in parenthesis indicates fold selectivity for AKR1C3

Example 3

Exemplary Secondary Screening Strategies

Figure 10:
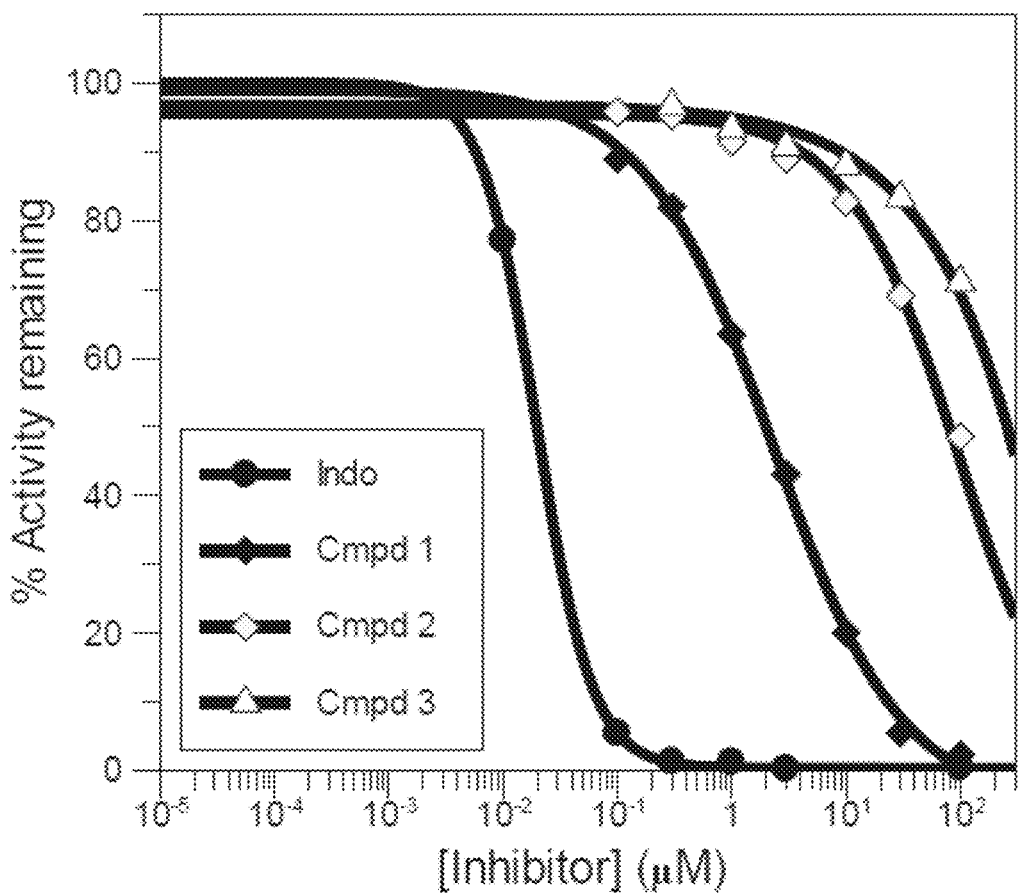
FIG. 10 depicts exemplary lack of COX-1 inhibitory activity by Compounds 1, 2, and 3 relative to indomethacin.
Figure 11A:
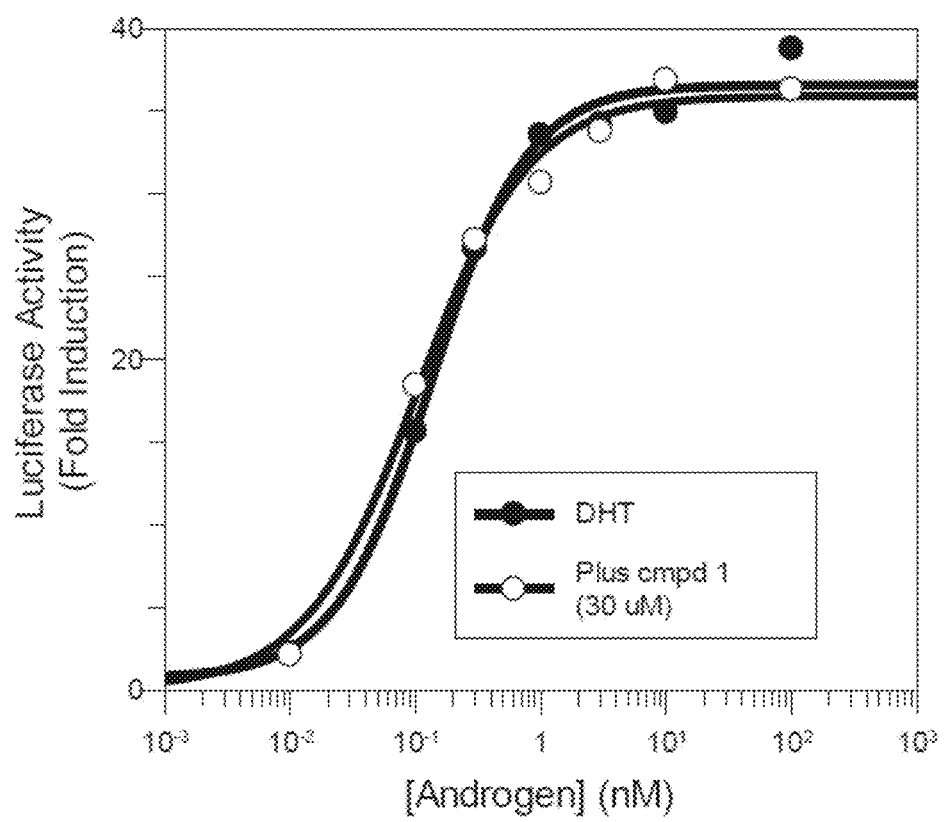
FIGS. 11A and 11B depict exemplary lack of androgen receptor antagonism by Compound 1, and Compounds 2 and 3, respectively, in a luciferase androgen receptor reporter gene assay driven by DHT.
Figure 11B:
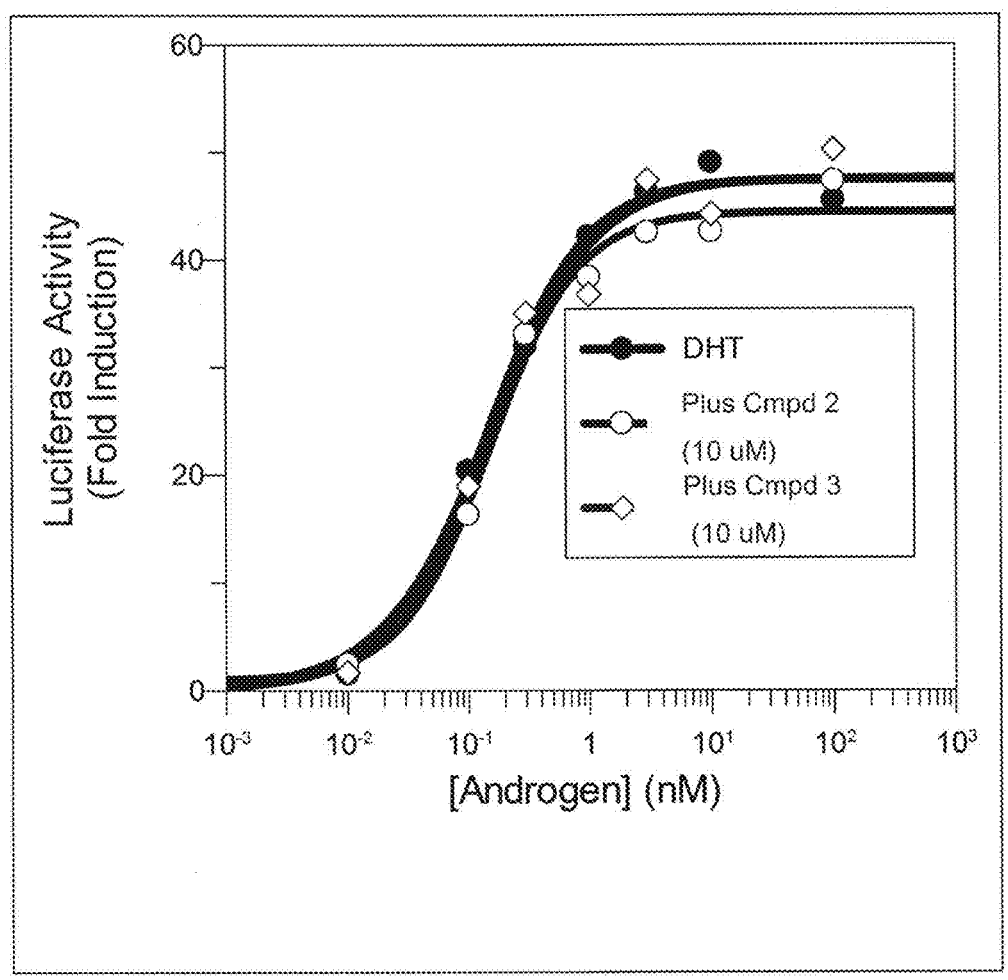
Figure 12A:
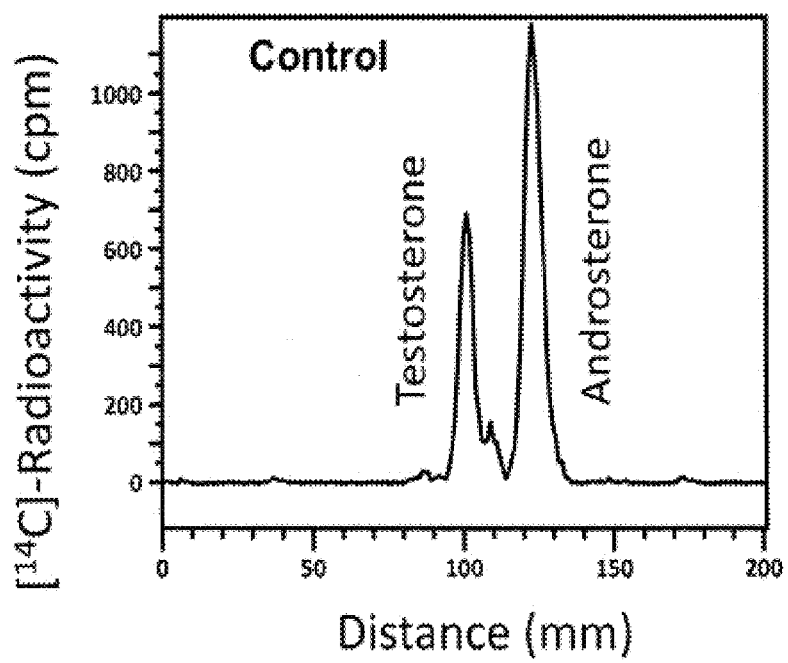
FIGS. 12A-12D depict exemplary inhibition of the conversion of [$^{14}$C]-androst-4-ene-3,17-dione to testosterone by indomethacin (FIG. 12B); Compound 2 (FIG. 12C); and Compound 3 (FIG. 12D) in LNCaP cells (an androgen dependent prostate cancer cell line) genetically engineered to stably express AKR1C3.
Figure 12B:
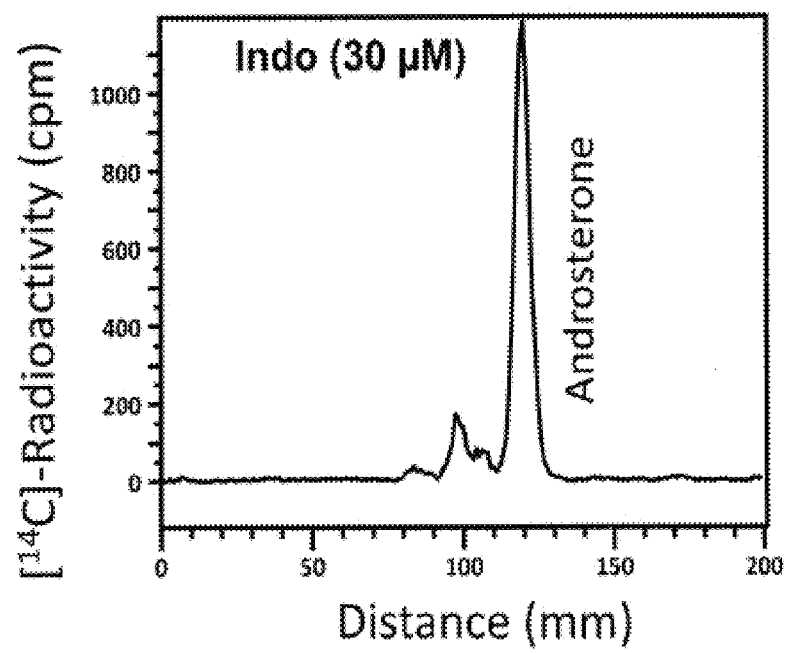
Figure 12C:
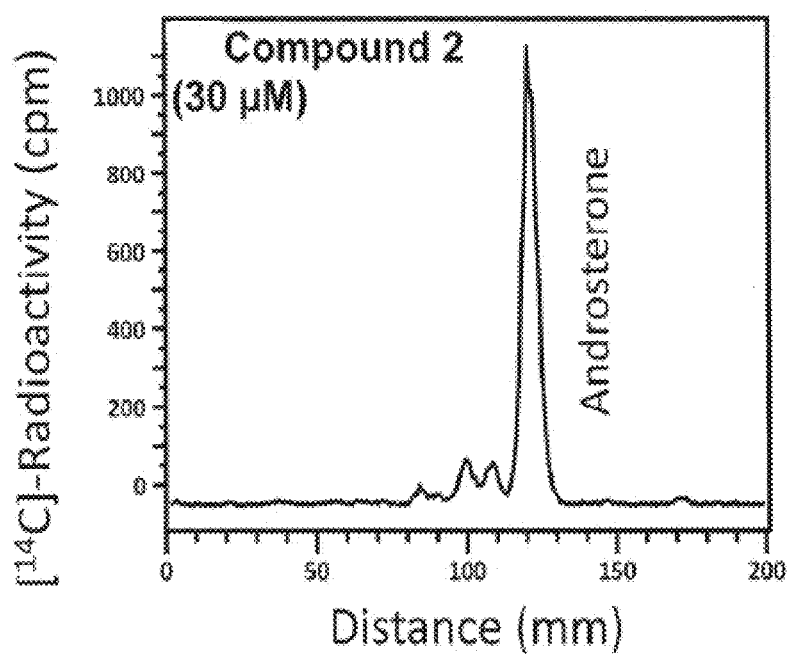
Figure 12D:
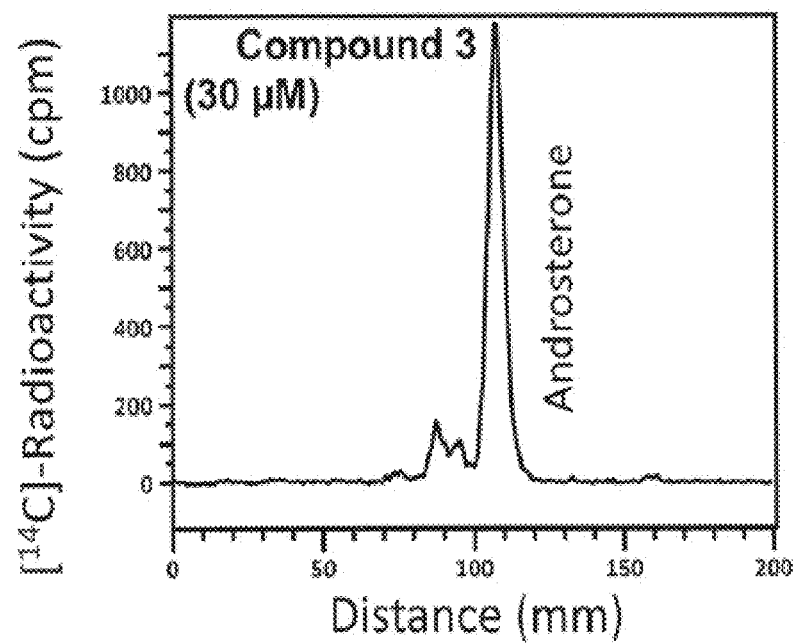

Secondary screens involve one or more of: (a) a full-screen against all nine human recombinant AKR enzymes to ensure there are no-intended off-target effects; (b) a screen against COX-1 and COX-2 to reaffirm that compounds will not act as NSAIDs; and (c) a HeLa-cell androgen receptor (AR) reporter gene assay. The latter assay is used to determine whether lead compounds act as AR agonists or block 5α-DHT reporter gene activity by acting as androgen receptor antagonists. It is noted that lead Compounds 2 and 3 did not inhibit COX-1 at concentrations greater than 100 μM (see FIG. 10). It is further noted that Compounds 1, 2, and 3 did not act as AR agonists or antagonists. Thus, they failed to block DHT stimulation of the AR in an AR luciferase reporter gene assay (see FIGS. 11A and 11B).

Example 4

Exemplary Tertiary Screening Strategies

Tertiary screens involve one or more of (d) expanded reporter gene assays to determine whether compounds act as agonists or antagonists of other steroid hormone receptors; (e) inhibition of the conversion of $\Delta^4$-androstene-3,17-dione to testosterone in androgen receptor dependent prostate cancer cells (including, but not limited to LNCaP; available from the American type Culture Collection (ATCC), Manassas, Va., United States of America) stably transfected with AKR1C3; and (f) inhibition of growth of castrate-resistant prostate cancer cells in a murine xenograft model.

Figure 13:
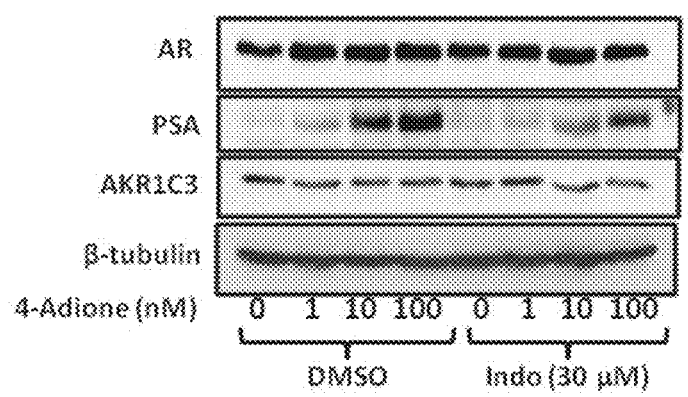
FIG. 13, depicts exemplary inhibition of androgen dependent gene expression, PSA (prostatic specific antigen) mediated by $\Delta^4$-androstene-3,17-dione (4-Adione) in VCaP cells (a human androgen dependent castrate resistant prostate cancer cell line) by indomethacin.
Figure 14A:
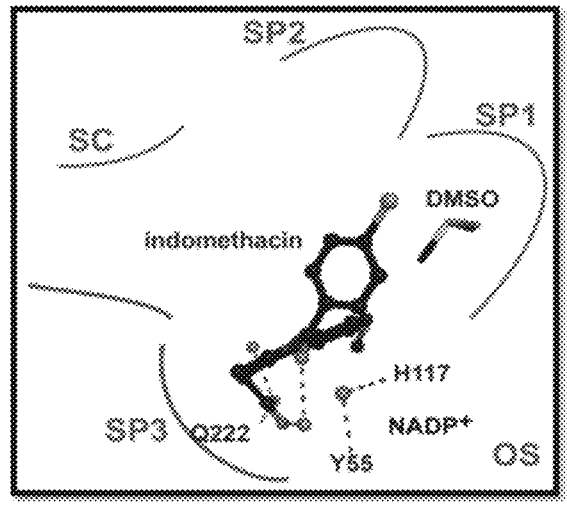
FIGS. 14A-14D, depicts the binding pose of des-methyl indomethacin (compound of formula 1) bound in a unique position in the AKR1C3 protein (PDB 4DBW embargoed). X-ray crystal structures of AKR1C3•NADP$^+$•Indomethacin (FIGS. 14A and 14B) [PDB-1S2A] and AKR1C3•NADP$^+$•desmethyl indomethacin (DM-INDO.
Figure 14B:
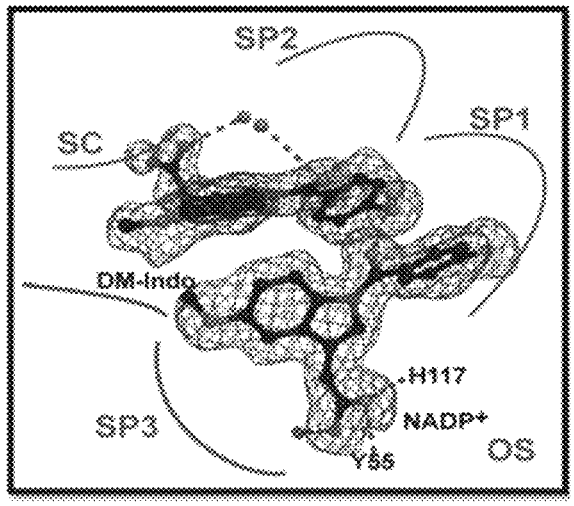
Figure 14C:
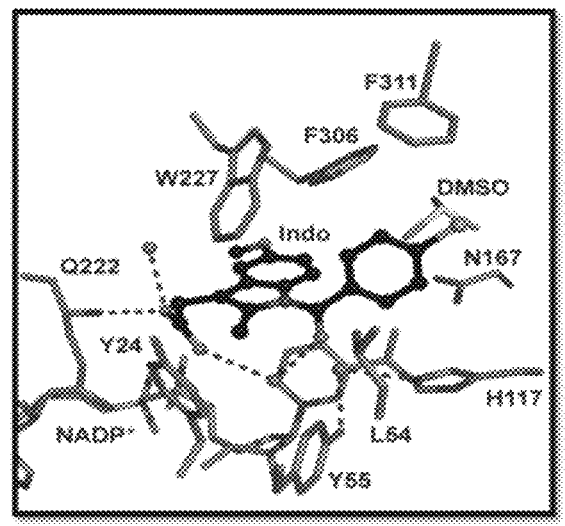
Figure 14D:
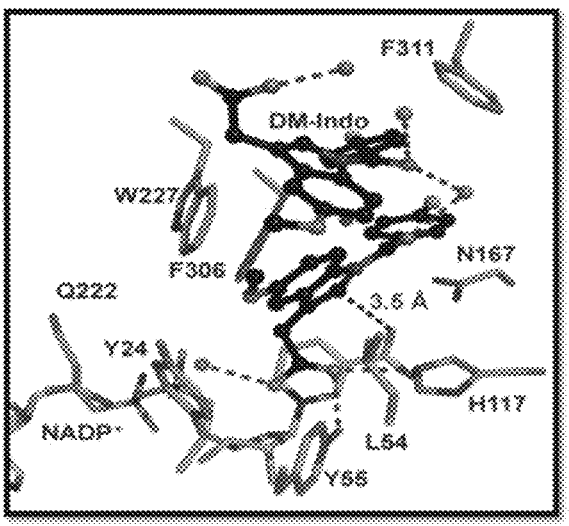

Lead Compounds 2 and 3 completely blocked the conversion of $\Delta^4$-androstene-3,17-dione to testosterone in LNCaP-AKR1C3 transfected cells at a concentration of 30 μM (see FIG. 12). Using the castrate-resistant prostate cancer cell line VCaP, indomethacin blocked the $\Delta^4$-androstene-3,17-dione driven expression of PSA (see FIG. 13). Using the VCaP cells in a murine xenograft model, indomethacin was shown to block AR dependent gene transcription and cell growth and proliferation of the tumor (see Cai et al., 2011).

REFERENCES

All references listed in the instant disclosure, including but not limited to all patents, patent applications and publications thereof, scientific journal articles, and database entries (including but not limited to GENBANK® database entries and including all annotations available therein) are incorporated herein by reference in their entireties to the extent that they supplement, explain, provide a background for, and/or teach methodology, techniques, and/or compositions employed herein.

Adeniji et al. (2011) Discovery of substituted 3-(phenylamino)benzoic acids as potent and selective inhibitors of type 5 17β-hydroxysteroid dehydrogenase (AKR1C3). *Bioorg Med Chem Lett* 21:1464-1468.

Adeniji et al. (2012) Development of potent and selective inhibitors of aldo-keto reductase 1C3 (type 5 17β-hydroxysteroid dehydrogenase) based on N-phenyl-aminobenzoates and their structure activity relationships. *J. Med. Chem.* 55: 2311-2323.

Andriole et al. (2010) REDUCE Study Group. Effect of dutasteride on the risk of prostate cancer, *N Engl J Med* 362:1192-1202.

Attard et al. (2009a) Antitumor activity with CYP17 blockade indicates that castration-resistant prostate cancer frequently remains hormone driven, *Cancer Res* 69:4937-4940.

Attard et al. (2009b) Selective inhibition of CYP17 with abiraterone acetate is highly active in the treatment of castration-resistant prostate cancer, *J Clin Oncol* 27:3742-37482.

Berkow et al. (1997) *The Merck Manual of Medical Information, Home ed.*, Merck Research Laboratories, Whitehouse Station, N.J.

Byrns et al. (2008) An indomethacin analogue N-(4-chlorobenzoyl)melatonin is a selective inhibitor of aldo-keto reductase 1C3 (type 2 3a-HSD, type 5 17b-HSD and prostaglandin F synthase), a potential target for the treatment of hormone dependent and hormone independent malignancies, *Biochem Pharmacol* 75:484-493.

Cai et al. (2011) Intratumoral De Novo Steroid Synthesis Activates Androgen Receptor in Castration-Resistant Prostate Cancer and Is Upregulated by Treatment with CYP17A1 Inhibitors, *Cancer Res* 71:6503-6513.

Davies et al. (2009) AKR1C isoforms represent a novel cellular target for jsamonate alongside their mitochondrial-mediated effects, *Cancer Res* 69:4769-4775.

Duch et al. (1998) Volatile anesthetics significantly suppress central and peripheral mammalian sodium channels. *Toxicol Lett* 100-101:255-263.

Ebadi (1998) *CRC Desk Reference of Clinical Pharmacology.* CRC Press, Boca Raton, Fla.

Efstathiou et al. (2011) MDV3100 effects on androgen receptor (AR) signaling and bone marrow testosterone concentration modulation: A preliminary report. *J. Clin. Onc.*, ASCO Meeting Abstracts: p. Abstract 4501.

Foster et al. (2011) Drug safety is a barrier to the discovery and development of new androgen receptor antagonists. *Prostate* 71: 480-488.

Freireich et al. (1966) Quantitative comparison of toxicity of anticancer agents in mouse, rat, hamster, dog, monkey, and man. *Cancer Chemother Rep* 50:219-244.

Fung et al. (2006) Increased expression of type 2 3a-hydroxysteroid dehydrogenase/type 5 17b-hydroxysteroid dehydrogenase (AKR1C3) and its relationship with the androgen receptor in prostate carcinoma, *Endocr Related Cancer* 13:169-180.

GENBANK® database Accession Nos. NM_001012344; NM_001038584; NM_001078713; NM_001134068; NM_003739; NP_001012344; NP_001033673; NP_001072181; NP_001127540; NP_003730; XM_001118637; XM_003312435; XP_001118637; XP_003312483.

Gerbino (2005) *Remington: The Science and Practice of Pharmacy.* 21st Edition. Lippincott Williams & Wilkins, Philadelphia, Pa.

Goodman et al. (1996) *Goodman & Gilman's the Pharmacological Basis of Therapeutics, 9th ed.*, McGraw-Hill Health Professions Division, New York.

Harris & Phipps (2002) Prostaglandin D2, its metabolite 15-d-PGJ2, and peroxisome proliferator activated receptor-γ agonists induce apoptosis in transformed, but not normal, human T lineage cells, *Immunology* 105:23-34.

Hu et al. (2012) Distinct transcriptional programs mediated by the ligand-dependent full-length androgen receptor and its splice variants in castration-resistant prostate cancer. *Cancer Res.* 72: 3457-3462.

Jansson et al. (2006) 17β-Hydroxysteroid dehydrogenase 14 affects estradiol levels in breast cancer cells and is a prognostic marker in estrogen receptor-positive breast cancer, *Cancer Res* 66:11471-11477.

Jermal et al. (2007) Cancer Statistics, *Cancer J Clin* 57:43-66.

Katzung (2001) *Basic & Clinical Pharmacology, 8th ed.*, Lange Medical Books/McGraw-Hill Medical Pub. Division, New York.

Khanim et al. (2009) Combined bezafibarte and medroxyprogesterone acetate: potential novel therapy for acute myeloid leukemia, *PLoS ONE* 2009:e1847.

Kim et al. (2007) 15-Deoxy-Δ12,14-prostaglandin J2 inhibits transcriptional activity of estrogen receptor-α via covalent modification of DNA-binding domain, *Cancer Res* 67:2595-2602.

Knudsen & Penning (2010) Partners in crime: deregulation of AR activity and androgen synthesis in prostate cancer, *Trends Endocrinol Metab* 21:315-324.

Knudsen & Scher (2009) Starving the addiction: New opportunities for durable suppression of AR signaling in prostate cancer, *Clin Cancer Res* 15:4792-4798.

Krazeisen et al. (2002) Human 17b-hydroxysteroid dehydrogenase type 5 is inhibited by dietary flavonoids, *Adv Exp Med Biol* 505:151-161.

Lin et al. (1997) Expression and characterization of recombinant type 2 3a-hydroxysteroid dehydrogenase (HSD) from human prostate: demonstration of bifunctional 3a/17b-HSD activity and cellular distribution, *Mol Endocrinol* 11:1971-1984.

Lin et al. (2004) Characterization of a monoclonal antibody for human aldo-keto reductase AKR1C3 (type 2 3a-hydroxysteroid dehydrogenase/type 5 17β-hydroxysteroid dehydrogenase); immunohistochemical detection in breast and prostate, *Steroids* 69:795-801.

Matsuura et al. (1998) Identification of a principal mRNA species for human 3α-hydroxysteroid dehydrogenase isoform (AKR1C3) that exhibits high prostaglandin D2 11-ketoreductase activity, *J Biochem* 124:940-946.

Milne & Jabbour (2003) Prostaglandin (PG) F2α receptor expression and signaling in human endometrium: role of PGF2α in epithelial cell proliferation, *J Clin Endocrinol Metab* 88:1825-1832.

Mitsiades et al. (2012) Distinct patterns of dysregulated expression of enzymes involved in androgen synthesis and metabolism in metastatic prostate cancer tumors. *Cancer Res.* [Epub ahead of print]

Montgomery et al. (2008) Maintenance of intratumoral androgens in metastatic prostate cancer: a mechanism for castration-resistant tumor growth, *Cancer Res* 68:4447-4454.

Mostaghel et al. (2011) Resistance to CYP17A1 inhibition with abiraterone in castrate-resistance prostate cancer: induction of steroidogenesis and androgen receptor splice variants. *Clin. Cancer Res.,* 17: 5913-5925.

PCT International Publication Nos. WO 1993/25521; WO 2007/100066; WO 2009/014150.

Penning et al. (2000) Human 3a-hydroxysteroid dehydrogenase isoforms (AKR1C1-AKR1C4) of the aldo keto reductase superfamily: functional plasticity and tissue distribution reveals roles in the inactivation and formation of male and female sex hormones, *Biochem J* 351:67-77.

Penning et al. (2006) Aldo-keto reductase (AKR) 1C3: Role in prostate disease and the development of specific inhibitors, *Mol Cell Endcorinol* 248:182-191.

Prusakiewicz et al. (2004) Molecular basis of the time-dependent inhibition of cyclooxygenases by indomethacin, *Biochemistry* 43:15439-15445.

Qui et al. (2007) Structure-based inhibitor design for an enzyme the binds different steroids: a potent inhibitor for human type 5 17b-hydroxysteroid dehydrogenase, *J Biol Chem* 282:8368-8379.

Reid et al. (2010) Significant and sustained antitumor activity in post-docetaxel, castration-resistant prostate cancer with the CYP17 inhibitor abiraterone acetate, *J Clin Oncol* 28:1489-1495.

Remington et al. (1975) *Remington's Pharmaceutical Sciences, 15th ed.*, Mack Pub. Co., Easton, Pa.

Rizner et al., (2003) Human type 3 3alpha-hydroxysteroied dehydrogenase (aldo-keto reductase $1C_2$) and androgen metabolism in prostate cancer cells. *Endocrinology* 144: 2922-2932

Sales et al. (2004) Expression, localization, and signaling of prostaglandin F2α receptor in human endometrial adenocarcinoma: regulation of proliferation by activation of the epidermal growth factor receptor and mitogen-activated protein kinase signaling pathways, *J Clin Endocrinol Metab* 89:986-993.

Sales et al. (2005) A novel angiogenic role for prostaglandin F2α-FP receptor interaction in human endometrial adenocarcinomas, *Cancer Res* 65:7707-7716.

Scher et al. (2010) Prostate Cancer Foundation/Department of Defense Prostate Cancer Clinical Trials Consortium, Antitumour activity of MDV3100 in castration-resistant prostate cancer: a phase 1-2 study, *Lancet* 375:1437-1446.

Shiraki et al. (2005) α, β-Unsaturated ketone is a core moiety of natural ligands for covalent binding to peroxisome proliferator-activated receptor γ, *J Biol Chem* 280: 14145-14153.

Skarydova et al. (2009) AKR1C3 as a potential target for the inhibitory effect of dietary flavonoids, *Chem Biol Inter* 178:138-144.

Speight et al. (1997) *Avery's Drug Treatment: A Guide to the Properties, Choice, Therapeutic Use and Economic Value of Drugs in Disease Management, 4th ed*. Adis International, Auckland/Philadelphia.

Stanbrough et al. (2006) Increased expression of genes converting adrenal androgens to testosterone in androgen-independent prostate cancer, *Cancer Res* 66:2815-2825.

Steckelbroeck et al. (2004) Human cytosolic 3alpha-hydroxysteroid dehydrogenases of the aldo-keto reductase superfamily display significant 3beta-hydroxysteroid dehydrogenase activity: implications for steroid hormone metabolism and action.

Stefane et al. (2009) New cylcopentane derivatives as inhibitors of steroid metabolizing enzymes AKR1C1 and AKR1C3, *Eur J Med Chem* 44:2563-2571.

Straus et al. (2000) 15-Deoxy-Δ12,14-prostaglandin J2 inhibits multiple steps in the NF-κB signaling pathway, *Proc Nat Acad Sci USA* 97:4844-4849.

Suzuki et al. (2007) In situ production of sex steroids in human breast carcinoma, *Med Mol Morphol* 40:121-127

Suzuki-Yamamoto et al. (1999) cDNA cloning, expression and characterization of human prostaglandin F synthase, *FEBS Lett* 462:335-340.

Thompson et al. (2007) Prediction of prostate cancer for patients receiving finasteride: results from the Prostate Cancer Prevention Trial, *J Clin Oncol* 25:3076-3081.

Tran et al. (2009) Development of a second-generation antiandrogen for treatment of advanced prostate cancer, *Science* 324:787-790.

U.S. Patent Application Publication No. 2006/0188558

U.S. Pat. Nos. 3,598,122; 5,016,652; 5,234,933; 5,326,902; 5,935,975; 6,106,856; 6,162,459; 6,180,082; 6,495,605; 6,582,724; 7,405,227

Usami et al. (2002) Substrate specificity of human 3(20a)-hydroxysteroid dehydrogenase for neurosteroids and its inhibition by benzodiazepines, *Biol Pharm Bull* 25:441-445.

Vasaitis et al. (2008) Androgen receptor inactivation contributes to antitumor efficacy of 17a-hydroxylase/17,20-lyase inhibitor 3b-hydroxy-17-(1H-benzimidazole-1-yl) androsta-5,16-diene in prostate cancer, *Mol Cancer Therap* 7:2348-2357.

Veliça et al. (2009) Lack of functional and expression homology between human and mouse aldo-keto reductase 1C enzymes: implications for modelling human cancers, *Mol Cancer* 14:121.

Walsh (2010) Chemoprevention of prostate cancer, *New Engl J Med* 362:1237-1238.

It will be understood that various details of the presently disclosed subject matter may be changed without departing from the scope of the presently disclosed subject matter. Furthermore, the foregoing description is for the purpose of illustration only, and not for the purpose of limitation.

What is claimed is:

1. A method for inhibiting a biological activity of an aldo-keto reductase family 1, member C3 (AKR1C3) polypeptide, the method comprising contacting the AKR1C3 polypeptide with an effective amount of a compound of Formula III:

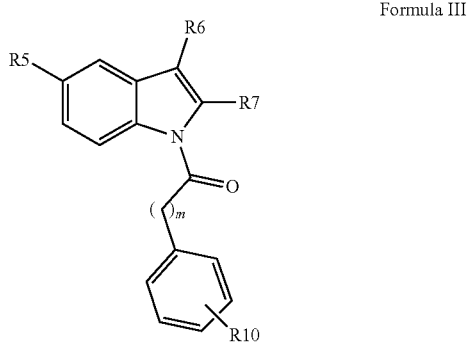

Formula III wherein:
- R5 is hydrogen, $C_1$ to $C_6$ alkoxy or halogen;
- R6 is $C_1$ to $C_6$ alkyl or $C_1$ to $C_6$ alkylcarboxylic acid or $C_1$ to $C_6$ alkyl-C(O)OR12 or $C_1$ to $C_6$ alkyl- C(O)N(H)SO$_2$X;
- R7 is hydrogen or $C_2$ to $C_6$ alkyl or $C_2$ to $C_6$ alkylcarboxylic acid or $C_2$ to $C_6$ alkyl-C(O)OR12 or $C_2$ to $C_6$ alkyl- C(O)N(H)SO$_2$X;
- R10 is present in two, three, four, or five positions in the phenyl ring and each instance is independently selected from the group consisting of hydrogen, halogen, nitro, $C_1$ to $C_6$ alkyl, singly or multiply halogen substituted $C_1$ to $C_6$ alkyl, $C_1$ to $C_6$ alkoxy, amino, and hydroxy;
- X is methyl or singly or multiply halogen substituted methyl; phenyl, optionally singly or multiply substituted phenyl or thiophenyl, wherein the single or multiple substitutions of the phenyl or thiophenyl are each independently selected from the group consisting of halogen, nitro, $C_1$ to $C_6$ alkyl, singly or multiply halogen substituted $C_1$ to $C_6$ alkyl, trifluoromethyl, acetyl, isopropyl, $C_1$ to $C_6$ alkoxy, trifluoromethyloxy, phenoxy, cyano, hydroxy, and amino; and
- m is 0 or 1.

2. The method of claim 1, wherein the compound has the following structure:

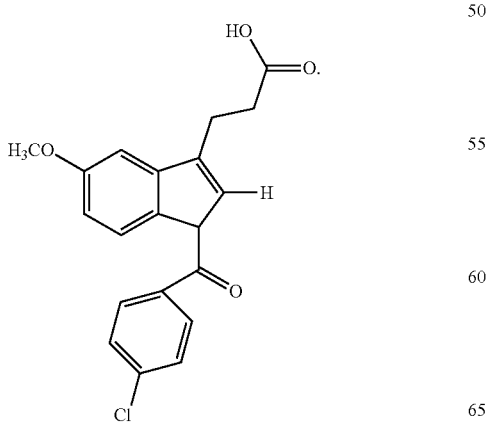

3. The method of claim 1, wherein the AKR1C3 polypeptide is present within a subject.

4. The method of claim 3, wherein the subject is a mammal.

5. The method of claim 3, wherein the subject is a male and the AKR1C3 polypeptide is present in the prostate of the subject.

6. The method of claim 5, wherein the prostate of the subject comprises a tumor, optionally a castrate-resistant tumor.

7. A method for inhibiting undesirable aldo-keto reductase family 1, member C3 (AKR1C3) biological activity in a subject, the method comprising administering to the subject an effective amount of a compound of Formula III:

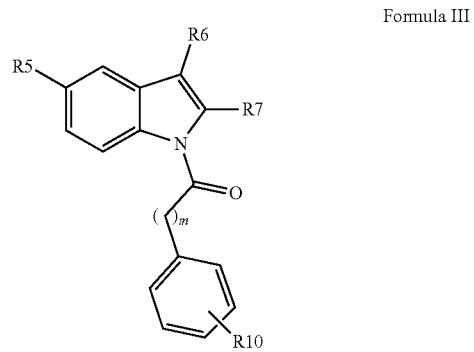

Formula III wherein:
- R5 is hydrogen, $C_1$ to $C_6$ alkoxy or halogen;
- R6 is $C_1$ to $C_6$ alkyl or $C_1$ to $C_6$ alkylcarboxylic acid or $C_1$ to $C_6$ alkyl-C(O)OR12 or $C_1$ to $C_6$ alkyl- C(O)N(H)SO$_2$X;
- R7 is hydrogen or $C_2$ to $C_6$ alkyl or $C_2$ to $C_6$ alkylcarboxylic acid or $C_2$ to $C_6$ alkyl-C(O)OR12 or $C_2$ to $C_6$ alkyl- C(O)N(H)SO$_2$X;
- R10 is present in two, three, four, or five positions in the phenyl ring and each instance is independently selected from the group consisting of hydrogen, halogen, nitro, $C_1$ to $C_6$ alkyl, singly or multiply halogen substituted $C_1$ to $C_6$ alkyl, $C_1$ to $C_6$ alkoxy, amino, and hydroxy;
- X is methyl or singly or multiply halogen substituted methyl; phenyl, optionally singly or multiply substituted phenyl or thiophenyl, wherein the single or multiple substitutions of the phenyl or thiophenyl are each independently selected from the group consisting of halogen, nitro, $C_1$ to $C_6$ alkyl, singly or multiply halogen substituted $C_1$ to $C_6$ alkyl, trifluoromethyl, acetyl, isopropyl, $C_1$ to $C_6$ alkoxy, trifluoromethyloxy, phenoxy, cyano, hydroxy, and amino; and
- m is 0 or 1.

8. The method of claim 7, wherein the compound has the following structure:

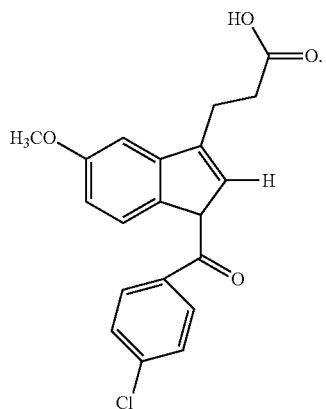 [SMILES: COc1ccc2c(c1)C(CCC(=O)O)=CC2C(=O)c1ccc(Cl)cc1]

9. The method of claim 7, wherein the subject is a mammal.

10. The method of claim 9, wherein the subject is a male and the undesirable AKR1C3 biological activity is present in a tumor, optionally a castrate-resistant tumor, present in the prostate of the subject.

11. A method for treating a prostate tumor in a subject, the method comprising administering the subject a therapeutically effective amount of a compound of Formula III:

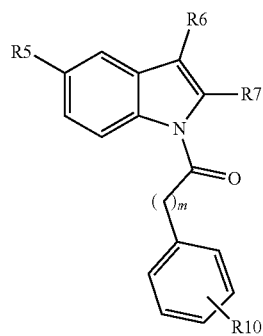

Formula III wherein:
R5 is hydrogen, $C_1$ to $C_6$ alkoxy or halogen;
R6 is $C_1$ to $C_6$ alkyl or $C_1$ to $C_6$ alkylcarboxylic acid or $C_1$ to $C_6$ alkyl-C(O)OR12 or $C_1$ to $C_6$ alkyl- C(O)N(H)SO$_2$X;
R7 is hydrogen or $C_2$ to $C_6$ alkyl or $C_2$ to $C_6$ alkylcarboxylic acid or $C_2$ to $C_6$ alkyl-C(O)OR12 or $C_2$ to $C_6$ alkyl- C(O)N(H)SO$_2$X;
R10 is present in two, three, four, or five positions in the phenyl ring and each instance is independently selected from the group consisting of hydrogen, halogen, nitro, $C_1$ to $C_6$ alkyl, singly or multiply halogen substituted $C_1$ to $C_6$ alkyl, $C_1$ to $C_6$ alkoxy, amino, and hydroxy;
X is methyl or singly or multiply halogen substituted methyl; phenyl, optionally singly or multiply substituted phenyl or thiophenyl, wherein the single or multiple substitutions of the phenyl or thiophenyl are each independently selected from the group consisting of halogen, nitro, $C_1$ to $C_6$ alkyl, singly or multiply halogen substituted $C_1$ to $C_6$ alkyl, trifluoromethyl, acetyl, isopropyl, $C_1$ to $C_6$ alkoxy, trifluoromethyloxy, phenoxy, cyano, hydroxy, and amino; and
m is 0 or 1.

12. The method of claim 11, wherein the compound has the following structure:

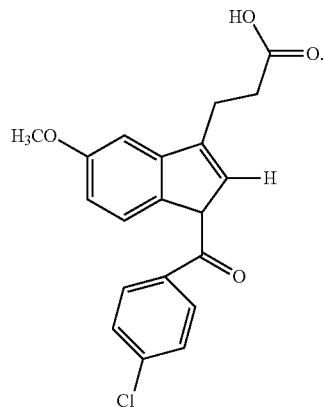 [SMILES: COc1ccc2c(c1)C(CCC(=O)O)=CC2C(=O)c1ccc(Cl)cc1]

13. The method of claim 11, wherein the prostate tumor is a castrate-resistant prostate tumor.

14. The method of claim 11, wherein the administering is via a route selected from the group consisting of peroral, intravenous, intraperitoneal, inhalation, intraprostatic, and intratumoral.

* * * * *